(12) United States Patent
Zhang et al.

(10) Patent No.: US 8,772,308 B2
(45) Date of Patent: Jul. 8, 2014

(54) NON-PEPTIDYL, POTENT, AND SELECTIVE MU OPIOID RECEPTOR ANTAGONISTS

(75) Inventors: Yan Zhang, Richmond, VA (US); Dana E. Selley, Richmond, VA (US); William Dewey, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 266 days.

(21) Appl. No.: 13/144,788

(22) PCT Filed: Jan. 15, 2010

(86) PCT No.: PCT/US2010/021157
§ 371 (c)(1),
(2), (4) Date: Sep. 1, 2011

(87) PCT Pub. No.: WO2010/083384
PCT Pub. Date: Jul. 22, 2010

(65) Prior Publication Data
US 2011/0306628 A1    Dec. 15, 2011

Related U.S. Application Data

(60) Provisional application No. 61/145,379, filed on Jan. 16, 2009.

(51) Int. Cl.
*A61K 31/485*    (2006.01)
*C07D 489/08*    (2006.01)

(52) U.S. Cl.
USPC .......................................... 514/282; 546/44

(58) Field of Classification Search
USPC ...................................... 514/282; 546/44, 45
See application file for complete search history.

(56) References Cited

U.S. PATENT DOCUMENTS

| 6,177,438 B1 * | 1/2001 | Nagase et al. ............. 514/280 |
| 7,320,984 B2 * | 1/2008 | Izumimoto et al. ......... 514/282 |
| 2010/0190728 A1 | 7/2010 | Cashman et al. |

FOREIGN PATENT DOCUMENTS

| WO | 2005/117589 A1 | 12/2005 |
| WO | 2007-056300 | 5/2007 |
| WO | 2010/006299 A1 | 1/2010 |

OTHER PUBLICATIONS

Ghirmai et al., "Synthesis and Biological Evaluation of alpha and beta-6-Amido Derivatives of 17-Cyclopropylmethy1-3, 14beta-dihydroxy-4, 5alpha-epoxymorphinan: Potential Alcohol-Cessation Agents", Journal of Medicinal Chemistry, ISSN: 0022-2623, DOI: 10.1021/JM701060E, Jan. 1, 2008, pp. 1913-1924, vol. 51, No. 6, American Chemical Society, US.

McCurdy et al., "Naphthalene dicarboxaldehyde as an electrophilic fluorogenic moiety for affinity labeling: application to opioid receptor affinity labels with greatly improved fluorogenic properties", Journal of Medicinal Chemistry, ISSN: 0022-2623, DOI: 10.1021/JM15586U, Jul. 4, 2002, pp. 2887-2890, vol. 45, No. 14, American Chemical Society, US.

Derrick et al., "Potential irreversible ligands for opioid receptors. Cinnamoyl derivatives of .beta.-naltrexamine", Journal of Pharmacy and Pharmacology, ISSN: 0022-3573, Caplus, Jan. 1, 1996, pp. 1-2.

Sayre et al., "Design and Synthesis of Naltrexone-derived affinity labels with nonequilibrium opioid agonist and antagonist activities", Journal of Medicinal Chemistry, ISSN: 0022-2623, DOI: 10.1021/JM00376A018, Jan. 1, 1984, pp. 1325-1335, vol. 27, No. 10, American Chemical Society, US.

Hatanaka Yasumaru et al., "Synthesis and characterization of novel photoreactive naltrexone analogs as isomeric carbene-generating probes for opioid receptors", Heterocycles, ISSN: 0385-5414, DOI: 10.3987/COM-95/7345, Jan. 1, 1996, pp. 519-522, vol. 43, No. 3, Elsevier Science Publishers B.V., Amsterdam, NL.

Nick P.R. Nieland et al.; "Structural Determinants of Opioid Activity in Derivatives of 14-Aminomorphinones: Effect of Substitution in the Aromatic Ring of Cinnamoylaminomorphinones and Codeinones"; Journal of Medicinal Chemistry, vol. 49, No. 17, 2006, pp. 5333-5338.

David Rennison et al.; "Structural Determinants of Opioid Activity in Derivatives of 14-Aminomorphinones: Effect of Changes to the Chain Linking of the C14-Amino Group to the Aryl Ring"; Journal of Medicinal Chemistry, vol. 49, No. 20, 2006, pp. 6104-6110.

Danxin Wang et al.; "Different Effects of Opioid Antagonists on μ-, σ-, and κ-Opioid Receptors with and without Agonist Pretreatment", The Journal of Pharmacology and Experimental Therapeutics, vol. 321, No. 2, 2007, pp. 544-552.

Kirsten M. Raehal et al.; "In Vivo Characteristics of 6β-Naltrexol, an Opioid Ligand with Less Inverse Agonist Activity Compared with Naltrexone and Naloxone in Opioid-Dependent Mice", The Journal of Pharmacology and Experimental Therapeutics, vol. 313, No. 3, 2005, pp. 1150-1162.

* cited by examiner

*Primary Examiner* — Charanjit Aulakh
(74) *Attorney, Agent, or Firm* — Whitham, Curtis, Christofferson & Cook, PC

(57) ABSTRACT

Selective, non-peptide antagonists of the mu opioid receptor (MOR) and methods of their use are provided. The antagonists may be used, for example, to identify MOR agonists in competitive binding assays, and to treat conditions related to addiction in which MOR is involved, e.g. heroin, prescription drug and alcohol addiction.

5 Claims, 19 Drawing Sheets

NON-PEPTIDYL, POTENT, AND SELECTIVE MU OPIOID RECEPTOR ANTAGONISTS

This application is a 371 of PCT/US10/21157 filed on Jan. 15, 1010 which claims benefit of 61/145,379 filed on Jan. 16, 2009

This invention was made with support in part from a grant from the National Institutes of Health (NIH # DA024022), and the U.S. Government may have certain rights in the invention.

BACKGROUND OF THE INVENTION

1. Field of the Invention

The invention generally relates to selective, non-peptide antagonists of the mu opioid receptor (MOR) and methods of their use.

2. Background of the Invention

Opioid dependence is one of the most serious chronic and relapsing medical disorders. Heroin and prescription opioid abuse and dependence are very common and still increasing. According to the National Household Survey on Drug Abuse 2001, there are about 800,000 persons addicted to heroin and 3.5 million prescription opioid abusers in the United States. It has been proved that for many clinically available opiates, not only their analgesic function but also their notorious side effects (such as addiction and abuse liability) are primarily due to their interaction with the mu opioid receptor (MOR). There is an ongoing need to develop selective antagonists for MOR as chemical probes to characterize the mu opioid receptor structure-function relationship, and to develop analgesics without or with less addiction and abuse liability.

SUMMARY OF THE INVENTION

The invention provides selective, non-peptide antagonists of the mu opioid receptor (MOR) and methods of using the antagonists to identity MOR agonists, or as agents to treat various disorders that involve MOR (e.g. drug addiction).

In one embodiment, the invention provides selective, non-peptide mu opioid receptor (MOR) antagonists with a general formula

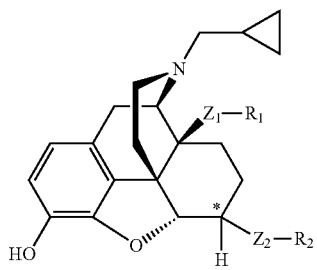

where Z1 and Z2 are spacer elements which may be present or absent and are selected from: an aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O; and wherein one or both of Z1 and Z2 and one or both of R1 and R2 are present, with the proviso that the Z1 and Z2 spacer elements may be present or absent; and where R1 and R2 are substituted or unsubstituted aromatic or aliphatic moieties; and stereoisomers thereof. For this formula, the following caveat applies: if Z1 and R1 are absent, and if Z2=NHCO, then R2 cannot be phenyl or naphthalene.

In some embodiments, the non-peptide MOR antagonist is represented by formula

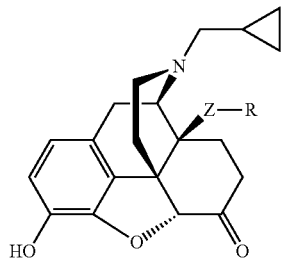

where spacer element Z may be present or absent and is selected from aliphatic (e.g. short aliphatic chain (CH$_2$)n where n=1-5); NH; CO; (NHCO)n where n=1-5; (CONH)n where n=1-5; (NHCO)(CH$_2$)n(NHCO), where n=1-5; (CONH)(CH$_2$)n(CONH), where n=1-5; (NHCO)(CH$_2$)n where n=1-5; (CONH)(CH$_2$)n where n=1-5; (CH$_2$)n(NHCO), where n=1-5; (CH$_2$)n(CONH), where n=1-5; O; CxHy (x=1-5, y=0-10).

In other embodiments, the selective, non-peptide MOR antagonist is represented by formula

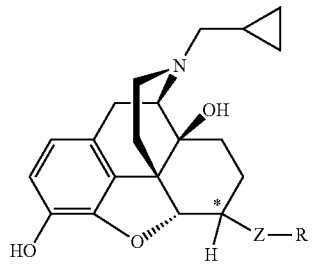

where spacer element Z may be present or absent and is selected from the group consisting of an aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O; and where R is a substituted or unsubstituted aromatic or aliphatic moiety; and stereoisomers thereof; with the caveat that if Z=NHCO, then R cannot be phenyl or naphthalene.

In yet other embodiments, the non-peptide MOR antagonist is represented by formula

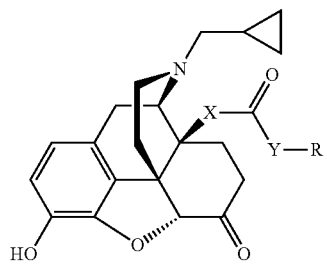

where X=O or NH; and Y may be present or absent and if present, is an aliphatic moiety; and where R is a substituted or unsubstituted aromatic or aliphatic moiety.

In further embodiments, the non-peptide MOR antagonist is represented by formula

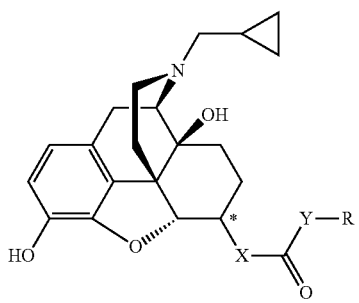

where X=O or NH; and Y may be present or absent and if present, is an aliphatic moiety; and where R is a substituted or unsubstituted aromatic or aliphatic moiety; and stereoisomers thereof; with the caveat that if X=NH and Y is absent, then R cannot be phenyl or naphthalene.

Further embodiments of the non-peptide MOR antagonist include

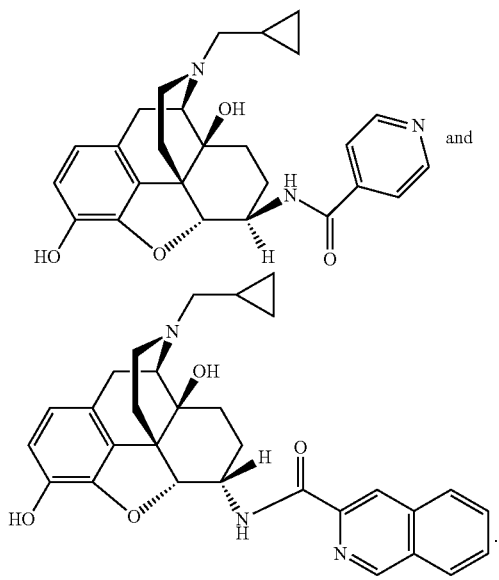

In some embodiments of the invention, the substituted or unsubstituted aromatic moieties are selected from the group which includes but is not limited to

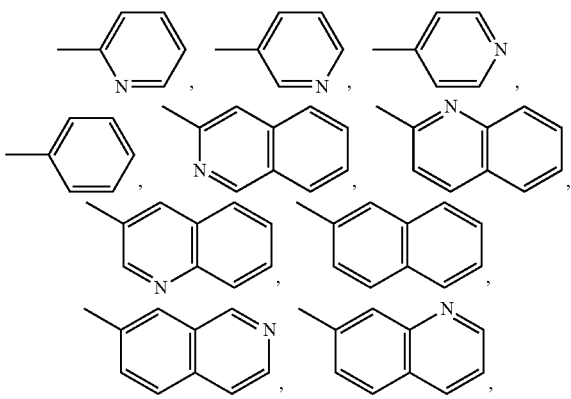

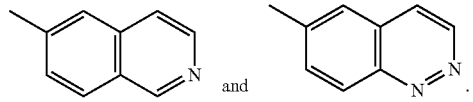

The invention further provides a method of testing whether or not a candidate compound is a MOR angonist. The method comprises the step of conducting competitive inhibition tests between the candidate compound and a MOR antagonist of general formula

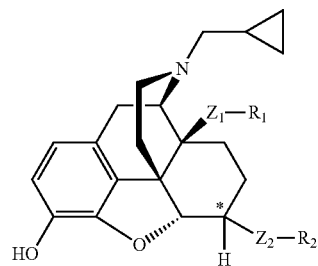

where Z1 and Z2 are spacer elements and may be present or absent and are selected from: an aliphatic moiety; NH; CO; (NHCO)n where, n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O; wherein one or both of Z1 and Z2 and one or both of R1 and R2 are present, with the proviso that the Z1 and Z2 spacer elements may be present or absent; and where R1 and R2 are substituted or unsubstituted aromatic or aliphatic moieties; and stereoisomers thereof.

In other embodiments, the invention provides a method of treating symptoms of addiction related to MOR in a patient in need thereof, the method comprising administering to the patient a MOR antagonist of general formula

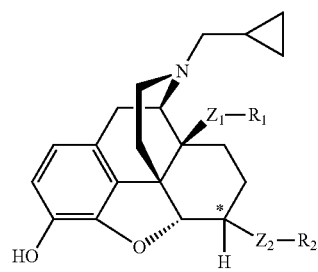

where Z1 and Z2 are spacer elements and may be present or absent and are selected from: an aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O; wherein one or both of Z1 and Z2 and one or both of R1 and R2 are present, with the proviso that the Z1 and Z2 spacer elements may be present or absent; and where R1 and R2 are substituted or unsubstituted aromatic or aliphatic moieties; and stereoisomers thereof.

BRIEF DESCRIPTION OF THE DRAWINGS

FIGS. 10A and B The docking of compounds 6 and 9 in the mu opioid receptor model. The ligands and the amino acid residues are in stick. The receptor homology models are in ribbon. A) Lead 6 and B) lead 9 in MOR.

DETAILED DESCRIPTION

Figure 1:
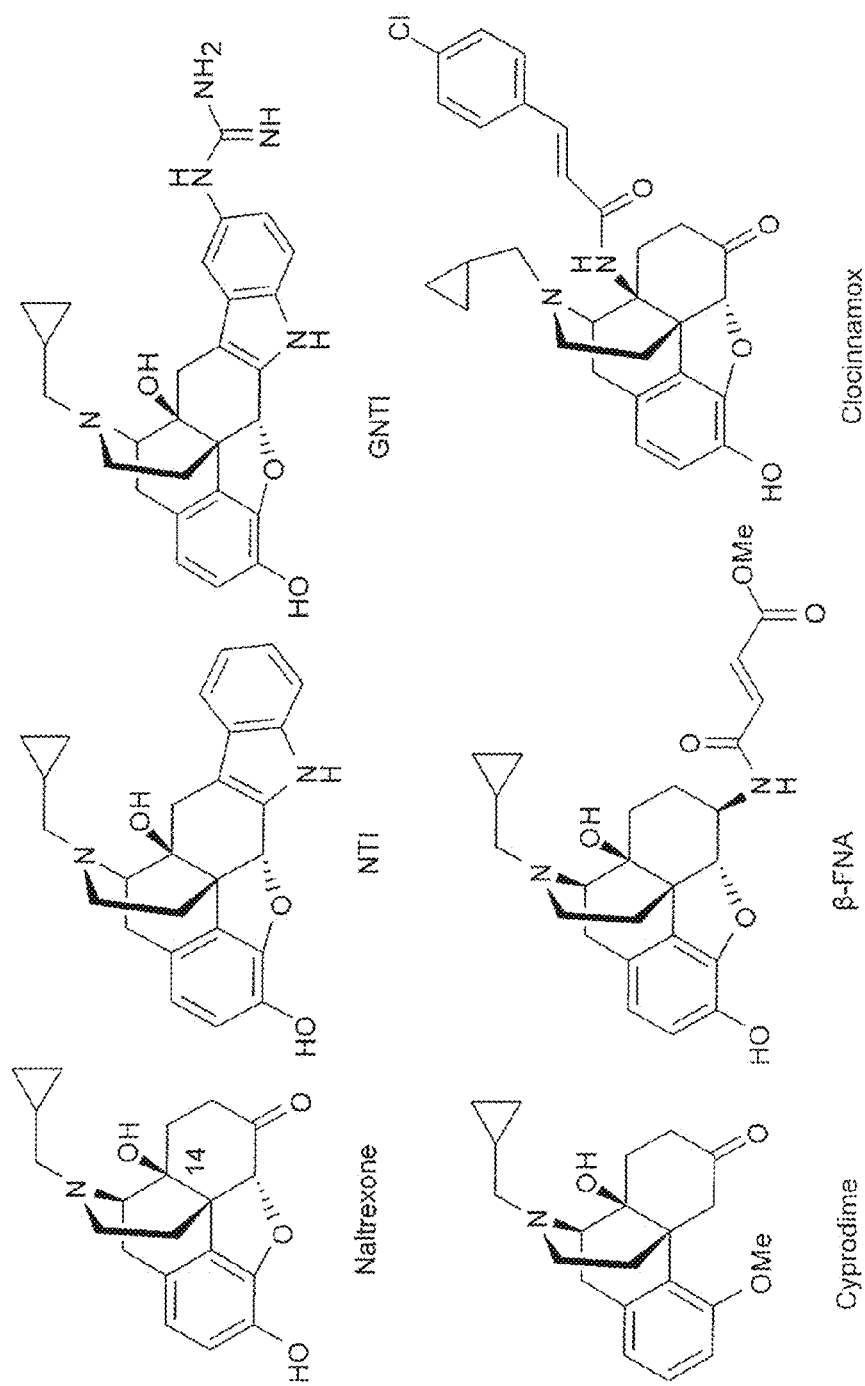
FIG. 1. Morphinan derivatives as opioid selective antagonists

The present invention provides novel non-peptide selective mu opioid receptor (MOR) antagonists. The molecules display high affinity for MOR and, because they do not include amino acids, they are relatively stable in vivo. The ligands carry structural features that enable them to interact with the aromatic binding locus built by the amino acid residues which form the extracellular part of MOR, and may also satisfy hydrogen binding requirements from the binding locus. The molecules will find use in methods for identifying MOR agonists. In addition, the molecules themselves may be used to treat addiction symptoms, such as heroin or prescription opioid drug addiction.

In some embodiments of the invention, then the compounds are C-14 substituted compounds represented by Formula 1:

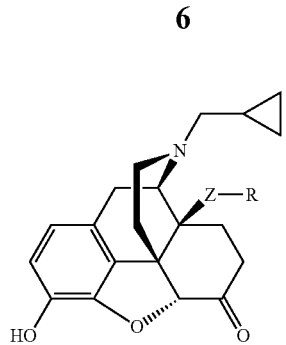

Formula 1 where Z is a spacer element and R is an aromatic or aliphatic moiety, which may be substituted or unsubstituted. Z may be present or absent. If Z is present, Z may be: aliphatic (e.g. short aliphatic chain $(CH_2)n$ where $n=1-5$); NH; CO; $(NHCO)n$ where $n=1-5$; $(CONH)n$ where $n=1-5$; $(NHCO)(CH_2)n(NHCO)$, where $n=1-5$; $(CONH)(CH_2)n(CONH)$, where $n=1-5$; $(NHCO)(CH_2)n$ where $n=1-5$; $(CONH)(CH_2)n$ where $n=1-5$; $(CH_2)n(NHCO)$, where $n=1-5$; $(CH_2)n(CONH)$, where $n=1-5$; O (in which case Z is a single atom); $CxHy$ ($x=1-5$, $y=0-10$).

Examples of unsubstituted aromatic moieties that may be R include but are not limited to phenyl or naphthalene. The aromatic substitutent R may be a substituted aromatic (i.e. a heteroaromatic) and may be substituted at one or more positions, either within the ring, or bonded or attached to the ring. Aromatic ring sizes (i.e. number of carbon atoms in the ring) are generally in the range of from about 3 to about 6.

Exemplary moieties that may be included in the aromatic ring(s) include but are not limited to N, methyl and various branched and unbranched aliphatic chains; COOH, halogen, CN, $NO_2$, $OCH_3$, etc., and combinations thereof, e.g. $(CH_2)nCOOH$ where $n=1-5$), $(CH_2)nNO_2$ where $n=1-5$, $(CH_2)nNH_2$ where $n=1-5$, etc. If multiple substitutions are present, they may be the same or different.

Examples of aliphatic moiety that may be R include but are not limited to various branched and unbranched aliphatic chains and various sizes and numbers of aliphatic rings (e.g. various sizes of cycloalkanes). The chains or rings can also be substituted with different types of heteroatoms, including but not limited to N, S, P, O, etc. Aliphatic ring sizes (i.e. number of carbon atoms in the ring) are generally in the range of from about 3 to about 6. Rings may contain one or more double bonds, and may be substituted (i.e. may be heterocyclic rings) or branched (i.e. may have various substitutions attached to the ring system).

In some embodiments of the invention, the compounds are C-6 substituted compounds represented by Formula 2:

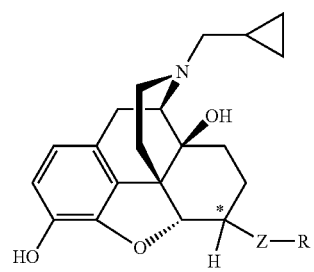

Formula 2 where Z is a spacer element; R is an aromatic or aliphatic moiety (as described for Formula 1), which may be substituted or unsubstituted; and * indicates a chiral carbon. The invention encompasses all stereoisomers (e.g. α and β isomers) of C6. In this embodiment, Z may be present or absent. If Z is present, Z may be: aliphatic (e.g. short aliphatic chain $(CH_2)n$ where n=1-5); NH; CO; (NHCO)n where n=1-5; (CONH)n where n=1-5; (NHCO)$(CH_2)$n(NHCO), where n=1-5; (CONH)$(CH_2)$n(CONH), where n=1-5; (NHCO)$(CH_2)$n where n=1-5; (CONH)$(CH_2)$n where n=1-5; $(CH_2)$n (NHCO), where n=1-5; $(CH_2)$n(CONH), where n=1-5; O (in which case Z is a single atom), CxHy (x=1-5, y=0-10), etc; with the caveat that if Z=NHCO, then R cannot be phenyl or naphthalene.

Examples of unsubstituted aromatic moieties that may be R include but are not limited to phenyl, naphthalene, and other aromatic moieties. The aromatic substitutent R may be a substituted aromatic (i.e. a heteroaromatic) and may be substituted at one or more positions, either within the ring, or bonded or attached to the ring. Exemplary moieties that may be included in the aromatic ring(s) include but are not limited to N, methyl and various branched and unbranched aliphatic chains; COOH, halogen, CN, $NO_2$, $OCH_3$, etc., and combinations thereof, e.g. $(CH_2)$nCOOH where n=1-5), $(CH_2)$n$NO_2$ where n=1-5, $(CH_2)$n$NH_2$ where n=1-5, etc. If multiple substitutions are present, they may be the same or different.

Examples of aliphatic moiety that may be R include but are not limited to various branched and unbranched aliphatic chains and various sizes of aliphatic rings (e.g. cycloalkanes). The chains or rings can also be substituted with different type of heteroatoms, including but not limited to N, S, P, O, etc., or as described for the aromatic rings, or branched (e.g. may have various substitutions attached to the ring system).

For Formulas 1, 2 and 3 (below), aromatic and aliphatic ring sizes (i.e. the number of carbon atoms in the ring) are generally in the range of from about 3 to about 6, and R may be a single ring or may contain two or more (generally from about 2 to about 5, e.g. 2, 3, 4, or 5) fused rings. Aliphatic rings may contain one or more double bonds, and may be substituted at one or more positions, either by substituting a constituent of the ring (i.e. the rings may be heterocylic rings), or by attaching a modifying chemical group to the ring (e.g. may have various substitutions attached to the ring system).

In yet further embodiments of the invention, the compounds are substituted at both the C6 and C14 positions, as depicted in Formula 3:

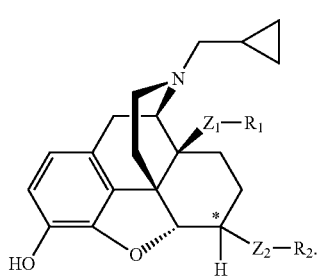

Formula 3

In Formula 3, Z1 and Z2 may be the same or different and R1 and R2 may also be the same or different (i.e. all these groups may vary independently). Possible equivalents for Z1 and Z2 are the same as those listed for Z of Formulas 1 and 2, and, as noted above, may the spacers Z1 and Z2 may be present or absent. Possible equivalents for R1 and R2 are the same as those listed for R of Formulas 1 and 2. All stereoisomers of the compound represented by Formula 3 are also contemplated. For this formula, the following caveat applies: if Z1 and R1 are absent, and if Z2=NHCO, then R2 cannot be phenyl or naphthalene.

In some embodiments of the invention, the compounds substituted at C14 may also be represented as in Formula 4:

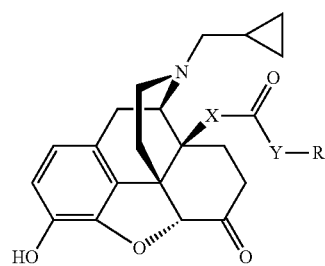

Formula 4 where X=O or NH; Y=an aliphatic moiety, or, in some embodiments, absent; and R is defined as for Formula 1.

Examples of suitable aliphatic moieties that may be Y include but are not limited to unbranched aliphatic moieties such as $(CH_2)$n, where n ranges from about 0 to about 10. For example, n may be 0 (i.e. Y is absent), or n may be 1, 2, 3, 4, 5, or more, and is preferably 0, 1, 2 or 3. Other possible Y equivalents include but are not limited to CxHy (x=1-5, y=0-10).

With respect to Formula 4, when X=O, the resulting compound is represented as in Formula 5:

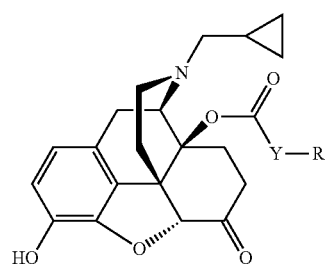

Formula 5 and when X=NH, the compounds are represented as in Formula 6:

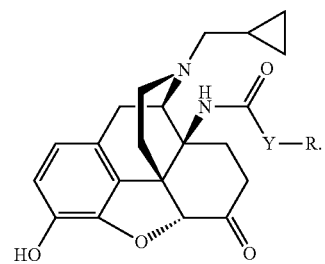

Formula 6

For Formulas 5 and 6, Y and R are as represented in Formula 4.

In some embodiments of the invention, the compounds substituted at C6 may be represented as in Formula 7:

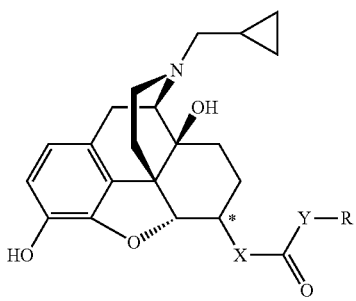

Formula 7 where X=O or NH; Y=an aliphatic moiety (as defined for Formula 4 above), or, in some embodiments, absent; and R is defined as for Formula 2, with the caveat that if X=NH and Y is absent, then R cannot be phenyl or naphthalene.

With respect to Formula 7, when X=O, the compounds may be represented as in Formula 8:

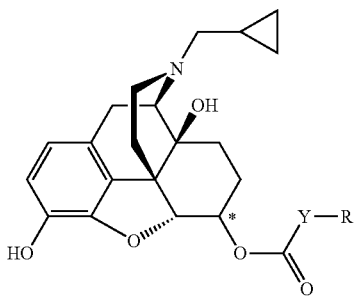

Formula 8 and when X=NH, they are represented as in Formula 9:

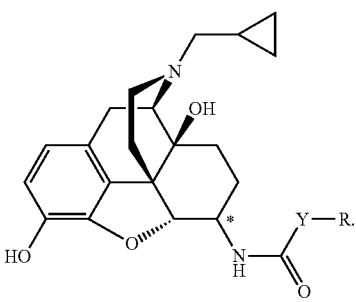

Formula 9

For Formulas 8 and 9, Y and R are as described for Formula 7. For Formula 9, if Y is absent, then R cannot be phenyl or naphthalene.

In some embodiments of the invention, the R group is phenyl or naphthalene or a substituted phenyl or naphthalene (for example, N substituted phenyl or naphthalene, as follows:

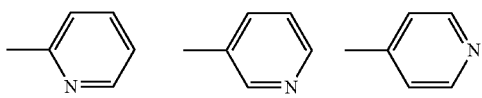

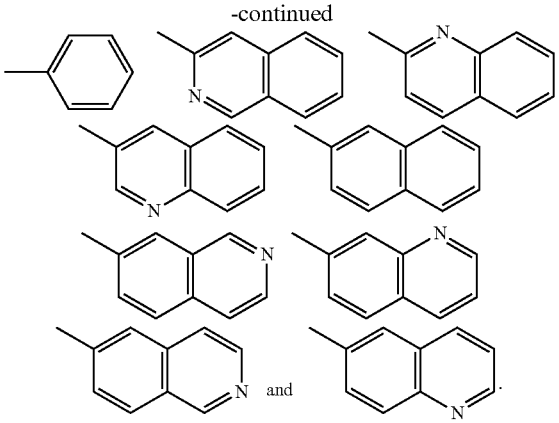

Particular embodiments of the compounds of the invention include:

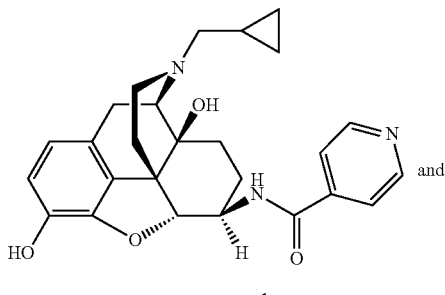

6 and

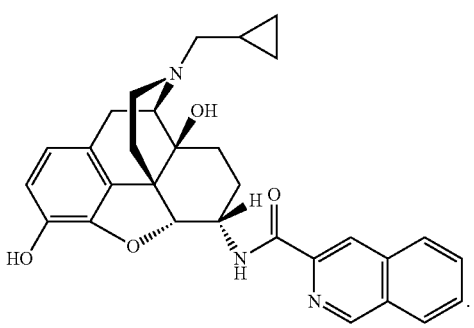

9

The compounds of the invention display selectivity for MOR in comparison to other receptors, e.g. other related receptors of interest such as one or both or DOR and KOR. By "selective" or "selectivity" we mean that the compounds of the invention display at least a 10-fold greater binding affinity for MOR than for one or more other receptors (at least one other receptor) of interest. In some cases, the compounds display binding affinities that are about 10, about 50, about 100, about 500 or about 1000-fold or greater for MOR than for other receptors, as measured by standard techniques that are known to those of skill in the art, and described, for example, in the Examples section herein. Further, in some embodiments, the antagonists may be used to identify or characterize other receptors as well.

The compounds of the invention are generally MOR antagonists. By "antagonist" we mean a receptor ligand that does not provoke a biological response upon binding to a receptor, but which blocks or dampens (decreases, lessens, etc.) agonist-mediated responses. (An "agonist" is a ligand that binds to a receptor and triggers a response, i.e. an agonist produces an action, often mimicking the action of a naturally occurring substance.) Antagonists thus have affinity but no efficacy for their cognate receptors, and binding of an antagonist to a receptor will disrupt the interaction and inhibit the function of an agonist or inverse agonist at receptors. Antagonist activity may be reversible or irreversible depending on the longevity of the antagonist-receptor complex, which, in turn, depends on the nature of antagonist receptor binding.

The MOR opioid antagonists of the invention have a variety of applications. For example, they may be used in competitive assays to identify MOR agonists. MOR agonists are, in fact, defined as opoid agonists only if their effect is competitively inhibited by a known opioid antagonist. The application thus provides methods of identifying a substance as a MOR opioid agonist by analyzing the results of competitive binding assays. Those of skill in the art are familiar with such competition experiments, which are typically carried out under controlled conditions in the absence of antagonist (to establish a baseline of binding by the possible agonist) and also in the presence of antagonist at a variety of concentrations of antagonist while the concentration of candidate agonist is held constant. Levels of binding of the candidate agonist in the absence of the antagonist and at increasing concentrations of antagonist are measured by any suitable means, and may be measured directly or indirectly. If the presence of the antagonist interferes with (inhibits) the binding of the test substance to the receptor (i.e. if the presence of antagonist prevents or decreases binding of the test substance to the receptor), then the substance being tested is deemed to be a receptor agonist. Variations of competitive assays, the mathematical and statistical analysis of results obtained in this manner, and the interpretation of such analyses, are well known.

Further testing of the compounds of the invention may reveal agonist activity on the part of one or more compounds, in which case the compounds may be used and administered as agonists or partial agonists of MOR.

In some embodiments of the invention, the selective antagonists of the invention may be used, for example, in medical applications. For example, the antagonists of the invention may be administered to a subject or patient in need of treatment for addictions that involve the MOR receptor, such as drug and alcohol addictions. MOR is the receptor that is accessed by heroin and by several other opioids (e.g. commercial or prescription opioids such as morphine, oxycodone, oxymophone, etc.). Other naturally occurring opiates and semi-synthetic opoids also access this receptor Several such substances are known and patients to whom they are prescribed and/or more frequently subjects who obtain them illegally for recreational use are liable to become addicted, and to exhibit symptoms of addiction. Symptoms of addiction which may be lessened or treated by the administration of the antagonists of the invention include but are not limited to craving for the addictive substance, physical and psychological dependence, CNS-mediated respiration depression, dysphoria, sweating, nausea, rhinorrea, depression, severe fatigue, vomiting and pain, insomnia, etc. The MOR selective antagonists of the invention may be used to treat such addictions, e.g. to lessen or alleviate symptoms of withdrawal, e.g. during addiction treatment.

In addition, the MOR antagonists of the invention may be used to treat conditions such as pain, neuropathic pain, alcoholism, cocaine addiction, Parkinson's disease, gambling addiction, obesity, epilepsy, depression, schizophrenia, bipolar disorder, schizoaffective disorder, inflammation, gastrointestinal tract disturbance, AIDS, etc.

The invention thus also provides compositions and formulations comprising the antagonists. The compositions include one or more substantially purified antagonists and a pharmacologically suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of antagonist in the formulations may vary. However, in general, the amount in the formulations will be from about 1 to about 99%.

The antagonist compositions (preparations) of the present invention may be administered by any of the many suitable means which are well known to those of skill in the art, including but not limited to by injection, inhalation, orally, intranasally, by ingestion of a food product containing the antagonist, topically, as eye drops, via sprays, etc. In preferred embodiments, the mode of administration is orally or by injection. In addition, the compositions may be administered in conjunction with other treatment modalities such as other medicaments, other types of therapy (e.g. psychological or psychiatric treatment), and the like.

The amount of antagonist that is administered to an individual (who is usually a mammal, typically a human) will vary based on several factors, as will be understood by those of skill in the art. For example, the dose and frequency of administration may vary according to the gender, age, weight, general physical condition, ethnic background, etc. of the individual, as well as whether or not the individual has other diseases or conditions that might impinge on the treatment. Generally, the dose will be in the range of from about 0.01 to about 100 mg/kg of body weight.

The ensuing Examples are intended to further illustrate the present invention, but should not be interpreted as limiting in any way.

EXAMPLES

Example 1

14-O-Heterocyclic-Substituted Naltrexone Derivatives as Non-Peptide Mu Opioid Receptor Selective Antagonists: Design, Synthesis and Biological Studies Abstract: Mu opioid receptor antagonists have clinical utility and are important research tools. In order to develop non-peptide and highly selective mu opioid receptor antagonist, a series of 14-O-heterocyclic substituted naltrexone derivatives were designed, synthesized and evaluated. These compounds showed subnanomolar to nanomolar binding affinity for the mu opioid receptor. Among them, compound 1 exhibited the highest selectivity for the mu opioid receptor over the delta and kappa receptors. These results implicated an alternative "address" domain in the extracellular loops of the mu opioid receptor.

Opioid receptors were generally classified into three subtypes based on the pharmacological, behavioral, and biochemical studies.[1-3] Opioid antagonists have played very important roles in the study of opioid receptors. In fact, an agonist is characterized as opioid-receptor-mediated only if its effect is competitively inhibited by an opioid antagonist.[4,5] It is important to have receptor-selective opioid antagonists as tools to identify the receptor types related to the interaction with opioid agonists.[4-6] The mu opioid receptor (MOR) is the major type that mediates opioid analgesic effects of morphine, although all three opioid receptors can be involved in analgesia. The characterization of the MOR structure-function relationship is essential because it has been found that morphine's analgesic effect, addictive properties, and other major side effects are abolished in MOR knock-out mice.[7,8] Moreover, it has been demonstrated that the analgesic effects and the adverse side effects (including addiction and abuse liability) of morphine are primarily due to its interaction with the MOR.4 In fact, naltrexone, an opioid antagonist with moderate selectivity for the MOR, has been shown to block relapse and curb drug craving in post-dependent opiate addicts.[9,10] Recent research results also indicate that MOR antagonists can be used in the treatment of obesity, psychosis and Parkinson's disease.[11] Furthermore, highly selective MOR antagonists can be used as probes to characterize the MOR binding pocket. Yet the lack of a non-peptidyl, highly selective, and potent MOR antagonist limits our understanding of the structure-function relationship of the MOR, the interaction of non-peptidyl MOR agonists with the receptor, and more specifically, the activation mechanism of the receptor related to its role in drug abuse and addiction.

Schwyzer et al proposed the "message-address" concept in his analysis of the structure-activity relationship of ACTH, adrenocorticotropic hormone, and related honnones.12 By applying the "message-address" concept, highly selective non-peptide antagonists for the kappa opioid receptor (KOR) (e.g. norbinaltorphimine (norBNI) and 5'-guanidinonaltrindole (GNTI)),[13,14] and for the delta opioid receptor (DOR) (e.g. naltrindole (NTI))[15] were designed and synthesized several years ago. (FIG. 1) Thus far no potent and highly selective antagonist derived from morphinan's structural skeleton has been developed for the MOR, although some moderately potent ligands, e.g. cyprodime,[16] are available. Compared with the high selectivity of GNTI for the KOR (Ki value ratios are mu/kappa≈120, delta/kappa≈250)[14] and NTI for the DOR (Ki value ratios are mu/delta≈152, kappa/delta≈276),[15] cyprodime only has a moderate selectivity for the MOR over the DOR and KOR (Ki value ratios are kappa/mu≈45, delta/mu≈40).[17] At the same time, β-funaltrexamine (β-FNA), clocinnamox, and other compounds, act as selective but irreversible antagonists for the MOR.[18] Therefore the development of a highly selective, non-peptidyl, and reversible MOR antagonist is highly desired.

It was reported that the extracellular loop (EL) domains of the MOR are critical for the binding of MOR selective agonists, such as morphine, sufentanil, lofentanil and DAMGO.[19] At the same time, site-directed mutagenesis studies have revealed that certain amino acid residues in this domain may be essential for ligand (including agonist and antagonist) selectivity for the MOR over the other two opioid receptor types.[20] Therefore, a non-peptide ligand with potential interaction with the EL domains of the MOR, would be favorable for its selectivity for the MOR.

Due to the lack of the crystal structure of the MOR, so far most molecular design efforts directed toward development of selective opioid ligands have been based on structure-activity-relationship studies. As a matter of fact, in the entire superfamily of GPCRs, only the X-ray crystal structures of bovine rhodopsin,[21-24] opsin,[25] and the human β 2-[26-29] and β 1-adrenergic receptor[30] have been successfully obtained with high resolution. Thus far, most of the molecular models of other GPCRs have been constructed using rhodopsin's structure as a template via homology modeling. Homology modeling of GPCRs has been successfully applied to further understand ligand-protein interactions, and to identify new and potent ligands. It is believed that with all the lessons learned from previous experience, GPCR homology modeling based on the bovine rhodopsin X-ray crystal structure can aid in structure-based drug design and virtual screening for therapeutic applications.[31-38] For example, a homology model of the Angiotensin II Type 1 (AT1) receptor was used to further explore the binding sites of several non-peptide AT1 receptor antagonists.[39] A homology model of the M1 muscarinic acetylcholine receptor was applied to understand the mechanism by which the agonist-receptor complex activates G proteins.[40]

Figure 2:
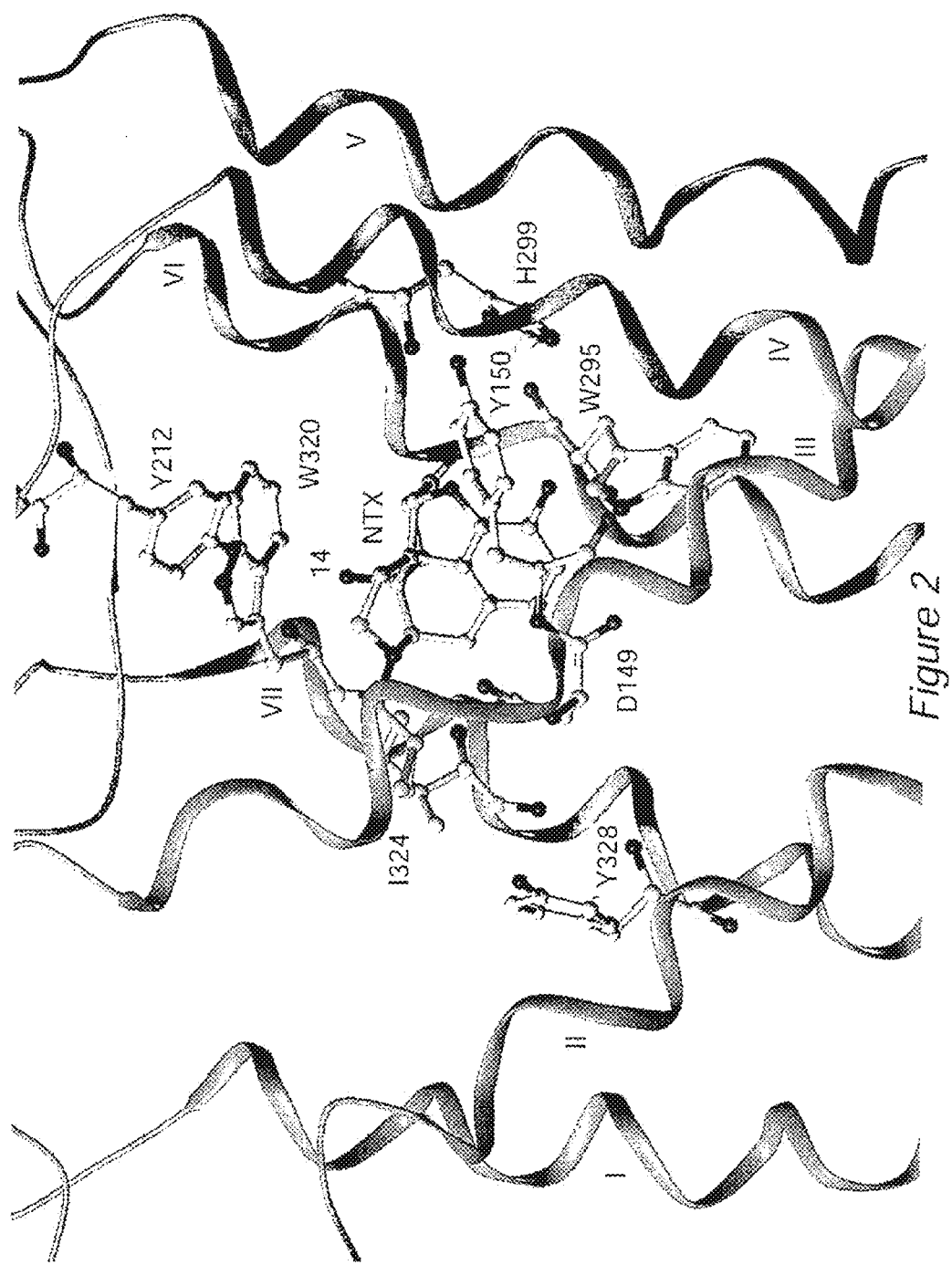
FIG. 2. Naltrexone in MOR Binding pocket: Mu opioid receptor model: ribbon=the residues in mu opioid receptor: ball and stick=Naltrexone molecule.

Recently, we reported the construction of a MOR homology model based on the crystal structure of bovine rhodopsin.[41] This model contained not only the transmembrane helical domains, but also the extracellular and intracellular loops so that the model we obtained was integrated and complete. This model was further optimized in a membrane-aqueous system by molecular dynamics simulations. Similar homology models of the DOR and KOR were then constructed (see supplementary information for details). Naltrexone is an ideal template for the design of selective MOR antagonists, because it has subnanomolar to nanomolar affinity for all three opioid receptor types and shows moderate selectivity for the MOR over the other two opioid receptor types. FIG. 2 shows that in a representative binding mode of naltrexone in the MOR, the 14-hydroxyl group of naltrexone is pointing to the EL3 loop and the upper-level region of TM6/7. Compared to the amino acid residues in the corresponding domains of the KOR and DOR, some non-conserved residues, e.g. Tyr212 and Trp320, in MOR could act as hydrogen bonding donor/acceptors. This unique feature in the MOR antagonist binding locus might form an alternative "address" domain to differentiate the antagonist binding mode of the MOR over the DOR and KOR. Therefore, a new compound containing specific structural features to interact with these amino acid residues might have increased selectivity for the MOR over the DOR and KOR.

Figure 3:
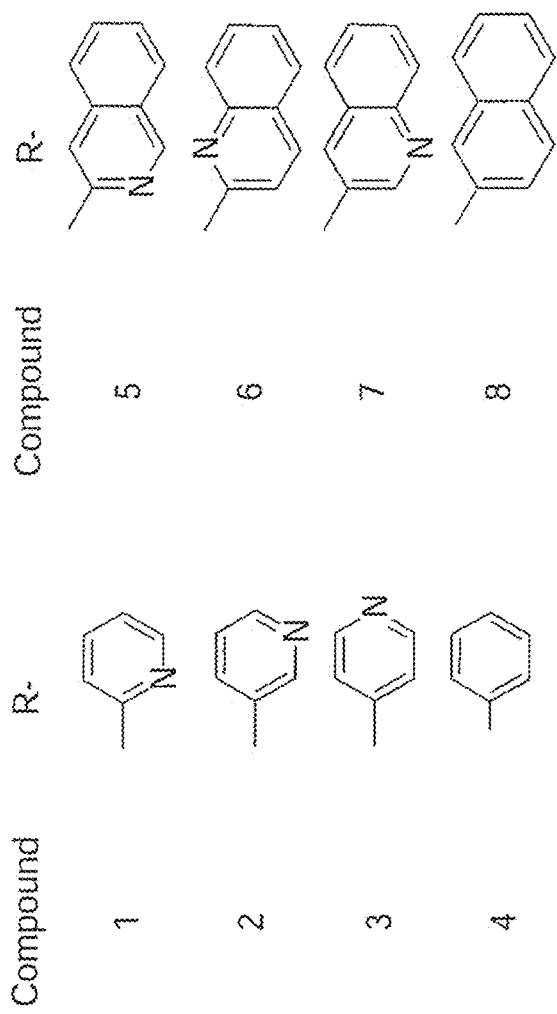
FIG. 3. The designed ligand for primary study.
Figure 3:
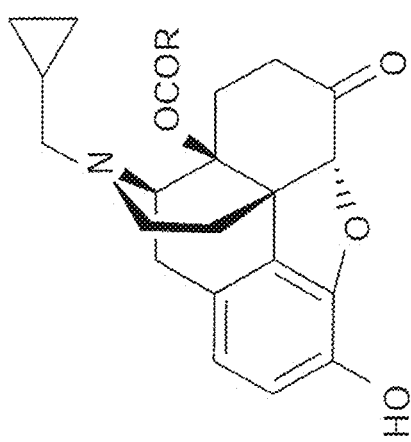

Based on this hypothesis, a series of novel 14-O-substituted naltrexone derivatives (FIG. 3) have been designed and synthesized. The ester bond in these novel ligands was assumed to provide a flexible conformation for the whole side chain. The nitrogen atom in the hetero-aromatic moiety on the 14-O-position of naltrexone was introduced to provide an opportunity for hydrogen bonding and/or aromatic stacking interaction with the amino acid residues Tyr212 and Trp320 in the MOR binding pocket (compound 1-3 and 5-7). Compound 4 and 8 were designed as control compounds to test this hypothesis. These ligands could also be considered as derivatives of clocinnamox without the Michael acceptor character.

Figure 4:
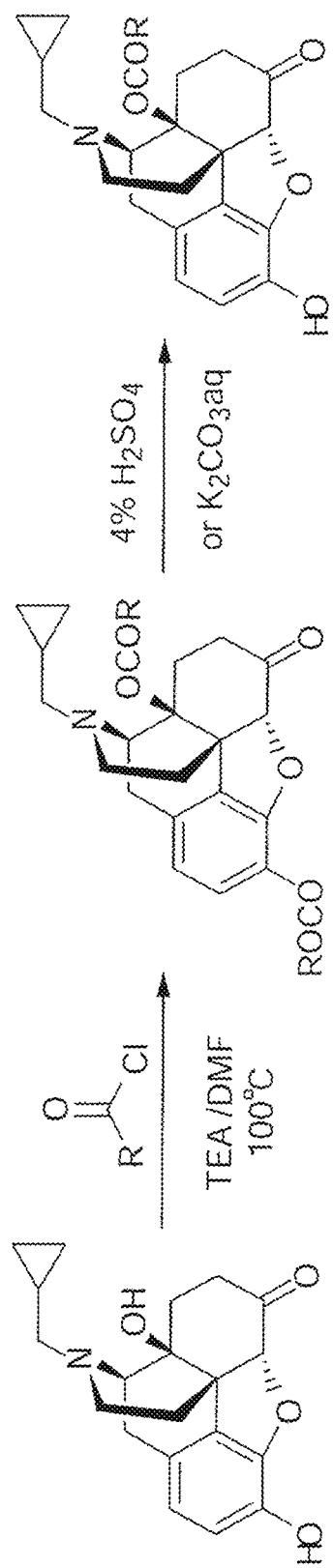
FIG. 4. The synthetic route for the 14-O-substituted naltrexone derivatives.

Using naltrexone as the starting material, the syntheses of these 14-O-heterocyclic substituted derivatives was straightforward (FIG. 4). To be noticed, in the second step of the synthesis route, $K_2CO_3$ aqueous solution was used to prepare the control compounds 4 and 8 instead of using the acidic condition. All the final compounds were obtained with reasonable yield and characterized with NMR, IR, MS, and HPLC (See supplementary information). The primary biological studies of these ligands included competitive radioligand-binding assays using mono-cloned opioid receptors expressed in CHO cell lines. [$^3$H]DAMGO, [$^3$H] NTI and [$^3$H] norBNI were used to label the MOR, DOR and KOR respectively. The binding affinities of these ligands for the MOR, DOR and KOR, and comparative selectivities were summarized in Table 1. These compounds showed binding affinities in the subnanomolar to nanomolar range for the MOR.

It has been reported by Schmidhammer et al., that 14-alkoxymorphinans showed very high opioid receptor affinity. These compounds exhibited significantly increased binding affinities at all opioid receptors without any specific preference for any one receptor type.[42-44] Recently, Husbands et al. investigated the SAR of the analogs of clocinnamox, 14-aminodihydromorphinones and 14-aminodihydrocodeinones, in order to explore the effect of changing the chain linking and substitution in the aromatic ring of cinnamoylaminomorphinones and codeinones.[45-47] These authors found that a modest selectivity for the MOR over the

TABLE 1

Binding affinity and functional assay results for the 14-O-substituted naltrexone derivatives.

| | Ki ± SEM(nM) | | | Selectivity | | Percent Max of |
|---|---|---|---|---|---|---|
| Compounds | [$^3$H]DAMGO (μ) | [$^3$H] NTI (δ) | [$^3$H] norBNI (κ) | δ/μ | κ/μ | DAMGO |
| Naltrexone | 0.26 ± 0.02 | 117.00 ± 8.90 | 5.15 ± 0.26 | 450 | 20 | 0.00 |
| β-FNA | 0.41 ± 0.04 | 27.78 ± 4.60 | 0.94 ± 0.05 | 68 | 2 | 0.00 |
| CTAP | 2.02 ± 0.71 | 1441.00 ± 106.10 | 1012.70 ± 174.80 | 713 | 501 | 0.00 |
| 1 | 0.14 ± 0.03 | 117.38 ± 17.97 | 25.50 ± 6.50 | 838 | 182 | 0.00 |
| 2 | 1.59 ± 0.61 | 170.30 ± 12.64 | 47.81 ± 8.48 | 107 | 30 | 0.00 |
| 3 | 5.58 ± 1.34 | 405.32 ± 234.68 | 49.21 ± 20.37 | 73 | 9 | 0.00 |
| 4 | 123.23 ± 38.23 | >10,000.00 | 586.42 ± 32.39 | >81 | 5 | 0.00 |
| 5 | 68.40 ± 6.04 | >10,000.00 | >10,000.00 | >146 | >146 | 0.00 |
| 6 | 1.44 ± 0.32 | 22.81 ± 19.52 | 67.15 ± 36.72 | 16 | 47 | 0.00 |
| 7 | 2.69 ± 0.72 | 818.43 ± 507.23 | 148.23 ± 55.53 | 304 | 55 | 22.00 ± 10.30 |
| 8 | 225.27 ± 46.6 | 907.18 ± 192.99 | 46.57 ± 13.53 | 4 | <1 | 0.00 |

The Ki values for the mu, delta and kappa opioid receptors were n = 3. The averages are reported along with their standard error of the means, SEM, for each compound. The comparison to percent stimulation of DAMGO was the Emax of the compound compared to the Emax of DAMGO (normalized to 100%). The DAMGO EC$_{50}$ value was 45.1 ± 6.63 nM and its Emax value was 366 ± 23% stimulation over basal using a [$^{35}$S] GTPγS functional assay. Naltrexone, β-FNA and CTAP were tested along as positive controls under the same conditions.

Also as shown above, all of these compounds exhibited different levels of selectivity for the MOR over the KOR and DOR. Among these, compound 1 had approximately 800-fold selectivity for the MOR over the DOR and nearly 200-fold selectivity over the KOR. Compound also showed over 100-fold selectivity for the MOR over the other two receptor types, although its binding affinity for the MOR was significantly lower than compound 1. In addition, all of these compounds acted as MOR antagonists in $^{35}$[S]GTPγS functional assays except for compound 7, which was a partial agonist.

Compared to the control compounds 4 and 8, the MOR selectivity over DOR and KOR had been enhanced greatly in all of the other compounds. This result suggested that the 14-O-substitutions introduced onto the naltrexone skeleton might interact with the proposed alternative "address" domain in the MOR, and the nitrogen atom in the heterocyclic ring might act as a hydrogen bond acceptor and play an important role for the selectivity. Among all of these ligands, compound 1 showed the highest selectivity, which suggested that it had the most favorable orientation of its side chain towards this plausible "address" binding domain in the MOR. For compound 5, its side chain might confer selectivity for the MOR, whereas the bulkiness of its side chain also might have reduced its binding affinity for the MOR. To further characterize compound 1 as the lead for our next generation molecular design, its antagonism was evaluated against DAMGO in $^{35}$[S]GTPγS functional assay. The concentration of compound 1 was 1.5 nM while DAMGO was in the range of 10 nM to 10,000 nM. The Ke value of compound was 0.20±0.04 nM and apparent pA2 value was 9.72±0.10. This observation was consistent with the binding affinity results and further verified that compound 1 could be used as the lead for future molecular design.

DOR and KOR was achieved when the side chain on the 14 positions was comparably rotatable in these 14-aminiodihydromorphinone compounds.

Comparing to the compounds reported by Schmidhammer and Husbands, the compounds reported here showed similar affinity for the MOR, but much higher selectivity over the DOR and KOR. One possible explanation might be that the introduction of a shorter side chain and a more flexible ester bond in our compounds might lead to a more favorable conformation and orientation of the side chain to target the "address" locus and thereby improve selectivity for the MOR. Certainly this "address" locus needs to be further verified, e.g. by site-directed mutagenesis, in future studies.

In summary, a series of 14-O-heterocyclic substituted naltrexone derivatives were designed, synthesized and evaluated as selective MOR antagonists. Most of these novel ligands exhibited subnanomolar to nanomolar binding affinity for the MOR, with compound 1 showing the highest selectivity for the MOR over the DOR and KOR. These results implicated a plausible "address" domain in the extracellular loops of the MOR. The knowledge gained from these studies will enrich the "message-address" concept that has been applied successfully in opioid research and may lead to the identification of potent MOR selective non-peptide antagonists.

REFERENCES FOR EXAMPLE 1

1. Goldstein, A.; Naidu, A. Mol. Pharmacol. 1989, 36, 265-272;
2. Dhawan, B. N.; Cesselin, F.; Raghubir, R.; Reisin, T.; Bradley, P. B.; Portoghese, P. S.; Hamon, M. Pharmacol. Rev. 1996, 48(4), 567-592;
3. Minami, M.; Satoh, M. Neurosci. Res. 1995, 23, 121-145;

4. Zimmerman, D. M.; Leander, J. D. J. Med. Chem., 1990, 33, 895-902.
5. Schmidhammer, H. Progress in Medicinal Chemistry, 1998, 35, 83-132.
6. Eguchi, M. Med. Res. Rev. 2004, 24(2), 182-212;
7. Skoubis, P. D.; Matthes, H. W.; Walwyn, W. M.; Kieffer, B. L.; Maidment, N. T. Neuroscience, 2001, 106, 757-63.
8. Matthes, H. W.; Maldonado, R.; Simonin, F.; Valverde, O.; Slowe, S.; Kitchen, I.; Befort, K.; Dierich, A.; Le Meur, M.; Dollé, P.; Tzavara, E.; Hanoune, J.; Rogues, B. P.; Kieffer, B. L. Nature, 1996, 383(6603), 819-23;
9. Gold, M. S.; Dackis, C. A.; Pottash, A. L.; Sternbach, H. H.; Annitto, W. J.; Martin, D.; Dackis, M. P. Med. Res. Rev. 1982, 2(3), 211-46;
10. Gonzalez, J. P.; Brogden, R. N. Drugs, 1988, 35, 192-213;
11. Goodman, A. J.; Le Bourdonnec, B.; Dolle, R. E. ChemMedChem, 2007, 2. 1552-1570;
12. Schwyzer, R. Ann. N.Y. Acad. Sci. 1977, 297, 3-26;
13. Portoghese, P. S.; Lipkowski, A. W.; Takemori, A. E. Life Sci. 1987, 40, 1287-92;
14. Jones, R. M.; Hjorth, S. A.; Schwartz, T. W.; Portoghese, P. S. J. Med. Chem. 1998, 41(25), 4911-4;
15. Portoghese, P. S.; Sultana, M.; Nagase, H.; Takemori, A. E. J. Med. Chem., 1988, 31, 281-82;
16. a) Schmidhammer, H.; Burkard, W. P.; Eggstin-Aeppli, L.; Smith, C. F. C. J. Med. Chem., 1989, 32, 418-421; b) Schmidhammer. H.; Smith, C. F.; Erlach, D.; Koch, M.; Krassnig, R.; Schwetz, W.; Wechner, C. J. Med. Chem. 1990, 33(4), 1200-6; c) Schmidhammer, H.; Smith, C. F.; Erlach, D.; Koch, M.; Krassnig, R.; Schwetz, W.; Wechner, C. Prog. Clin. Biol. Res. 1990, 328, 37-40. d) Spetea, M.; Schullner, F.; Moisa, R. C.; Berzetei-Gurske, I. P.; Schraml, B.; Dorfler, C.; Aceto, M. D.; Harris, L. S.; Coop, A; Schmidhammer, H. J. Med. Chem. 2004, 47(12), 3242-7;
17. Schmidhammer, H.; Burkard, W. P.; Eggstin-Aeppli, L.; Smith, C. F. C. J. Med. Chem., 1989, 32, 418-421.
18. a) Lewis, J. W.; Smith, C. F. C.; McCarthy, P. S.; Kobylecki, R. J.; Myers, M.; Haynes, A. S.; Lewis, C. J.; Waltham, K. NIDA Res. Monogr. 1988, 90, 136-143; b) Portoghese, P. S.; Takemori, A. E. NIDA Res. Monogr. 1986, 69, 157-68; c) Burke, T. F.; Woods, J. H.; Lewis, J. W.; Medzihradsky, F. J. Pharmacol. Exp. Ther. 1994, 271 (2), 715-21;
19. a) Xue, J.-C.; Chen, C.; Zhu, J.; Kunapuli, S. P.; De Riel, J. K.; Yu, L.; Liu-Chen, L-Y. J. Biol. Chem. 1995, 270(22), 12977-12979; b) Zhu, J.; Xue, J.-C.; Law, P.-Y.; Claude, P. A.; Luo, L.-Y.; Yin, J.; Chen, C.; Liu-Chen, L.-Y. FEBS Lett. 1996, 384, 198-202;
20. a) Bonner, G.; Meng, F.; Akil, H. Eur. J. Pharmcol. 2000, 403, 37-44; b) Xu, H.; Lu, Y. F.; Partilla, J. S.; Zheng, Q. X.; Wang, J. B.; Brine, G. A.; Carroll, F. I.; Rice, K. C.; Chen, K. X.; Chi, Z. Q.; Rothman, R. B. Synapse (New York), 1999, 32(1), 23-28;
21. Okada, T.; Le Trong, I.; Fox, B. A.; Behnke, C. A.; Stenkamp, R. E.; Palczewski, K. J. Struct. Biol. 2000, 130(1), 73-80;
22. Teller, D. C.; Okada, T.; Behnke, C. A.; Palczewski, K.; Stenkamp, R. E. Biochemistry. 2001, 40(26), 7761-72;
23. Salom, D.; Le Trong, I.; Pohl, E.; Ballesteros, J. A.; Stenkamp, R. E.; Palczewski, K.; Lodowski, D. T. J. Struct. Biol. 2006, 156(3), 497-504;
24. Salom, D.; Lodowski, D. T.; Stenkamp, R. E.; Le Trong, I.; Golczak, M.; Jastrzebska, B.; Harris, T.; Ballesteros, J. A.; Palczewski, K. Proc. Natl. Acad. Sci. USA. 2006, 103 (44), 16123-8;
25. Park, J. H.; Scheerer, P.; Hofmann, K. P.; Choe, H. W.; Ernst, O. P. Nature. 2008, 454, 183-7;
26. Rasmussen, S. G.; Choi, H. J.; Rosenbaum, D. M.; Kobilka, T. S.; Thian, F. S.; Edwards, P. C.; Burghammer, M.; Ratnala, V. R.; Sanishvili, R.; Fischetti, R. F.; Schertler, G. F.; Weis, W. I.; Kobilka, B. K. Nature, 2007, 450(7168), 383-7;
27. Rosenbaum, D. M.; Cherezov, V.; Hanson, M. A.; Rasmussen, S. G.; Thian, F. S.; Kobilka, T. S.; Choi, H.-J.; Yao, X.-J.; Weis, W. I; Stevens, R. C.; Kobilka, B. K. Science, 2007, 318(5854), 1266-73;
28. Cherezov, V.; Rosenbaum, D. M.; Hanson, M. A.; Rasmussen, S. G.; Thian, F. S.; Kobilka, T. S.; Choi, H.-J.; Kuhn, P.; Weis, W. I; Kobilka, B. K.; and Stevens, R. C. Science, 2007, 318(5854), 1258-65;
29. Hanson, M. A.; Cherezov, V.; Griffith, M. T.; Roth, C. B.; Jaakola, V. P.; Chien, E. Y.; Velasquez, J.; Kuhn, P.; Stevens, R. C. Structure, 2008, 16(6), 897-905;
30. Warne, T.; Serrano-Vega, M. J.; Baker, J. G.; Moukhametzianov, R.; Edwards, P. C.; Henderson, R.; Leslie, A. G.; Tate, C. G.; Schertler, G. F. Nature, 2008, Jun. 25. [Epub ahead of print]
31. Patny, A.; Desai, P. V.; Avery, M. A. Curr Med Chem. 2006, 13(14), 1667-91;
32. Ballesteros, J. A.; Shi, L.; Javitch, J. A. Mol Pharmacol. 2001, 60(1), 1-19;
33. Becker, O. M.; Shacham, S.; Marantz, Y.; Noiman, S. Curr. Opin. Drug. Discov. Devel. 2003, 6(3), 353-61;
34. Moro, S.; Spalluto, G.; Jacobson, K. A. Trends Pharmacol. Sci. 2005, 26(1), 44-51;
35. Nowak, M.; Kolaczkowski, M.; Pawlowski, M.; Bojarski, A. J. J. Med. Chem. 2006, 49(1), 205-14;
36. McLean, T. H.; Chambers, J. J.; Parrish, J. C.; Braden, M. R.; Marona-Lewicka, D.; Kurrasch-Orbaugh, D.; Nichols, D. E. J. Med. Chem. 2006, 49(14), 4269-74;
37. Hobrath, J. V.; Wang, S. J. Med. Chem. 2006, 49(15), 4470-6;
38. Singh, S.; Malik, B. K.; Sharma, D. K. Chem. Biol. Drug. Des. 2007, 69(3), 191-203;
39. Patny, A.; Desai, P. V.; Avery, M. A. Proteins. 2006, 65(4), 824-42;
40. Lu, Z. L.; Saldanha, J. W.; Hulme, E. C. Trends Pharmacol. Sci. 2002, 23(3), 140-6;
41. Zhang, Y.; Sham, Y. Y.; Rajamani, R.; Gao, J. L.; Portoghese, P. S. ChemBioChem, 2005, 6, 859;
42. Lattanzi, R.; Spetea, M.; Schullner, F.; Rief, S. B.; Krassnig, R.; Negri, L.; Schmidhammer, H. J. Med. Chem. 2005, 48(9), 3372-8;
43. Spetea, M.; Schüllne, F.; Moisa, R. C.; Berzetei-Gurske, I. P.; Schraml, B.; Dorfler, C.; Aceto, M. D.; Harris, L. S.; Coop, A.; Schmidhammer, H. J. Med. Chem. 2004, 47(12), 3242-7;
44. Greiner, E.; Spetea, M.; Krassnig, R.; Schullne, F.; Aceto, M.; Harris, L. S.; Traynor, J. R.; Woods, J. H.; Coop, A.; Schmidhammer, H. J. Med. Chem. 2003, 46(9), 1758-63;
45. Rennison, D.; Moynihan, H.; Traynor, J. R.; Lewis, J. W.; Husbands, S. M. J. Med. Chem. 2006, 49(20), 6104-10;
46. Nieland, N. P.; Moynihan, H. A.; Carrington, S.; Broadbear, J.; Woods, J. H.; Traynor, J. R.; Husbands, S. M.; Lewis, J. W. J. Med. Chem. 2006, 49(17), 5333-8;
47. Grundt, P.; Jales, A. R.; Traynor, J. R.; Lewis, J. W.; Husbands, S. M. J. Med. Chem. 2003, 46(8), 1563-6.

Example 2

Design, Synthesis and Biological Evaluation of 6α- and 6β-N-Heterocyclic Substituted Naltrexamine Derivatives as Mu Opioid Receptor Selective Antagonists Abstract Opioid receptor selective antagonists are important pharmacological probes in opioid receptor structural characterization and opioid agonist functional study. Thus far a non-peptidyl, highly selective, and reversible mu opioid receptor (MOR) antagonist is unavailable. Based on our modeling studies, a series of novel naltrexamine derivatives have been designed and synthesized. Among them, two compounds were identified as leads based on the results of in vitro and in vivo assays. Both of them displayed high binding affinity for the MOR (Ki=0.37 nM and 0.55 nM). Compound 6 (NAP) showed over 700-fold selectivity for the MOR over the delta receptor (DOR) and more than 150-fold selectivity over the kappa receptor (KOR). Compound 9 (NAQ) showed over 200-fold selectivity for the MOR over the DOR and approximately 50-fold selectivity over the KOR. Thus these two novel ligands will serve as leads to further develop more potent and selective antagonists for the MOR.

Introduction

Opioid antagonists have played very important roles in the study of opioid receptors. In fact, the action of an agonist is characterized as opioid-receptor-mediated only if it is competitively antagonized by an opioid antagonist.[1,2] Receptor-selective opioid antagonists are important tools to identify the receptor types that mediate the effects of opioid agonists.[3] The characterization of the mu opioid receptor (MOR) is essential because the analgesic function and addiction/abuse liability of many clinically available opiates are primarily due to their interaction with the MOR.[1,2,4] Thus, MOR selective antagonists are essential for the study of MOR function in drug abuse and addiction. In fact, some antagonists with relatively low selectivity for MOR, e.g. naltrexone, have been shown to inhibit relapse and curb drug craving in opiate addicts.[5-7]

Based on the "message-address concept", highly selective non-peptide antagonists for the kappa opioid receptor (e.g. norbinaltorphimine (norBNI) and 5'-guanidinonaltrindole (GNTI)),[8,9] and for the delta receptor (e.g. naltrindole (NTI))[10] (FIG. 5) were designed and synthesized several years ago. These compounds are widely used as selective ligands in pharmacological studies.

Figure 6:
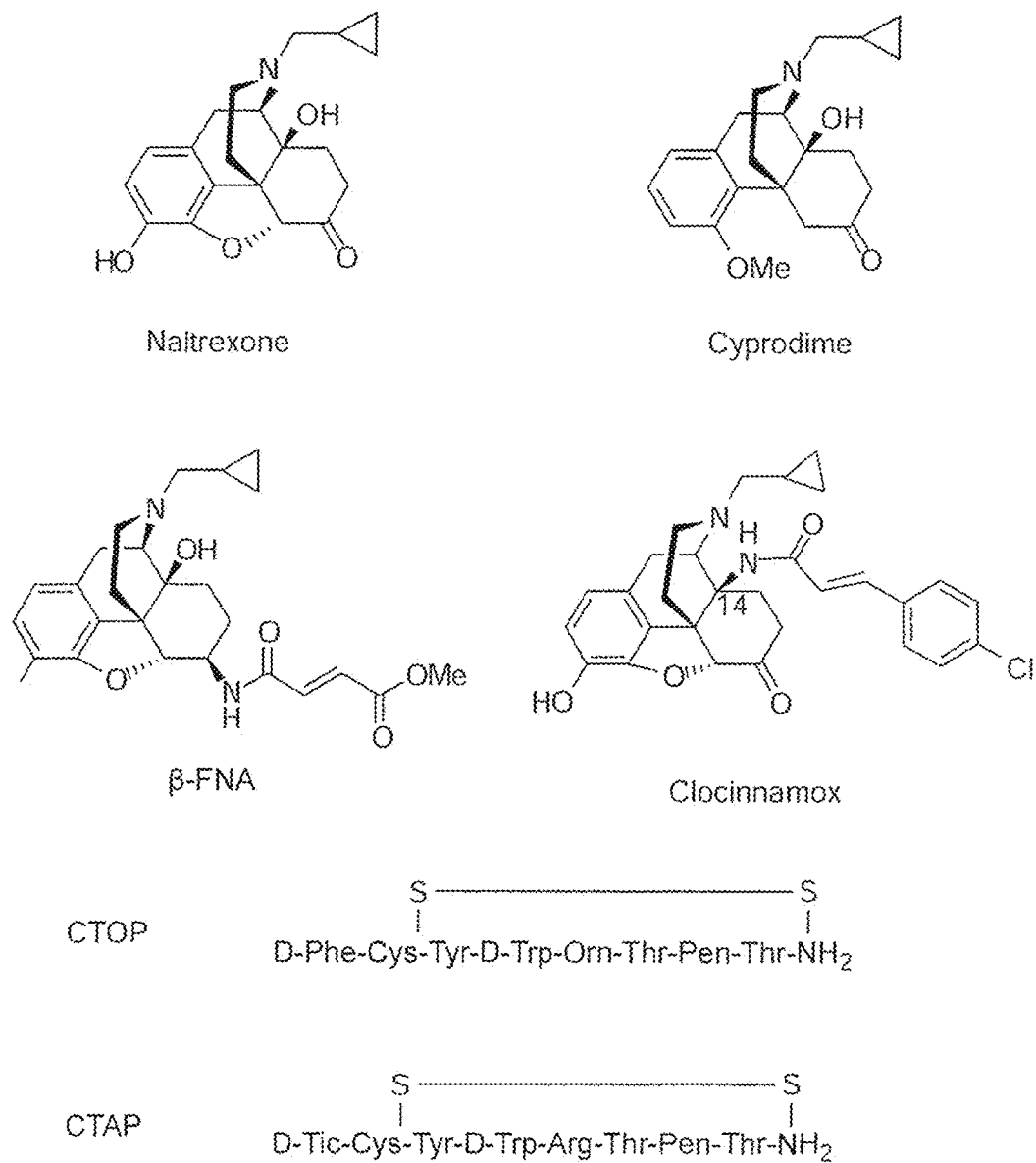

Thus far, however, no optimal non-peptide antagonist has been developed for the MOR, although some moderately potent ligands, e.g. cyprodime[11] are available. Compared with the high selectivity of GNTI for the kappa opioid receptor (KOR) (Ki values ratios are mu/kappa≈120, delta/kappa≈250)9 and NTI for the delta opioid receptor (DOR) (Ki values ratios are mu/delta≈152, kappa/delta≈276),[10] cyprodime only has a moderate selectivity of the MOR over the DOR and KOR (Ki values ratios are kappa/mu≈45, delta/mu≈40).[12] Another drawback of cyprodime is that it has much lower affinity for the MOR than naloxone and naltrexone,[11] which limits its utility. Further structure-activity relationship studies of cyprodime derivatives did not generate any additional antagonist with significantly improved affinity or selectivity for the MOR.[13-17] Although β-funaltrexamine (β-FNA), clocinnamox, and others (FIG. 6), have been reported as selective and irreversible non-peptide antagonists for MOR[18-21] the fact that they bind covalently with the receptor largely limits their utility. In most cases, a reversible antagonist would be preferred because it can inhibit the receptors temporarily for pharmacological study and then can be washed out from the binding locus to "revive" the receptors afterwards.

Most highly selective and reversible mu opioid receptor antagonists currently available are conformation-constrained peptides, e.g. CTOP and CTAP.[22-28] They are relatively metabolically stable and have been used to target the MOR in in vitro and in vivo studies while their limited bioavailability may not be suitable for many types of in vivo studies and for medical applications. Optimal utility of antagonists as pharmacological tools requires both in vitro and in vivo activity. Non-peptide ligands are preferred due to their ability to penetrate the CNS and lesser vulnerability to metabolic inactivation compared to the peptide agents. Therefore, the development of a non-peptide, potent, selective and reversible antagonist for the mu opioid receptor is highly desirable.

Naltrexone is a promising template for the design of the opioid receptor selective ligands. The successful modification of naltrexone in the synthesis of NTI, norBNI and GNTI are good examples. While naltrexone has nanomolar affinity for all three opioid receptors, it also shows moderate selectivity for the MOR over DOR and KOR. Some chemical structure features are essential for its high affinity for the opioid receptors and should not be abolished. For example, the addition of a 3-hydroxyl group onto cyprodime and its derivatives will "markedly enhance affinity at all three opioid receptors".[13] In addition, the chemistry related to the structural modification of naltrexone has been thoroughly studied. This information will be beneficial to the synthetic route design of naltrexone derivatives.

In this Example, we report the design, synthesis and biological evaluation of two series of novel naltrexone-derived ligands as selective MOR antagonists. Molecular modeling of the naltrexone binding pocket in the homology models of the three opioid receptors led to the identification of an alternative "address" domain in the MOR that may enhance selectivity for the MOR over the DOR and KOR. Two series of ligands were designed and synthesized as proof-of-concept. Biological evaluation of these two series of compounds revealed some ligands with high affinity and selectivity for the MOR. Based on these results, two exemplary compounds have been identified for future optimization.

Results and Discussion

Molecular Modeling

Figure 7:
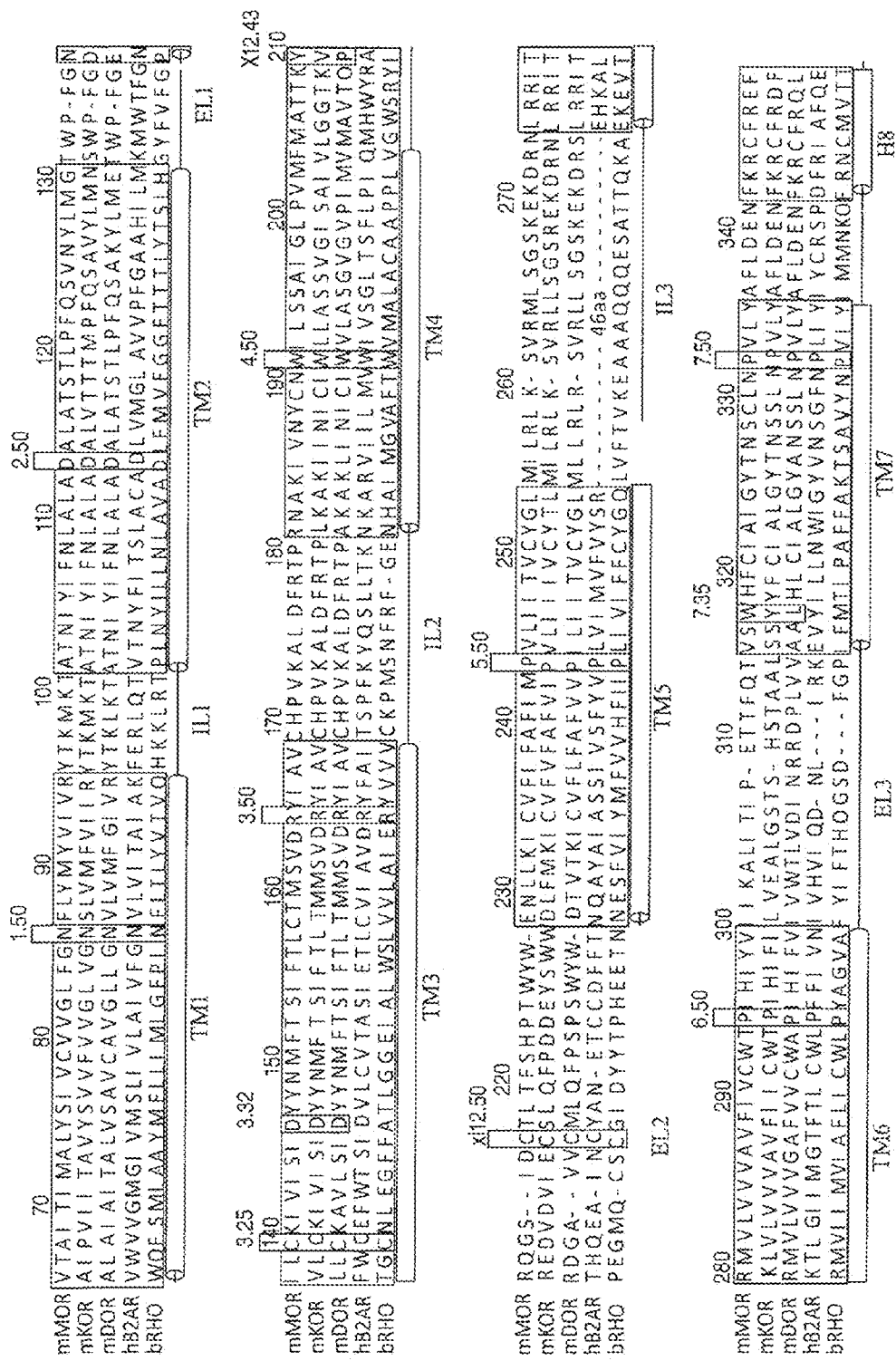
FIG. 7. The sequence alignment of the MOR (SEQ ID NO: 1), DOR (SEQ ID NO: 2), and KOR (SEQ ID NO: 3), with human β2AR (SEQ ID NO: 4), and bovine rhodposin (SEQ ID NO: 5). The Ballesteros-Weinstein numbering system was adopted to mark all the conserved amino acid residues among most of the GPCRs and colored in red. The extracellular loop 2 (EL2) was numbered following the assignment proposed by Johnson (Xhaard, H.; Nyrönen, T.; Rantanen, V. V.; Ruuskanen, J. O.; Laurila, J.; Salminen, T.; Scheinin, M.; Johnson, M. S. Model structures of alpha-2 adrenoceptors in complex with automatically docked antagonist ligands raise the possibility of interactions dissimilar from agonist ligands. J Struct. Biol. 2005, 150(2), 126-43.) The MOR protein was numbered accordingly above its sequence. The secondary structure of the MOR receptor 3D conformation based on bovine rhodopsin crystal structure was marked out below all the sequences. The conserved aspartate residues among all three opioid receptors are residues 3 and 32. The two non-conserved residues x12.43 and 7.35 are also indicated.

To facilitate ligand design, homology models of all three opioid receptors were constructed. To date, in the whole superfamily of G-protein coupled receptors (GPCRs), only the X-ray crystal structures of bovine rhodopsin,[29-32] opsin,[33] and the human β2- and β1-adrenergic receptor[34-38] have been successfully obtained with high resolution. Most molecular models of other GPCRs have been constructed using the rhodopsin structure as a template. Therefore, homology models of the mu, delta and kappa opioid receptors were constructed based on the X-ray crystal structure of bovine rhodopsin after sequence alignment (FIG. 7). Molecular dynamics simulations were conducted to optimize the conformation of the models. The models contain not only the transmembrane helices, but also the extracellular and intracellular domains so that these models were integrated and complete. The MOR model was also optimized in a membrane-aqueous system.[39] The DOR and KOR models were also optimized following the same method. All amino acid residues in these three models have reasonable bond lengths and bond angles. The analysis of $\phi$, $\psi$, $\chi 1$, $\chi 2$ angles of the resulting protein conformations was further conducted with Procheck 4.1.

Figure 8A:
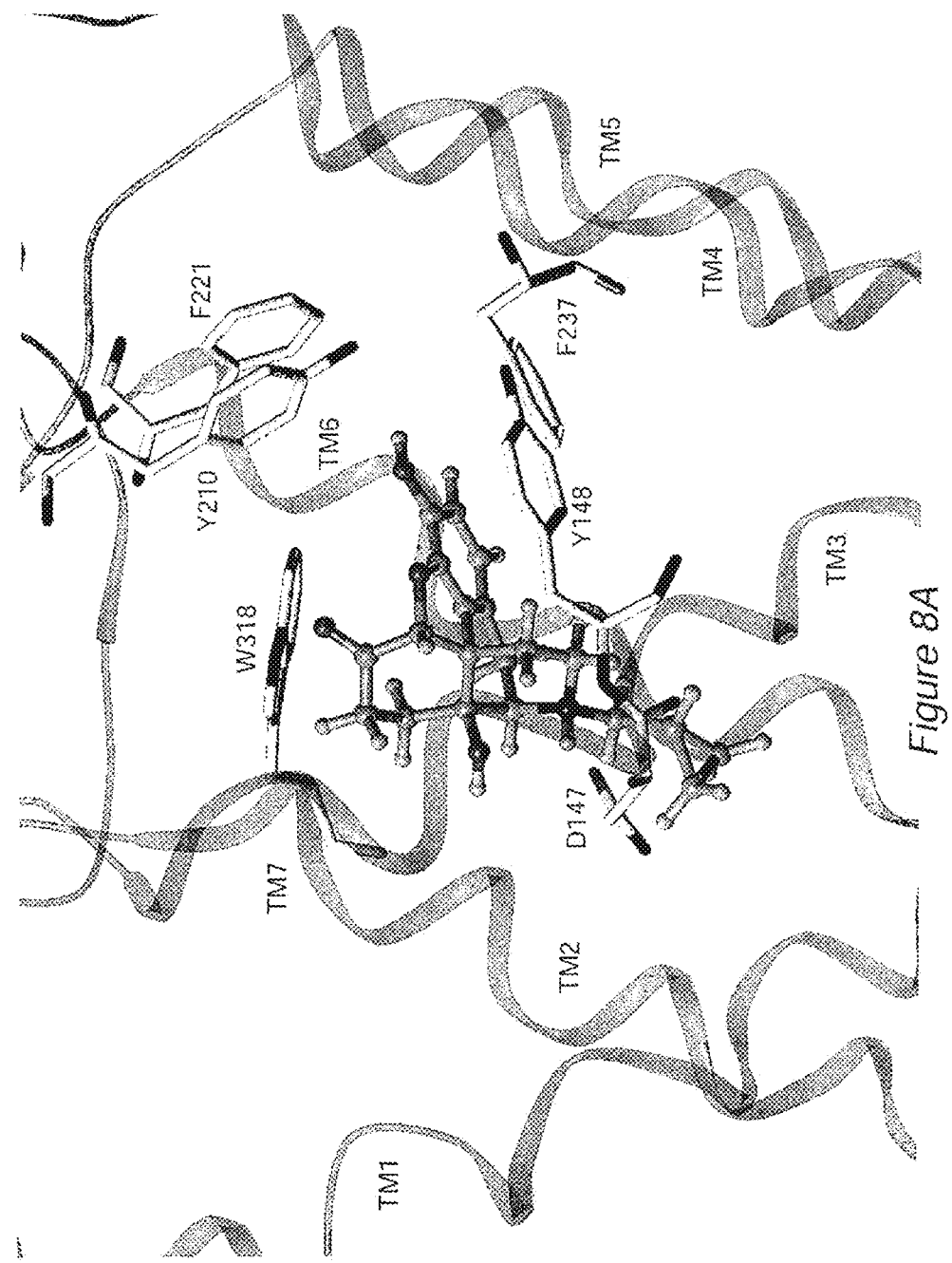
FIG. 8A-C. Naltrexone (NTX) docked in the homology models in the MOR, DOR and KOR. NTX and the amino acid residues are in stick form. The receptor homology models are in ribbon. NTX is in A) MOR, B) DOR and C) KOR.
Figure 8B:
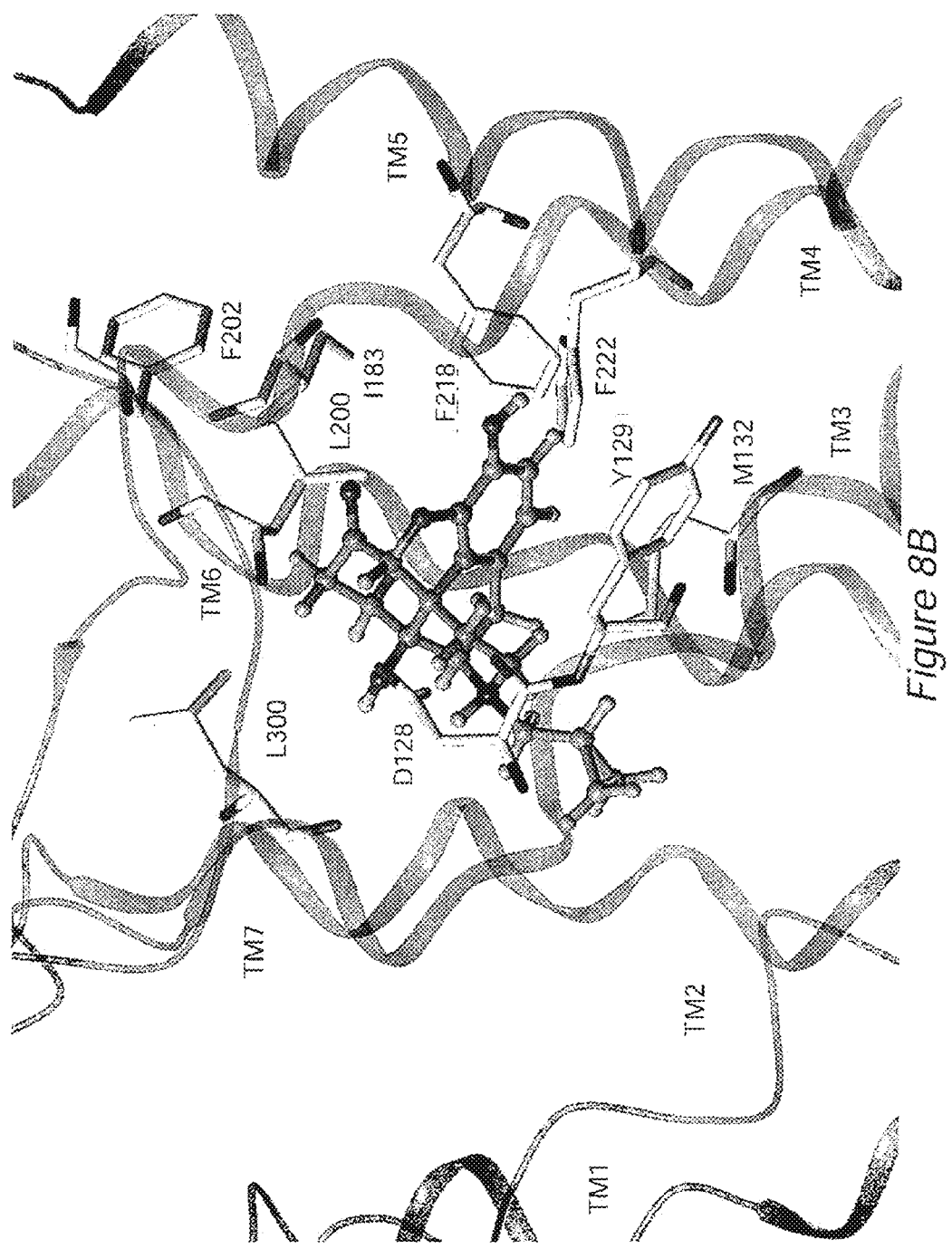
Figure 8C:
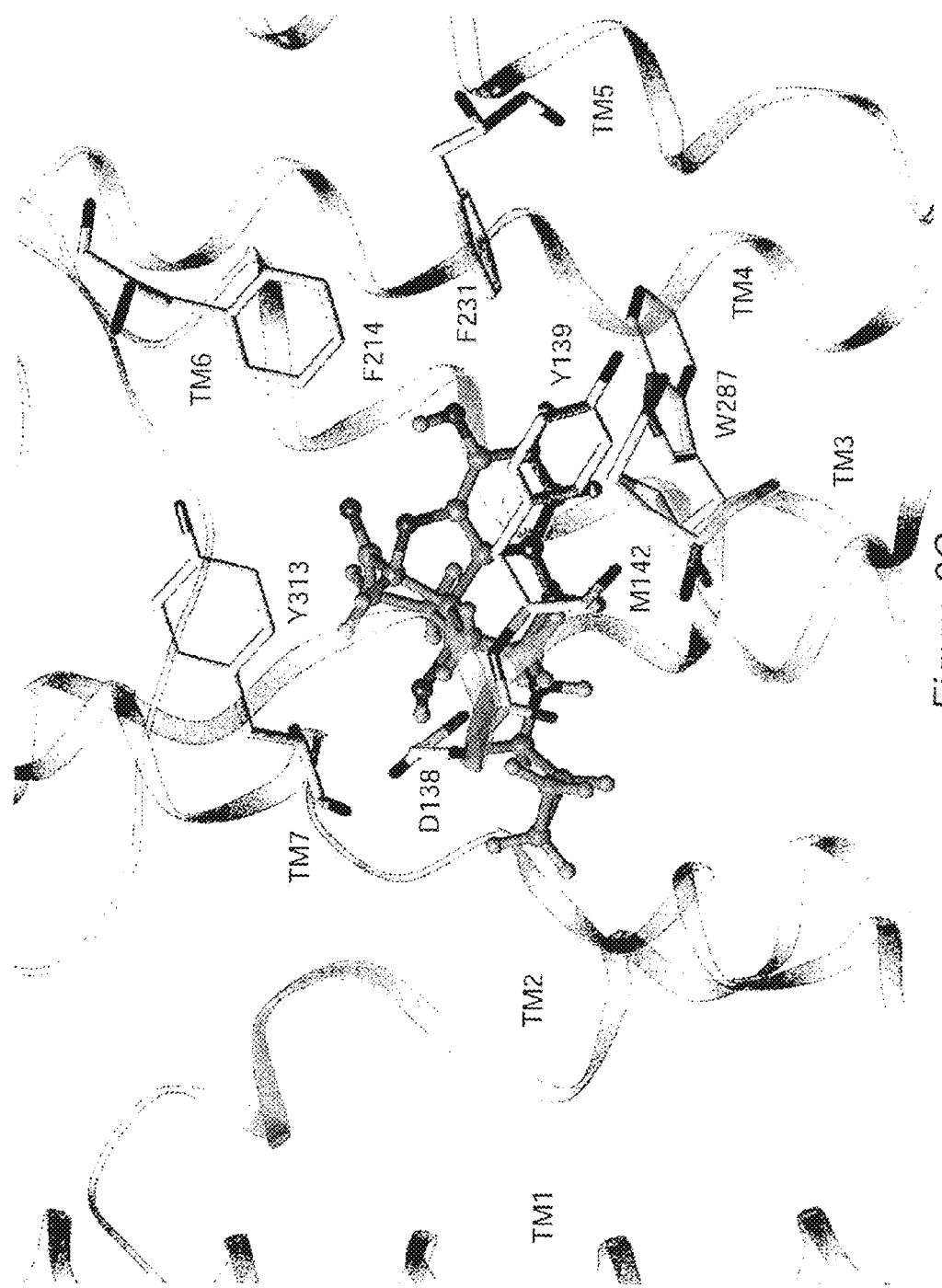

Because naltrexone is a universal antagonist at all three opioid receptors with moderate selectivity for the MOR, we decided to use it as a probe molecule to identify the antagonist binding site in all three opioid receptors. By comparison of the differences among these three binding pockets, we attempted to identify the amino acid residues that are critical to ligand selectivity for the MOR. Three steps were involved in the identification of the critical amino acid residues that differentiate the binding affinity of naltrexone in the three opioid receptors. The first step was the interactive docking of naltrexone into the binding locus of the receptor to form the ligand-receptor complex. The second step was energy minimization and molecular dynamics carried out for the ligand-receptor system to relax and optimize binding interactions between the ligand and amino acid residues in the binding cavity. The third step is the identification and comparison of the naltrexone binding locus in all the three receptors. The ligand-receptor complex structure obtained after 11 ps of molecular dynamics simulation is depicted in FIG. 8A-C. In these complexes, the distance between the protonated nitrogen atom in the 17-amino group of NTX and the carboxyl group of Asp 147 (D3.32) was initially anchored at 4.0 Å and retained at this value by a weak harmonic restraint (2 kcal/Å) during the molecular dynamics simulation to represent the putative salt bridge that has been inferred from experimental studies.[53] In the lowest energy conformation of the complex extracted from the last 5 ps molecular dynamics simulation, the distance (4.1 Å) was compatible with the initial setting.

As shown in FIG. 8A, the binding pocket of naltrexone the entire molecule in the MOR was mainly composed of aliphatic amino acid residues. The positively charged amino moiety of the ligand was within the range of an ionic interaction with Asp147 (D3.32). We also noticed that the carbonyl group on C(6) of naltrexone was orientating towards an aromatic binding pocket formed mainly by amino acid residues from the extracellular loops (ELs) of the receptor, including Tyr210 (Yxl2.43) and Phe221 (Fxl2.54) from EL2 and Trp318 (W7.35) at the border of EL3 and Helix 7.

In FIG. 8B, the naltrexone's binding pocket in the DOR was very similar to that in the MOR except that there existed no aromatic binding locus formed by multiple amino acid residues to which the C(6) carbonyl group of naltrexone pointed. At the conserved region, only Phe202 (Fxl2.54) from EL2 was in the vicinity while Pro191 (Pxl2.43) and Leu300 (L7.35) are not aromatic ones. This difference might be applicable in the design of ligands that are selective for the MOR over the DOR.

Further study of the naltrexone binding pocket in the KOR (FIG. 8C) showed that there was an aromatic/aliphatic binding pocket formed with the contribution of Phe214 (Fxl2.54) from EL2, Phe231 (F5.37) on Helix 5, and Tyr313 (Y7.35) from Helix 7. However, only one residue Tyr313 (Y7.35) may faun hydrogen bond with the ligand, while in the MOR binding locus at least two of them are available to be considered.

Therefore, our molecular modeling study of the MOR antagonist binding pocket using naltrexone as the probe has revealed an aromatic binding locus at the extracellular loop region. Further comparison with the DOR and KOR antagonist binding pockets indicated that the existence of amino acid residues acting as potential hydrogen bonding donors and/or acceptors may be a unique structural feature of this aromatic binding locus in the MOR. Therefore, this binding domain may serve as an alternate "address" motif in the MOR that contributes to ligand recognition of the MOR selectively over DOR and KOR. Molecular design targeting to this "address" domain could lead to the identification of selective MOR antagonists. To be noticed, accumulated evidence has shown that the extracellular loops of GPCRs may play a critical role in the binding pocket of their small molecule ligands, including a number of opioid receptor agonists and antagonists.[39-46] It has been found that EL3 of the MOR is critical for the binding of MOR-selective agonists by comparing their binding affinities for MOR/DOR and MOR/KOR chimeric receptors with those for the wild-type MOR, DOR and KOR.[43,44] Site-directed mutagenesis studies have revealed that certain amino acid residues in EL3 could be essential for ligand (including agonist and antagonist) selectivity for the MOR.[45-47] More specifically, Trp318 from EL3 has been identified as an important residue for the binding affinity and selectivity of varies ligands for the MOR.[40,41,43,48] These reports are consistent with the observation from our modeling studies.

Molecular Design

Based on the molecular modeling study, two series of ligands were designed as MOR selective antagonists (Table 2). None of them have been discussed in the literature as selective opioid receptor ligands.

TABLE 2

The ligands designed as the mu opioid receptor selective antagonists.

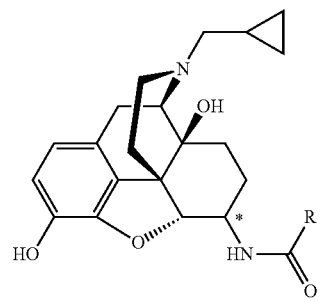

| Compound | R | C6-configuration |
|---|---|---|
| 1 | 2-pyridyl | α |
| 2 | 2-pyridyl | β |
| 3 | 3-pyridyl | α |
| 4 | 3-pyridyl | β |
| 5 | 4-pyridyl | α |
| 6 | 4-pyridyl | β |
| 7 | phenyl | α |
| 8 | phenyl | β |
| 9 | 3-isoquinolinyl | α |
| 10 | 3-isoquinolinyl | β |
| 11 | 2-quinolinyl | α |
| 12 | 2-quinolinyl | β |
| 13 | 3-quinolinyl | α |
| 14 | 3-quinolinyl | β |

TABLE 2-continued

The ligands designed as the mu opioid receptor selective antagonists.

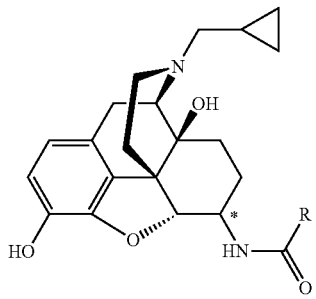

| Compound | R | C6-configuration |
|----------|---|------------------|
| 15 | ![naphthyl] | α |
| 16 | ![naphthyl] | β |

In the structure of these ligands, we introduced a heteroaromatic moiety onto the 6-position of naltrexone. An amide bond was adopted as the linkage of the side chain moiety to the morphinan skeleton. Therefore, these ligands can be considered derivatives of naltrexamine. The configuration of C(6) will be either α or β. Such a stereochemical arrangement could play an important role for the affinity and the selectivity of the ligand, as has been demonstrated by β-FNA and β-FNA.[49] The aromatic character of this side chain designed to have aromatic stacking interaction with the aromatic binding locus in the MOR in order to differentiate from the DOR. The nitrogen atom in the aromatic system will act as a hydrogen bond acceptor to probe for the potential formation of a hydrogen bond with Tyr210 or Trp318 in the binding locus from the ELs of the MOR in order to possibly differentiate from the KOR. Compounds with phenyl and naphthalenyl substitutions were designed as control compounds to test our hypothesis. These two series of ligands served as proof-of-concept to test the identification of the alternate "address" domain in MOR.

Chemical Synthesis

For the synthesis of these 6-substituted derivatives of naltrexamine, the starting material was naltrexone. The stereoselective synthesis of α- and β-naltrexamine has been applied successfully in the synthesis of their derivatives in the literature.[50]

Figure 9:
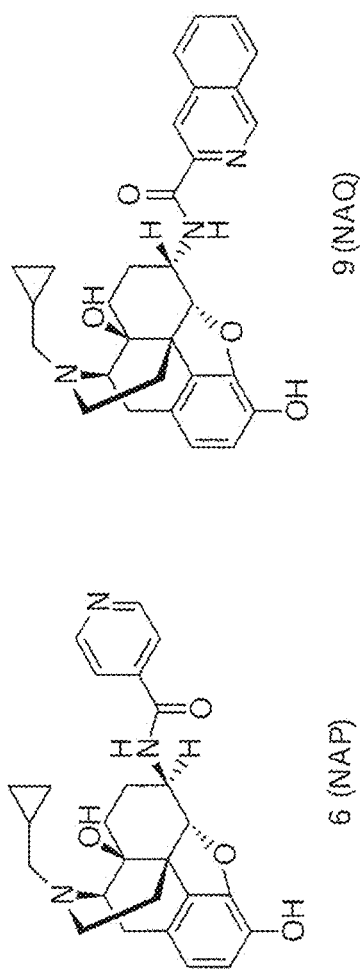
FIG. 9. Chemical structures of compounds 6 and 9.

In our case, α-naltrexamine was obtained with a yield of 60% in three steps, while β-naltrexamine was obtained with a yield of 63% in three steps. The amide bond formation between the naltrexamine and the side chain moiety was straightforward. Depending on the commercial availability of the aromatic moiety, either in acyl chloride or acid form, condition 1 or 2 was adopted. Under mild basic condition, the intermediate, 3,6-disubstituted naltrexamine, was converted to the 6-mono-substituted target compound (FIG. 9) with reasonable yield. All the ligands were fully characterized before submitting for biological studies.

Biological Evaluation

Biological screening for the synthesized ligands was focused on in vitro radioligand binding assay and functional assays, and in vivo behavioral tests. Basically, the radioligand binding assay was adopted to characterize the affinity and selectivity of new ligands for the MOR, DOR and KOR, whereas the $^{35}$S-GTP[γ S]-binding functional assay was applied to determine whether each new ligand acted as an agonist, partial agonist or antagonist of the MOR by determining its efficacy for G-protein activation relative to a full agonist at the MOR. Agonist efficacy were measured at the level of G-protein activation because efficacy is most accurately determined at this proximal level of signal transduction.[51-53] The use of cell lines heterologously expressing each of the cloned receptors has become standard practice because it provides a pure source of each opioid receptor type free of other opioid receptor types. Furthermore, these systems express the receptor at high density to provide optimal signal-to-noise ratios in the radioligand and $^{35}$S-GTP[γS] binding assays. The in vivo tests were focused on the inhibition of morphine's antinociception activity and behavioral properties of those compounds showing high selectivity and low agonist efficacy at the MOR.

In Vitro Pharmacological Study

The primary testing of these ligands included the competitive radioligand binding assay using the mono-cloned opioid receptors expressed in CHO cell lines. [$^3$H]naloxone, [3H]NTI and [$^3$H]norBNI were used to label the MOR, DOR and KOR, respectively. The binding affinities of these ligands to the mu, delta and kappa opioid receptors are summarized in Table 3. Most of these ligands showed sub-nanomolar affinity for the MOR and significant selectivity for the MOR over DOR and KOR. These results demonstrated that our primary molecular design was successful.

TABLE 3

The binding affinity and selectivity of C(6) naltrexamine derivatives (n = 3)

| Compound | Ki (nM) ± SEM | | | Selectivity ratio | |
|----------|---------------|---|---|-------------------|---|
| | MOR | DOR | KOR | delta/mu | kappa/mu |
| NTX | 0.26 ± 0.02 | 117.06 ± 8.94 | 5.15 ± 0.26 | 450 | 20 |
| β-FNA | 0.41 ± 0.04 | 27.78 ± 4.60 | 0.94 ± 0.05 | 68 | 2 |
| CTAP | 2.02 ± 0.71 | 1441.0 ± 106.1 | 1012.7 ± 174.8 | 713 | 501 |
| 1 | 2.6579 ± 0.424 | 64.467.85 ± 15.976.81 | 222.5834.3 ± 11.972.60 | 24 | 84 |
| 2 | 5.856.46 ± 1.4156 | 215.1837.5 ± 21.023.2 | 277.96306.8 ± 67.7774.8 | 37 | 47 |
| 3 | 0.157 ± 0.078 | 40.785.01 ± 8.399.26 | 7785.234 ± 224.4376 | 265 | 501 |
| 4 | 0.145 ± 0.04 | 211.91.98 ± 15.587.2 | 5.4298 ± 1.1830 | 1413 | 40 |
| 5 | 0.4853 ± 0.123 | 186.64206.0 ± 32.075.4 | 19.5621.59 ± 9.0610.00 | 389 | 41 |
| 6 (NAP) | 0.3741 ± 0.078 | 277.51306.3 ± 7.978.8 | 607.702 ± 56.5816 | 747 | 163 |
| 7 | 1.4155 ± 0.628 | 385.84425.4 ± 83.9992.6 | 41.695.96 ± 6.0668 | 274 | 30 |
| 8 | 0.921.03 ± 0.304 | 47538.820 ± 19.9422.4 | 7.798.75 ± 1.5372 | 522 | 8 |
| 9 (NAQ) | 0.556 ± 0.15 | 135.2.50 ± 27.015 | 26.4593 ± 5.2232 | 241 | 48 |
| 10 | 0.101 ± 0.067 | 15.42 17.13 ± 10.829.74 | 1.5875 ± 0.768 | 156 | 16 |
| 11 | 0.213 ± 0.112 | 148.2059.4 ± 64.809.7 | 9.8410.58 ± 0.961.03 | 693 | 46 |

TABLE 3-continued

The binding affinity and selectivity of C(6) naltrexamine derivatives (n = 3)

| Compound | Ki (nM) ± SEM | | | Selectivity ratio | |
| --- | --- | --- | --- | --- | --- |
| | MOR | DOR | KOR | delta/mu | kappa/mu |
| 12 | 0.11 ± 0.03 | 3.8694 ± 1.213 | 5.0414 ± 1.303 | 36 | 47 |
| 13 | 0.123 ± 0.03 | 32.196.01 ± 1.0113 | 1.812.03 ± 0.112 | 277 | 16 |
| 14 | 0.078 ± 0.02 | 11.612.52 ± 2.993.23 | 0.5762 ± 0.202 | 157 | 8 |
| 15 | 8.3678 ± 1.7180 | 518.3245.6 ± 14.068 | 640.8.76 ± 15.776.6 | 62 | 73 |
| 16 | 55.67.5 ± 3.67 | 29.2630.17 ± 4.7489 | 657.268 ± 17.2679 | 0.5 | 1 |

The Ki values for the mu, delta and kappa opioid receptors are n = 3. The averages are reported along with their standard error of the means, SEM, for each compound. The comparison to percent stimulation of DAMGO is the Emax of the compound compared to the Emax of DAMGO (normalized to 100%). Naltrexone, β-FNA and CTAP were tested along as positive controls under the same conditions.

As shown in Table 4, target compound 1 to 6 all have sub-nanomolar or nanomolar affinity for the MOR while much lower affinity for the DOR and KOR. Specifically, compound 4 showed over 1,000-fold selectivity for the MOR over DOR, whereas compound 6 showed over 700-fold selectivity for the MOR over DOR, and over 150-fold selectivity for the MOR over KOR. The control compound 7 and 8 showed somewhat lower affinity for MOR and lower selectivity for MOR over KOR. These results suggest the possibility of hydrogen bonding or other polar interactions between the target compounds and the MOR because the only unique chemical structure in the target compounds is the nitrogen atom in the pyridine ring. Similarly, target compounds 9 to 14 all showed high sub-nanomolar affinity for MOR whereas compound 9 and 11 exhibited the highest selectivity for the MOR over both the DOR and KOR. Again we observed significantly lower affinity and selectivity of the control compounds 15 and 16 for the MOR. This finding further supported the possibility of hydrogen bonding or some other polar interaction between the target compounds and the MOR because of the existence of a quinoline or isoquinoline ring in the target compounds verses the pure aromatic ring system of the naphthalene moiety in the control compounds.

Specifically, compounds 6 and 9 showed the lowest relative efficacy, with approximately 20% of the maximal stimulation produced by DAMGO. Compounds 6 and 9 produced stimulation similar to nalbuphine, a ligand with very low efficacy to activate the MOR. As the main goal of this project is to develop a neutral antagonist of the MOR, their high affinity and selectivity for the MOR and very low agonism at the MOR shed light on our future molecular design. In order to further characterize their pharmacological profile, we conducted in vivo study of these compounds.

In Vivo Pharmacological Evaluation

The potential MOR selective antagonists were evaluated for acute agonistic and antagonistic effects in mice. In detail, they were tested for their ability to produce antinociception and to antagonize the antinociceptive effects of morphine in the mouse tail immersion test. The data are summarized in Table 5. As shown, both compounds 6 and 9 (FIG. 9), were found to be potent antagonists of morphine. Their antagonist $AD_{50}$ values were 4.51 and 0.45 nM, and neither of these ligands produced any agonist effect in this test at doses up to 100 mg/kg. This is in agreement with our original molecular design hypothesis as well as the in vitro functional assays.

TABLE 4

The efficacy and potency of target compounds in $^{35}$S-GTP[γS]-binding functional assay in the MOR expressing CHO cells (n = 3)

| Compound | $EC_{50}$ (nM) | Emax (% Stim) | Percent Max of DAMGO |
| --- | --- | --- | --- |
| DAMGO | 45.06 ± 6.63 | 366.5 ± 23.0 | 100.0 ± 6.2 |
| 1 | 23.905.16 ± 4.6690 | 133.5 ± 9.8 | 37.79 ± 2.68 |
| 2 | 269.2801 ± 8.0588 | 150.6 ± 15.8 | 41.09 ± 4.32 |
| 3 | 1.0112 ± 0.404 | 164.3 ± 16.5 | 44.82 ± 4.50 |
| 4 | 0.336 ± 0.145 | 106.7 ± 18.3 | 29.11 ± 5.00 |
| 5 | 1.2639 ± 0.6774 | 136.8 ± 17.8 | 37.32 ± 4.87 |
| 6 (NAP) | 1.149 ± 0.3842 | 83.3 ± 3.1 | 22.72 ± 0.84 |
| 9 (NAQ) | 4.3644 ± 0.723 | 58.008.0 ± 9.303 | 15.8383 ± 2.5353 |
| 10 | 0.2730 ± 0.067 | 120.9 ± 9.0 | 32.99 ± 2.46 |
| 11 | 0.0910 ± 0.04 | 239.6 ± 22.5 | 65.38 ± 6.13 |
| 12 | 0.6970 ± 0.199 | 149.8 ± 26.1 | 40.87 ± 7.20 |
| 13 | 2.2956 ± 0.7281 | 164.3 ± 14.5 | 44.83 ± 3.96 |
| 14 | 0.2931 ± 0.02 | 195.8 ± 32.0 | 53.41 ± 8.74 |

All of these ligands except the controls (which showed lower affinity for the MOR) were then tested in the $^{35}$S-GTP[γS] binding functional assay using the MOR-expressing CHO cell line (Table 4). The $^{35}$S-GTP[γS] binding results were analyzed in such a way as to normalize the stimulation produced by each novel ligand to that obtained with the full agonist DAMGO, which provided a measurement of relative efficacy. These results demonstrated that all of the novel ligands showed partial agonism.

Therefore, these two compounds may be applied as leads for our next generation of molecular design and synthesis to identify pure, potent and highly selective antagonists for the MOR. In addition, compounds 1 and 2 had similar $ED_{50}$ values to compound 9 and compounds 4, 5 and 13 were equally potent to compound 6 as a morphine antagonist. On the other hand, compound 12 was more potent than morphine and compounds 10 and 11 were equally potent to morphine in producing antinociception in this test.

TABLE 5

AD$_{50}$ values for Naloxone naloxone and the two series of C6-naltrexamine derivatives versus morphine in the warm-water tail immersion test in vivo.

| Compound | AD$_{50}$ value (mg/kg (95% C.L.)) for Blockade of morphine antinociception |
|---|---|
| Naloxone | 0.05 (0.03 to 0.09) |
| 1 | 0.8994 (0.759 to 1.0713) |
| 2 | 0.336 (0.269 to 0.4347) |
| 3 | 36.7740.59 (29.9933.10 to 44.9849.65) |
| 4 | 1.3852 (0.7886 to 2.4368) |
| 5 | 8.69.55 (5.3591 to 13.975.42) |
| 6 (NAP) | 4.5198 (2.4570 to 8.269.12) |
| 9 (NAQ) | 0.456 (0.277 to 0.789) |
| 10 [a] | Inactive |
| 11 [b] | Inactive |
| 12 [c] | Inactive |
| 13 | 4.4598 (2.4170 to 8.159.12) |
| 14 | 42.555.90 (235.6753 to 76.5182.53) |

[a] Agonist, ED$_{50}$ 1.19 mg/kg (morphine ED$_{50}$ 2.59 mg/kg);
[b] Agonist, ED$_{50}$ 4.57 mg/kg;
[c] Agonist, ED$_{50}$ 0.04 mg/kg.

Interestingly, some of the target compounds did not show parallel functional activity between the in vitro and the in vivo studies. For example, both compounds 6 and 9 showed partial agonism in the $^{35}$S-GTP[γS] binding assay while acting as full antagonists in the warm-water tail immersion test. On the other hand, compounds 10, 11 and 12 showed only moderately higher partial agonism in the $^{35}$S-GTP[γS] binding assay but acted as full agonists in the in vivo assays. To our understanding, there are several factors that might have contributed to these observations. First, it has been reported that the level of antinociception produced by an opioid is dependent on both the intrinsic efficacy of the drug and the stimulus intensity. Some low efficacy MOR partial agonists, such as butorphanol, produced maximal levels of antinociception at a lower temperature nociceptive stimulus (50° C.) but not at a higher temperature (56° C.) stimulus.[54] On the other hand, butorphanol acted as an antagonist and shifted the dose-effect curve of the high-efficacy opioid alfentanil to the right in a competitive manner at a higher temperature (55° C.) stimulus.[55] This may explain why the two exemplary compounds did not show any efficacy at the higher temperature (56° C.) stimulus and thereby acted as full antagonists in the in vivo study. Second, some ligands could have significant intrinsic efficacy at the DOR or KOR, while acting as low efficacy partial agonists at the MOR which might explain why compounds 10, 11 and 12 acted as full agonists in vivo.

Further Molecular Modeling Study

In order to verify that the two compounds that acted as selective MOR ligands utilized the alternate "address" domain identified from the previous modeling study, further molecular modeling study was conducted. First, compound 6 and 9 were built using the InsightII/Discover program and their conformation energy minimization was conducted. Then, as we have described for the docking study of naltrexone in the three opioid receptor homology models, they were docked into the homology model of MOR interactively. The orientation of the newly introduced C(6) side chain was not deliberately considered originally. The lowest energy conformation after the minimization and the dynamics simulation of the ligand/receptor complex is illustrated in FIGS. 10A and B.

Figure 10A:
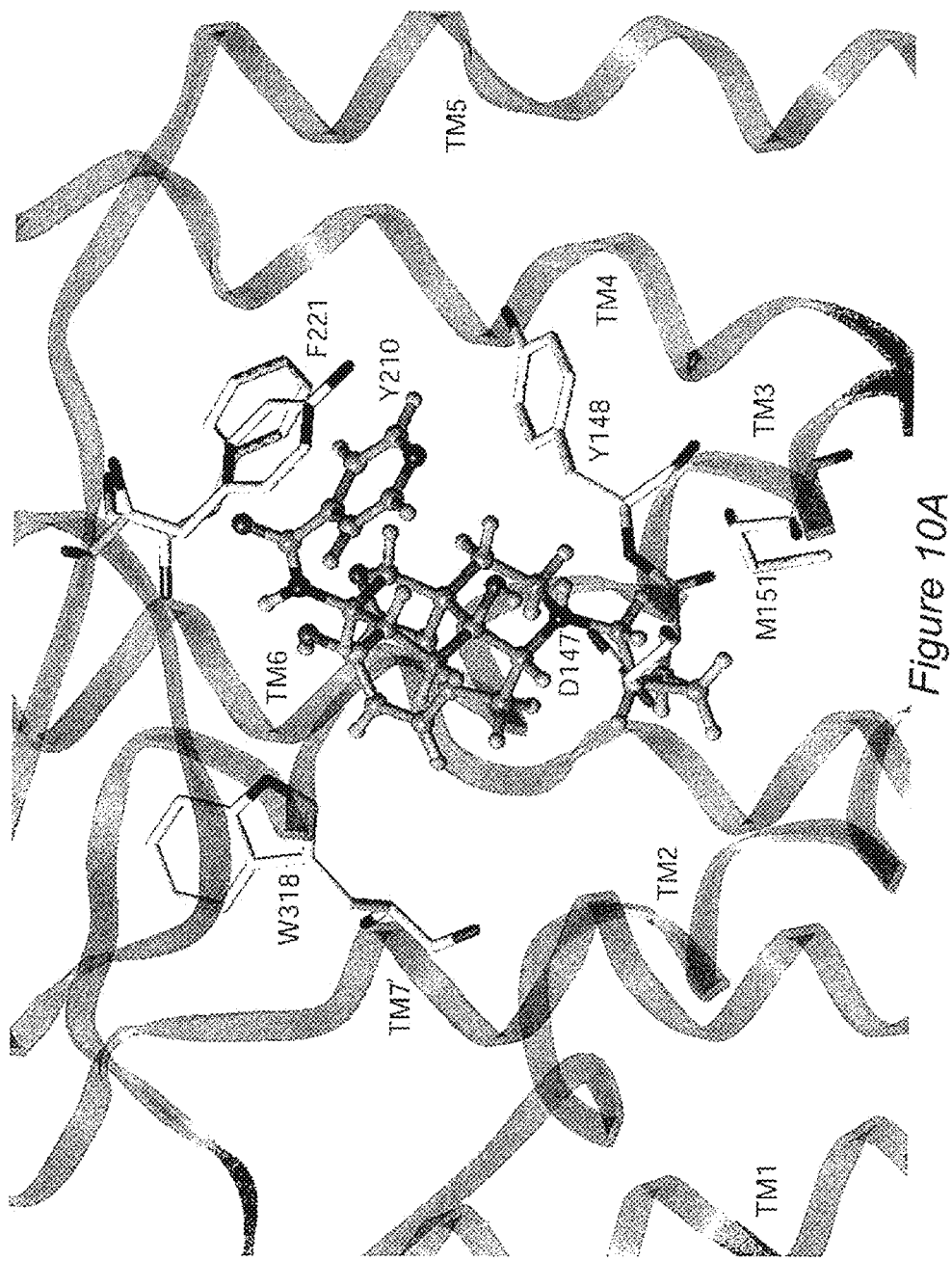
FIGS. 10A and B.
Figure 10B:
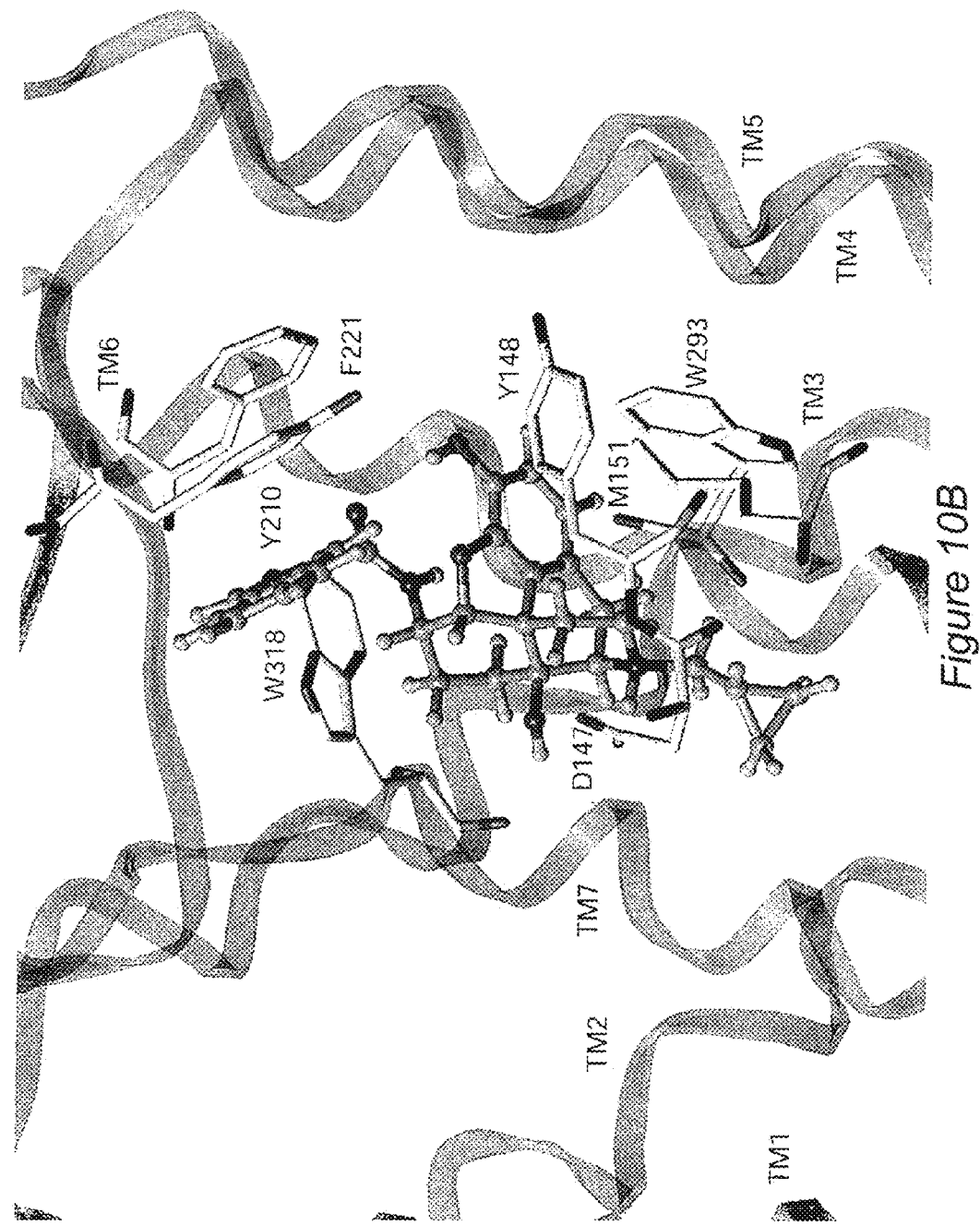

As shown in FIG. 10A, the C(6) side chain in compound 6 pointed to the aromatic binding locus at the extracellular loop region of the MOR. The pyridinyl moiety was in the vicinity of Tyr210 (Yxl2.43) while the distance between the nitrogen atom in the pyridine ring and the oxygen atom in the hydroxyl group of Tyr210 (Yxl2.43) was 3.37 Å. Similarly, the C(6) side chain in compound 9 also pointed to the aromatic binding locus at the extracellular loop region of the MOR while the isoquinolinyl moiety in 9 was in the vicinity of Trp318 (W7.35) (FIG. 10B). The distance between the nitrogen atom in the isoquinoline ring and the nitrogen atom in the indole ring of Trp318 (W7.35) was 3.64 Å. Both distances could be plausible for hydrogen bonding interaction between the C(6) side chains in the ligands and the specified amino acid residue.

Because these two residues (Tyr210 (Yxl2.43) and Trp318 (W7.35)) are not conserved in the DOR and KOR, it seems that these two residues could act as an alternate "address" domain in MOR, and this plausible hydrogen bonding could contribute to the selectivity of the exemplary compounds 6 and 9 for the MOR. As our molecular models are based on homology modeling of these opioid receptors and are preliminary, site-directed mutagenesis and radioligand binding analysis with the mutated MOR will be conducted in future studies to confirm this hypothesis.[56]

Conclusions

In summary, based on the molecular modeling study of the opioid receptor antagonist binding pocket using naltrexone as a probe molecule, an alternative "address" binding domain has been identified in the MOR antagonist binding pocket. Two series of novel ligands have been designed and synthesized to target on this "address" domain as proof-of-concept. Competition binding and in vitro functional assays have identified two compounds with sub-nanomolar affinity for the MOR and high selectivity over the DOR and KOR. Both compounds showed partial agonism in the in vitro G-protein activation test and potent antagonism in the in vivo antinociceptive test. Further molecular modeling study has implicated that the selectivity of these two ligands for the MOR could be the result of potential hydrogen bonding between the ligand and the "address" binding locus in the MOR. Moreover, we have also observed that some of the compounds in these series showed a range of efficacies as MOR partial agonists. These ligands would serve as pharmacological tools to obtain information on MOR activation mechanisms and on structural parameters that affect ligand efficacy at the MOR.

Experimental Section

Molecular Modeling

A Silicon Graphics Octane 2 workstation, equipped with two parallel R12000 processors, was used for all computational studies. InsightII (Accelrys)[57] package was used for modeling. InsightII/Homology module was used to construct the homology models of three opioid receptors based on the X-ray crystal structure of bovine rhodopsin, as reported previously.[39] InsightII/Discover module was applied to construct all the small molecules in their nitrogen-protonated form. Minimization with the steepest descent and then the conjugate gradient algorithm were performed to generate the lowest energy conformation for each ligand studied. Then a molecular dynamics simulation was performed (an equilibration phase of 1,000 fs at 300 K, followed by a collection phase of 5,000 fs at the same temperature) to further study the small molecule conformation. The lowest energy conformation of the molecule from the last 2 ps molecular dynamics simulation was extracted and applied as the initial configuration for docking into the proposed binding site of the opioid receptors. The docking of the small molecule was conducted interactively using InsightII/Discover. Experimental studies[47] suggest that the protonated nitrogen moiety interacts with the carboxyl group of Asp 147 to form a putative salt bridge. In detail, the molecule was docked in the upper level of transmembrane part in each receptor. The orientation of the molecule skeleton in the binding locus was mainly decided by: first, the putative ionic interaction between the tertiary amino group in naltrexone and the carboxylic group of aspartate on the transmembrane helix 3 in each opioid receptor (Asp147 in mu, Asp128 in delta and Asp138 in kappa); Second, the hydrophobic portion of the ligand intend to face the hydrophobic transmembrane helices while the hydrophilic portion to the more polar extracellular loop region. The ligand-receptor complex was minimized in gas phase first with the backbone of the receptor fixed, but all the side chain atoms were left unconstrained. The optimized conformation was then used as the initial configuration for the molecular dynamics simulations. A short-term steepest descent energy minimization (5,000 iterations) and dynamics simulation (10,000 step, 1 fs each step) was conducted to validate the docking primarily followed by a more vigorous minimizations (50,000 iterations) and dynamics simulation (100,000 steps) was conducted with 2000 steps equilibration for the initial dynamics. The total simulation time was 102 ps. In both processes, the backbone of the receptor was fixed to prevent the disruption of the α-helical bundle of the receptor and a generic distance constraint (4 to 4.2 Å) was applied between the negatively charged oxygen atom in aspartate on TM3 and the positively charged nitrogen atom in the ligand. After the dynamics simulation, the lowest energy conformation of the complex was extracted and saved for analysis.

Chemical Synthesis

General Methods: All reagents were purchased from Sigma-Aldrich or as otherwise states. Melting points were obtained with a Fisher scientific micro melting point apparatus and were uncorrected. All IR spectra were recorded on a Nicole Avatar 360 FT-IR Instruments. Proton (300 MHz) and Carbon-13 (75 MHz) nuclear magnetic resonance (NMR) spectra were recorded at ambient temperature with tetramethylsilane as the internal standard on either a Varian Gemini-300 MHz "Tesla" spectrometer or Varian Mercury-300 MHz NMR spectrometer. GC/MS analysis was performed on a Hewlett Packard 6890 (Palo Alto, Calif.). TLC analyses were carried out on the Analtech Uniplate F254 plates. Chromatographic purification was carried out on silica gel columns (230~400 mesh, Merck). Yields were not maximized. The final target compounds' purity was tested by HPLC and elemental analysis, and satisfying purity of >95% was achieved from both methods. Varian ProStar HPLC System was used on Microsorb-MV 100-5 C18 column (250×4.6 mm) with injection volume at 10 μL and sample concentrations at 1-2 mg/0.5 mL in 100% acetonitrile; The sample was detected at single wavelength of 210 nm with eluent system of acetonitrile:water (75:25) at 1 mL/min over 50 min. Elemental analysis was conducted in Atlantic Microlab, Inc. All spectral data reported here were obtained from the hydrochloride salt form of the products while compound 1-6 and 9-14 were dihydrochloride salts, and compound 7, 8, 15 and 16 monohydrochloride salts.

General procedure 1: A solution of 6α-naltrexamine or 6β-naltrexamine (1 equivalent) in $CH_2Cl_2$ was added acyl chloride (2 equivalent), and triethylamine (4 equivalent) on an ice-water bath under $N_2$ protection. The mixture was allowed to stir overnight at room temperature. After concentrated to remove $CH_2Cl_2$, the resulting residue was dissolved in MeOH and added potassium carbonate (2 equivalents). The reaction mixture was stirred overnight at room temperature. After concentrated, the residue was partitioned between water and $CH_2Cl_2$. The water layer was extracted with $CH_2Cl_2$. The combined $CH_2Cl_2$ solution was washed with brine, dried over $Na_2SO_4$. After concentrated, the residue was purified by silica gel column with a $CH_2Cl_2$/MeOH (100:1) (1% $NH_3H_2O$) solvent system as eluent to give the aim product. The product was then transferred into the hydrochloride salt using 1.25 M hydrochloride acid methanol solution at 0° C.

General procedure 2: A solution of carboxylic acid (3 equivalent) in DMF was added N-(3-Dimethylaminopropyl)-N'-ethylcarbodiimide hydrochloride (EDCI, 2.5 equivalent), hydrobenzotriazole (HOBt, 2.5 equivalent), 4 Å Molecular sieve, and triethylamine (5 equivalent) on an ice-water bath under $N_2$ protection. After 15 min, a solution of 6β-naltrexamine (1 equivalent) in DMF was added. The reaction mixture was filtered over celite after stirring overnight at room temperature. The filtrate was concentrated in vacuum to remove DMF. The residue was dissolved in MeOH and added potassium carbonate (2 equivalent). The resulting mixture was stirred overnight at room temperature. After concentrated, the residue was partitioned between water and $CH_2Cl_2$. The water layer was extracted with $CH_2Cl_2$. The combined $CH_2Cl_2$ solution was washed with $H_2O$, brine, dried with $Na_2SO_4$. After concentrated, the residue was purified by silica gel column with a $CH_2Cl_2$/MeOH (100:1) (1% $NH_3H_2O$) solvent system as eluent to give the aim product. Then the product was transferred into a hydrochloride salt.

17-Cyclopropylmethyl-3,14β-dihydroxy-4,5α-epoxy-6α-[(2'-pyridyl)acetamido]morphinan (1) was prepared by following the general procedure 1 in 58% yield. $[\alpha]^{25}_D$: −244° (c=0.05, MeOH). M.p.: 212-214° C.; IR (KBr, $cm^{-1}$) $v_{max}$: 3225, 1675, 1521, 1320; $^1$H NMR (300 MHz, DMSO): δ 8.90 (b, 1H, exchangeable), 8.71 (b, 1H, Amide-H), 8.39 (m, 1H, Ar—H), 8.09 (m, 2H, Ar—H), 7.68 (m, 1H, Ar—H), 6.77 and 6.62 (2 d, 1H each, J=8.1 Hz, $C_1$—H, $C_2$—H), 4.77 (m, 1H, $C_6$—H), 4.67 (m, 1H, $C_5$—H), 3.12 (d, J=6.3 Hz, 1H), 3.05 (d, J=18.6 Hz, 1H), 2.67 (m, 1H), 2.63 (m, 1H), 2.57 (m, 1H), 2.35 (m, 1H), 2.27 (m, 1H), 2.17 (m, 2H), 1.84 (m, 1H), 1.74 (m, 1H), 1.49 (m, 1H), 1.14 (m, 1H), 0.86 (m, 1H), 0.54 (m, 2H), 0.12 (m, 2H); $^{13}$C NMR (75 MHz, DMSO) δ: 163.88, 150.16, 148.34, 145.74, 137.79, 137.61, 130.10, 126.35, 125.99, 122.69, 119.41, 117.61, 90.45, 69.85, 62.36, 59.91, 47.49, 46.49, 43.39, 33.83, 29.45, 23.11, 21.17, 9.60, 4.21, 4.06; MS (ESI) m/z: 447.7 ($M^+$). Anal. ($C_{26}H_{29}N_3O_4.2HCl.1.5H_2O$) C, H.

17-Cyclopropylmethyl-3,14β-dihydroxy-4,5α-epoxy-6β-[(2'-pyridyl)acetamido]morphinan (2) was prepared by following the general procedure 1 in 65% yield. $[\alpha]^{25}_D$: −91° (c=0.07, MeOH). M.p.: 210-212° C.; IR (KBr, $cm^{-1}$) $v_{max}$: 3384 1673, 1526, 1324; $^1$H NMR (300 MHz, DMSO): δ 9.07 (b, 1H, Amide-H), 8.86 (b, 1H, exchangeable), 8.69 (m, 1H, Ar—H), 8.03 (m, 2H, Ar—H), 7.65 (m, 1H, Ar—H), 6.73 and 6.68 (2 d, 1H each, J=8.1 Hz, $C_1$—H, $C_2$—H), 5.02 (m, 1H, $C_6$—H), 4.62 (m, 1H, $C_5$—H), 3.10 (d, J=6.3 Hz, 1H), 3.03 (d, J=18.9 Hz, 1H), 2.65 (m, 1H), 2.63 (m, 1H), 2.58 (m, 1H), 2.37 (m, 2H), 2.25 (m, 1H), 2.19 (m, 1H), 1.95 (m, 1H), 1.82 (m, 1H), 1.61 (m, 1H), 1.45 (m, 1H), 0.84 (m, 1H), 0.54 (m, 2H), 0.12 (m, 2H); $^{13}$C NMR (75 MHz, DMSO) δ: 160.27, 145.86, 144.30, 138.97, 136.63, 133.54, 127.19, 122.39, 120.28, 118.59, 115.29, 114.35, 89.11, 66.42, 58.54, 55.44, 47.84, 43.91, 41.96, 40.30, 27.00, 26.22, 20.59, 18.88, 6.82, 5.68; MS (ESI) m/z: 448.1 $(M+H)^+$. Anal. ($C_{26}H_{29}N_3O_4.2HCl.3H_2O$) C, H.

17-Cyclopropylmethyl-3,14β-dihydroxy-4,5α-epoxy-6α-[(3'-pyridyl)acetamido]morphinan (3) was prepared by following the general procedure 1 in 54% yield. $[\alpha]^{25}_D$: −273° (c=0.06, MeOH). M.p.: 211-214° C.; IR (KBr, $cm^{-1}$) $v_{max}$: 3215, 1672, 1531, 1507, 1322; $^1$H NMR (300 MHz, DMSO): δ 9.23 (m, 1H, Ar—H), 8.94 (b, 1H, exchangeable), 8.92 (s, 1H, Amide-H), 8.75 (d, J=5.1 Hz, 1H, Ar—H), 8.66 (d, J=7.5 Hz, 1H, Ar—H), 7.89 (dd, J=5.1, 7.5 Hz, 1H, Ar—H), 6.73 and 6.58 (2 d, 1H each, J=8.1 Hz, $C_1$—H, $C_2$—H), 4.76 (m, 1H, C₅—H), 4.63 (m, 1H, C₆—H), 3.97 (m, 1H), 3.43 (m, 2H), 3.05 (m, 3H), 2.71 (m, 1H), 2.45 (m, 2H), 1.95 (m, 1H), 1.63 (m, 1H), 1.53 (m, 1H), 1.20 (m, 1H), 1.06 (m, 1H), 0.64 (m, 2H), 0.45 (m, 2H); $^{13}$C NMR (75 MHz, DMSO) δ: 165.25, 151.34, 147.83, 145.94, 138.43, 136.20, 131.16, 130.84, 125.51, 123.82, 119.56, 117.96, 89.49, 69.88, 62.38, 59.89, 47.28, 45.95, 43.45, 33.71, 29.32, 23.08, 21.38, 9.62, 4.20, 4.06; MS (ESI) m/z: 448.9 (M+H)$^+$. Anal. ($C_{26}H_{29}N_3O_4 \cdot 2HCl \cdot 3H_2O$) C, H.

17-Cyclopropylmethyl-3,14β-dihydroxy-4,5α-epoxy-6β-[(3'-pyridyl)acetamido]morphinan (4) was prepared by following the general procedure 1 in 56% yield. $[α]^{25}_D$: −141° (c=0.10, MeOH)). M.p.: 225-227° C.; IR (KBr, cm$^{-1}$) $ν_{max}$: 3207, 3057, 1665, 1540, 1326; $^1$H NMR (300 MHz, DMSO): δ 9.18 (m, 1H, Ar—H), 9.15 (b, 1H, Amide-H), 8.90 (b, 1H, exchangeable), 8.86 (m, 1H, Ar—H), 8.51 (m, 1H, Ar—H), 7.77 (m, 1H, Ar—H), 6.75 and 6.68 (2 d, 1H each, J=8.4 Hz, C₁—H, C₂—H), 4.85 (d, J=8.4 Hz, 1H, C₅—H), 4.47 (s, 1H, C₆—H), 3.89 (m, 1H), 3.73 (m, 1H), 3.38 (m, 1H), 3.12 (m, 2H), 2.85 (m, 1H), 2.45 (m, 2H), 1.93 (m, 1H), 1.80 (m, 1H), 1.64 (m, 1H), 1.47 (m, 2H), 1.09 (m, 1H), 0.64 (m, 2H), 0.46 (m, 2H); $^{13}$C NMR (75 MHz, DMSO) δ: 161.34, 147.63, 144.05, 139.39, 136.30, 131.90, 126.87, 126.46, 120.29, 119.68, 115.32, 114.28, 88.05, 66.55, 58.39, 55.48, 47.27, 41.88, 40.16, 27.77, 25.51, 19.75, 18.82, 6.98, 5.63, 3.26; MS (ESI) m/z: 448.9 (M+H)$^+$. Anal. ($C_{26}H_{29}N_3O_4 \cdot 2HCl \cdot 3H_2O$) C, H.

17-Cyclopropylmethyl-3,14β-dihydroxy-4,5α-epoxy-6α-[(4'-pyridyl)acetamido]morphinan (5) was prepared by following the general procedure 1 in 45% yield. $[α]^{25}_D$: −213° (c=0.09, MeOH). M.p. 215-217° C.; IR (KBr, cm$^{-1}$) $ν_{max}$: 3225, 1653, 1542, 1500, 1318; $^1$H NMR (300 MHz, DMSO): δ 8.92 (m, 2H, Ar—H), 8.88 (b, 1H, exchangeable), 8.77 (b, 1H, Amide-H), 8.08 (m, 2H, Ar—H), 6.73 and 6.59 (2 d, 1H each, J=8.1 Hz, C₁—H, C₂—H), 4.78 (m, 1H, C₅—H), 4.62 (m, 1H, C₆—H), 3.95 (m, 1H), 3.40 (m, 2H), 3.06 (m, 2H), 2.74 (m, 1H), 2.46 (m, 2H), 1.91 (m, 1H), 1.65 (m, 1H), 1.52 (m, 1H), 1.18 (m, 2H), 1.09 (m, 1H), 0.69 (m, 2H), 0.49 (m, 2H); $^{13}$C NMR (75 MHz, DMSO) δ: 164.17, 149.72, 149.72, 145.15, 142.08, 137.77, 130.25, 124.71, 121.12, 121.12, 119.07, 117.28, 88.82, 69.06, 61.74, 59.26, 46.81, 46.54, 45.27, 42.58, 33.29, 28.70, 22.43, 8.17, 7.55, 3.56; MS (ESI) m/z: 448.9 (M+H)$^+$. Anal. ($C_{26}H_{29}N_3O_4 \cdot 2HCl \cdot 3H_2O$) C, H.

17-Cyclopropylmethyl-3,14β-dihydroxy-4,5α-epoxy-6β-[(4'-pyridyl)acetamido]morphinan (6, NAP) was prepared following the general procedure 1 in 45% yield. $[α]^{25}_D$: −176° (c=0.01, MeOH). M.p.: 258-61° C.; IR (KBr, cm$^{-1}$) $ν_{max}$: 3386, 1666, 1548, 1502, 1326; $^1$H NMR (300 MHz, DMSO): δ 8.81 (b, 1H, Amide-H), 8.45 (m, 2H, Ar—H), 8.22 (b, 1H, exchangeable), 7.60 (m, 2H, Ar—H), 6.32 and 6.27 (2 d, 1H each, J=7.8 Hz, C₁—H, C₂—H), 4.84 (s, 1H, C₅—H), 4.46 (m, 1H, C₆—H), 3.90 (m, 1H), 3.69 (m, 1H), 3.30 (m, 2H), 3.06 (m, 2H), 2.85 (m, 1H), 2.45 (m, 2H), 1.93 (m, 1H), 1.80 (m, 1H), 1.59 (m, 1H), 1.46 (m, 1H), 1.07 (m, 1H), 0.63 (m, 2H), 0.45 (m, 2H); $^{13}$C NMR (75 MHz, DMSO) δ: 164.30, 149.27, 142.72, 139.62, 130.15, 128.61, 127.80, 124.87, 123.73, 120.89, 118.86, 117.84, 91.15, 69.90, 61.75, 58.84, 50.68, 46.91, 43.50, 39.98, 31.10, 28.60, 22.18, 8.99, 3.68, 3.37; MS (ESI) m/z: 448.9 (M+H)$^+$. Anal. ($C_{26}H_{29}N_3O_4 \cdot 2HCl \cdot 3H_2O$) C, H.

17-Cyclopropylmethyl-3,14β-dihydroxy-4,5α-epoxy-6α-(benzamido)morphinan (7) was prepared by following the general procedure 1 in 54% yield. $[α]^{25}_D$: −215° (c=0.11, MeOH). M.p.: 182-185° C.; IR (KBr, cm$^{-1}$) $ν_{max}$: 3353, 2947, 1638, 1540, 1324; $^1$H NMR (300 MHz, DMSO): δ 7.75 (m, 2H, Ar—H), 7.45 (m, 3H, Ar—H), 6.70 and 6.65 (2 d, 1H each, J=8.4 Hz, C₁—H, C₂—H), 6.50 (b, 1H, Amide-H), 4.79 (m, 1H, C₆—H), 4.77 (m, 1H, C₅—H), 3.14 (m, 1H), 3.04 (m, 1H), 2.68 (m, 1H), 2.65 (m, 1H), 2.60 (m, 1H), 2.36 (m, 1H), 2.29 (m, 1H), 2.27 (m, 2H), 1.84 (m, 1H), 1.58 (m, 1H), 1.42 (m, 1H), 1.25 (m, 1H), 0.86 (m, 1H), 0.54 (m, 2H), 0.12 (m, 2H); $^{13}$C NMR (75 MHz, DMSO) δ: 167.72, 145.85, 138.14, 134.53, 131.57, 131.11, 128.60, 127.47, 125.63, 119.38, 117.86, 90.12, 69.91, 62.32, 59.87, 47.38, 46.98, 43.39, 33.69, 29.45, 23.11, 21.17, 9.56, 4.24, 4.08; MS (ESI) m/z: 447.9 (M+H)$^+$. Anal. ($C_{27}H_{30}N_2O_4 \cdot HCl \cdot 2.75H_2O$) C, H.

17-Cyclopropylmethyl-3,14β-dihydroxy-4,5α-epoxy-6β-(benzamido)morphinan (8) was prepared by following the general procedure 1 in 59% yield. $[α]^{25}_D$: −157° (c=0.07, MeOH). M.p.: 220-221° C.; IR (KBr, cm$^{-1}$) $ν_{max}$: 3242, 1638, 1540, 1324; $^1$H NMR (300 MHz, DMSO): δ 7.84 (m, 2H, Ar—H), 7.50-7.40 (m, 3H, Ar—H), 7.21 (b, 1H, Amide-H), 6.75 and 6.58 (2 d, 1H each, J=8.1 Hz, C₁—H, C₂—H), 4.52 (m, 1H, C₅—H), 4.26 (m, 1H, C₆—H), 3.87 (m, 1H), 3.73 (m, 1H), 3.15 (m, 1H), 2.69 (m, 1H), 2.61 (m, 1H), 2.40 (m, 1H), 2.23 (m, 2H), 1.87 (m, 1H), 1.72 (m, 1H), 1.55 (m, 1H), 1.26 (m, 1H), 1.12 (m, 1H), 0.86 (m, 1H), 0.54 (m, 2H), 0.12 (m, 2H); $^{13}$C NMR (75 MHz, DMSO) δ: 168.79, 142.59, 140.78, 134.52, 131.55, 131.18, 128.38, 127.23, 123.87, 119.04, 117.62, 91.82, 70.59, 62.61, 58.92, 52.14, 44.49, 30.45, 30.11, 29.66, 24.35, 22.52, 8.76, 3.61, 3.05; MS (EST) m/z: 447.9 (M+H)$^+$. Anal. ($C_{27}H_{30}N_2O_4 \cdot HCl \cdot 3.25H_2O$) C, H.

17-Cyclopropylmethyl-3,14β-dihydroxy-4,5α-epoxy-6α-[(3'-isoquinolyl)acetamido]morphinan (9, NAQ) was prepared by following the general procedure 2 in 70% yield. $[α]^{25}_D$: −150° (c=0.01, MeOH). M.p.: 210-213° C.; IR (KBr, cm$^{-1}$) $ν_{max}$: 3222, 1666, 1529, 1261, 801; $^1$H NMR (300 MHz, DMSO): δ 9.44 (s, 1H, Ar—H), 8.95 (b, 1H, exchangeable), 8.64 (s, 1H, Ar—H), 8.58 (b, 1H, Amide-H), 8.27 (m, 2H, Ar—H), 7.90 (m, 2H, Ar—H), 6.79 and 6.62 (2 d, 1H each, J=7.8 Hz, C₁—H, C₂—H), 4.81 (s, 1H, C₅—H), 4.74 (m, 1H, C₆—H), 3.99 (m, 1H), 3.45 (m, 2H), 3.14 (m, 2H), 2.73 (m, 1H), 2.58 (m, 1H), 2.23 (m, 2H), 1.87 (m, 1H), 1.67 (m, 2H), 1.48 (m, 1H), 1.08 (m, 1H), 0.67 (m, 2H), 0.47 (m, 2H); $^{13}$C NMR (75 MHz, DMSO) δ: 159.97, 148.87, 146.15, 139.18, 138.21, 137.40, 134.48, 132.47, 131.01, 128.93, 128.86, 128.37, 124.16, 122.44, 120.07, 118.39, 87.91, 69.86, 62.26, 57.93, 47.15, 46.05, 30.51, 29.43, 23.88, 19.57, 19.56, 5.75, 5.18, 2.26; MS (ESI) m/z: 498.1 (M+H)$^+$, Anal. ($C_{30}H_{31}N_3O_4 \cdot 2HCl \cdot 0.5H_2O$) C, H.

17-Cyclopropylmethyl-3,14β-dihydroxy-4,5α-epoxy-6β-[(3'-isoquinolyl)acetamido]morphinan (10) was prepared by following the general procedure 2 in 50% yield. $[α]^{25}_D$: −166° (c=0.10, MeOH)). M.p.: 235-237° C.; IR (KBr, cm$^{-1}$) $ν_{max}$: 3069, 1665, 1537, 1328, 901; $^1$H NMR (300 MHz, DMSO): δ 9.46 (s, 1H, Ar—H), 927 (b, 1H, Amide-H), 9.15 (s, 1H, Ar—H), 8.92 (b, 1H, exchangeable), 8.21 (m, 2H, Ar—H), 8.00 (m, 1H, Ar—H), 7.81 (m, 1H, Ar—H), 6.76 and 6.68 (2 d, 1H each, J=8.4 Hz, C₁—H, C₂—H), 5.06 (m, 1H, C₆—H), 4.90 (d, J=7.8 Hz, 1H, C₅—H), 3.91 (m, 1H), 3.78 (m, 1H), 3.37 (m, 2H), 3.10 (m, 2H), 2.89 (m, 1H), 2.45 (m, 1H), 2.00 (m, 1H), 1.83 (m, 1H), 1.69 (m, 1H), 1.49 (m, 2H), 1.12 (m, 1H), 0.68 (m, 2H), 0.48 (m, 2H); $^{13}$C NMR (75 MHz, DMSO) δ: 164.63, 151.51, 143.09, 142.94, 140.57, 135.84, 131.37, 131.26, 129.64, 129.01, 128.16, 128.06, 124.62, 120.53, 119.48, 118.30, 92.95, 62.55, 59.43, 52.26, 44.35, 36.71, 31.66, 30.85, 30.42, 24.69, 22.92, 9.68, 4.22, 4.02; MS (ESI) m/z: 498.8 (M+H)$^+$. Anal. ($C_{30}H_{31}N_3O_4 \cdot 2HCl \cdot 3.5H_2O$) C, H.

17-Cyclopropylmethyl-3,14β-dihydroxy-4,5α-epoxy-6α-[(2'-quinolyl)acetamido]morphinan (11) was prepared by following the general procedure 1 in 93% yield. The product was transferred into a HCl salt. $[α]^{25}_D$: −186° (c=0.03, MeOH). M.p.: 212-214° C.; IR (KBr, cm$^{-1}$) $v_{max}$: 3199, 1673, 1528, 1321, 785; $^1$H NMR (300 MHz, DMSO): δ 8.90 (b, 1H, Amide-H), 8.60 (m, 2H, Ar—H), 8.21 (b, 1H, exchangeable), 8.13 (m, 2H, Ar—H), 7.92 (m, 1H, Ar—H), 7.75 (m, 1H, Ar—H), 6.76 and 6.63 (2 d, 1H each, J=7.8 Hz, C$_1$—H, C$_2$—H), 4.84 (s, 1H, C$_5$—H), 4.68 (m, 1H, C$_6$—H), 3.94 (m, 1H), 3.65 (m, 1H), 3.35 (m, 1H), 3.05 (m, 1H), 2.71 (m, 1H), 2.45 (m, 2H), 1.93 (m, 2H), 1.82 (m, 1H), 1.65 (m, 1H), 1.48 (m, 2H), 1.06 (m, 1H), 0.63 (m, 2H), 0.44 (m, 2H); $^{13}$C NMR (75 MHz, DMSO) δ: 160.77, 146.72, 146.08, 145.15, 141.05, 139.27, 134.49, 134.49, 130.24, 130.24, 128.88, 123.95, 122.35, 120.10, 119.33, 118.51, 87.79, 69.88, 62.24, 57.95, 47.18, 46.06, 30.51, 29.42, 23.91, 19.68, 19.68, 5.79, 5.22, 2.31; MS (ESI) m/z: 498.1 (M+H)$^+$. Anal. (C$_{30}$H$_{31}$N$_3$O$_4$.2HCl.2.5H$_2$O) C, H.

17-Cyclopropylmethyl-3,14β-dihydroxy-4,5α-epoxy-6β-[(2'-quinolyl)acetamido]morphinan (12) was prepared by following the general procedure 1 in 83% yield. [α]$^{25}_D$: −112° (c=0.1, MeOH). M.p.: 227-229° C.; IR (KBr, cm$^{-1}$) $v_{max}$: 3110, 1671, 1533, 1329, 770; $^1$H NMR (300 MHz, DMSO): δ 9.26 (m, 1H, Ar—H), 8.94 (b, 1H, Amide-H), 8.61 (m, 1H, Ar—H), 8.16 (m, 2H, Ar—H), 8.12 (b, 1H, exchangeable), 7.92 (m, 1H, Ar—H), 7.78 (m, 1H, Ar—H), 6.79 and 6.68 (2 d, 1H each, J=7.8 Hz, C$_1$—H, C$_2$—H), 5.15 (s, 1H, C$_5$—H), 5.12 (m, 1H, C$_6$—H), 3.93 (m, 1H), 3.77 (m, 1H), 3.43 (m, 1H), 3.10 (m, 2H), 2.90 (m, 1H), 2.45 (m, 2H), 2.09 (m, 1H), 1.83 (m, 1H), 1.62 (m, 1H), 1.48 (m, 1H), 1.08 (m, 1H), 0.86 (m, 1H), 0.65 (m, 2H), 0.50 (m, 2H); $^{13}$C NMR (75 MHz, DMSO) δ: 163.98, 149.09, 145.84, 141.98, 139.75, 136.87, 130.48, 129.60, 129.12, 128.72, 127.40, 127.26, 123.60, 118.64, 118.44, 117.41, 93.02, 69.83, 61.83, 58.76, 51.23, 47.33, 43.66, 30.11, 29.71, 24.20, 22.20, 8.99, 3.62, 3.36; MS (ESI) m/z: 497.8 (M+H)$^+$. Anal. (C$_{30}$H$_{31}$N$_3$O$_4$.2HCl.0.5H$_2$O) C, H.

17-Cyclopropylmethyl-3,14β-dihydroxy-4,5α-epoxy-6α-[(3'-quinolyl)acetamido]morphinan (13) was prepared by following the general procedure 2 in 61% yield: [α]$^{25}_D$: −192° (c=0.05, MeOH). M.p.: >270° C.; IR (KBr, cm$^{-1}$) $v_{max}$: 3221, 1660, 1537, 1318, 777; $^1$H NMR (300 MHz, DMSO): δ 9.39 (s, 1H, Ar—H), 9.06 (s, 1H, Ar—H), 8.90 (b, 1H, Amide-H), 8.66 (b, 1H, exchangeable), 8.19 (m, 2H, Ar—H), 7.97 (m, 1H, Ar—H), 7.79 (m, 1H, Ar—H), 6.73 and 6.59 (2 d, 1H each, J=8.1 Hz, C$_1$—H, C$_2$—H), 4.83 (m, 1H, C$_5$—H), 4.70 (m, 1H, C$_6$—H), 3.95 (m, 1H), 3.45 (m, 2H), 3.08 (m, 3H), 2.72 (m, 1H), 2.52 (m, 2H), 1.92 (m, 1H), 1.65 (m, 1H), 1.51 (m, 1H), 1.26 (m, 1H), 1.10 (m, 1H), 0.68 (m, 2H), 0.45 (m, 2H); $^{13}$C NMR (75 MHz, DMSO) δ: 164.04, 147.59, 146.84, 144.48, 141.03, 139.52, 134.19, 130.41, 129.48, 128.03, 127.76, 125.83, 122.91, 119.93, 119.24, 116.95, 87.73, 70.15, 61.65, 57.70, 47.08, 45.99, 39.40, 30.92, 29.83, 24.30, 20.10, 6.50, 5.99, 3.34; MS (ESI) m/z: 498.9 (M+H)$^+$. Anal. (C$_{30}$H$_{31}$N$_3$O$_4$.2HCl.3.75H$_2$O) C, H.

17-Cyclopropylmethyl-3,14β-dihydroxy-4,5α-epoxy-6β-[(3'-quinolyl)acetamido]morphinan (14) was prepared by following the general procedure 2 in 87% yield. [α]$^{25}_D$: −86° (c=0.07, MeOH). M.p.: 235-238° C.; IR (KBr, cm$^{-1}$) $v_{max}$: 3072, 1660, 1549, 1324, 777; $^1$H NMR (300 MHz, DMSO): δ 9.47 (s, 1H, Ar—H), 9.35 (b, 1H, Amide-H), 8.92 (b, 1H, exchangeable), 8.23 (m, 2H, Ar—H), 8.22 (s, 1H, Ar—H), 8.03 (m, 2H, Ar—H), 6.76 and 6.68 (2 d, 1H each, J=8.4 Hz, C$_1$—H, C$_2$—H), 5.11 (s, 1H, C$_5$—H) 5.01 (m, 1H, C$_6$—H), 3.92 (m, 1H), 3.78 (m, 1H), 3.33 (m, 2H), 3.07 (m, 2H), 2.89 (m, 1H), 1.83 (m, 1H), 1.62 (m, 2H), 1.46 (m, 3H), 1.11 (m, 1H), 0.65 (m, 2H), 0.47 (m, 2H); $^{13}$C NMR (75 MHz, DMSO) δ: 165.68, 147.82, 147.72, 141.71, 140.27, 135.74, 131.00, 130.18, 128.40, 127.21, 127.04, 126.69, 126.50, 122.65, 118.42, 116.87, 99.79, 69.75, 61.90, 57.95, 51.63, 46.22, 44.11, 29.40, 29.24, 23.49, 21.82, 7.55, 2.99, 2.10; MS (ESI) m/z: 498.8 (M+H)$^+$. Anal. (C$_{30}$H$_{31}$N$_3$O$_4$.2HCl.2.5H$_2$O) C, H.

17-Cyclopropylmethyl-3,14β-dihydroxy-4,5α-epoxy-6α-[(2'-naphthalyl)acetamido]morphinan (15) was prepared by following the general procedure 1 in 46% yield. [α]$^{25}_D$: −218° (c=0.01, MeOH). M.p.: 213-215° C.; IR (KBr, cm$^{-1}$) $v_{max}$: 3399, 1641, 1503, 1460, 1318; $^1$H NMR (300 MHz, DMSO): δ 8.15 (s, 1H, Ar—H), 7.77-7.73 (m, 4H, Ar—H), 7.45 (m, 2H, Ar—H), 6.85 (b, 1H, Amide-H), 6.85 and 6.50 (2 d, 1H each, J=8.1 Hz, C$_1$—H, C$_2$—H), 4.80 (m, 1H, C$_6$—H), 4.71 (m, 1H, C$_5$—H), 3.69 (m, 1H), 3.00 (m, 1H), 2.63 (m, 1H), 2.53 (m, 1H), 2.34 (m, 1H), 2.23 (m, 1H), 2.15 (m, 2H), 1.76 (m, 1H), 1.49 (m, 1H), 1.36 (m, 1H), 1.09 (m, 1H), 1.14 (m, 1H), 0.83 (m, 1H), 0.55 (m, 2H), 0.12 (m, 2H); $^{13}$C NMR (75 MHz, CD$_3$OD) δ: 167.96, 145.46, 138.32, 134.35, 132.03, 130.76, 128.13, 127.44, 127.37, 127.25, 127.17, 127.00, 125.98, 123.30, 121.61, 119.24, 117.59, 87.72, 61.56, 57.25, 44.50, 39.95, 37.39, 29.81, 28.96, 23.29, 18.95, 13.60, 9.87, 5.05, 4.55; MS (ESI) m/z: 496.8 (M$^+$). Anal. (C$_{31}$H$_{32}$N$_2$O$_4$.HCl.1.5H$_2$O) C, H.

17-Cyclopropylmethyl-3,14β-dihydroxy-4,5α-epoxy-6β-[(2'-naphthalyl)acetamido]morphinan (16) was prepared by following the general procedure 1 in 44% yield. [α]$^{25}_D$: −123° (c=0.09, MeOH). M.p.: 212-215° C.; IR (KBr, cm$^{-1}$) $v_{max}$: 3248, 2964, 1640, 1508, 1319, 716; $^1$H NMR (300 MHz, DMSO): δ 8.36 (b, 1H, Amide-H), 7.95-7.86 (m, 5H, Ar—H), 7.56 (m, 2H, Ar—H), 6.76 and 6.59 (2 d, 1H each, J=8.4 Hz, C$_1$—H, C$_2$—H), 4.60 (m, 1H, C$_5$—H), 4.31 (m, 1H, C$_6$—H), 3.88 (m, 1H), 3.75 (m, 1H), 3.19 (m, 1H), 2.70 (m, 1H), 2.42 (m, 1H), 2.27 (m, 2H), 1.96 (m, 1H), 1.70 (m, 1H), 1.54 (m, 1H), 1.24 (m, 1H), 1.49 (m, 1H), 1.14 (m, 1H), 0.88 (m, 1H), 0.50 (m, 2H), 0.12 (m, 2H); $^{13}$C NMR (75 MHz, DMSO) δ: 166.36, 147.21, 142.86, 134.85, 132.86, 131.80, 129.57, 128.98, 128.57, 128.35, 128.25, 128.24, 127.48, 124.85, 121.75, 119.20, 119.10, 91.30, 70.44, 62.43, 51.74, 42.96, 35.67, 33.08, 32.17, 30.45, 24.70, 20.10, 9.50, 6.80, 4.00; MS (ESI) m/z: 497.8 (M+H)$^+$. Anal. (C$_{31}$H$_{32}$N$_2$O$_4$.HCl.H$_2$O) C, H.

In vitro competitive radioligand-binding and functional assay Details of the binding assay was conducted to study the selectivity of the ligands by using mono-cloned opioid receptor expressed in Chinese hamster ovarian (CHO) cell lines as described previously.[44,45] [$^3$H]naloxone, [$^3$H]NTI and [$^3$H]norBNI were used to label the mu, delta and kappa opioid receptors respectively. Aliquots of a membrane preparation were incubated with the radioligands in the presence of different concentrations of the drug under investigation at 30° C. for 1 h. Specific (i.e. opioid receptor related) binding was determined as the difference in binding obtained in the absence and presence of 10 μM naltrexone. The potency of the drugs in displacing the specific binding of the radioligand was determined from data using linear regression analysis of Hill plots. The IC$_{50}$ values will then be determined and corrected to K$_i$ values using the Cheng-Prusoff equation. Functional assays, including $^{35}$S-GTP[γS]-binding assay were conducted in the same cell membranes used for the receptor binding assays. 3 μM of DAMGO was included in the assay for a maximally effective concentration of a full agonist for the mu opioid receptor.

In Vivo Acute Function Test Procedure

Animals. Male Swiss Webster mice (Harlan Laboratories, Indianapolis, Ind.) weighing 25-30 g were housed 6 to a cage in animal care quarters and maintained at 22±2° C. on a 12 hr light-dark cycle. Food and water were available ad libitum. The mice were brought to a test room (22±2° C., 12 hr light-dark cycle), marked for identification and allowed 18 hr to recover from transport and handling. Protocols and procedures were approved by the Institutional Animal Care and Use Committee (IACUC) at Virginia Commonwealth University Medical Center and comply with the recommendations of the IASP (International Association for the Study of Pain).

Tail immersion test. The warm-water tail immersion test was performed according to Coderre and Rollman[58] using a water bath with the temperature maintained at 56±0.1° C. Before injecting the mice, a base-line (control) latency was determined. Only mice with a control reaction time from 2 to 4 second were used. The average baseline latency for these experiments was 3.0±0.1 sec. The test latency after drug treatment was assessed at the appropriate time, and a 10 second maximum cut-off time was imposed to prevent tissue damage. Antinociception was quantified according to the method of Harris and Pierson[59] as the percentage of maximum possible effect (% MPE) which was calculated as: % MPE=[(test latency−control latency)/(10−control latency)]× 100. Percent MPE was calculated for each mouse using at least 6 mice per drug.

Drugs. Morphine sulfate was purchased from Mallinckrodt, St. Louis, MQ USA. Naloxone was purchased from Sigma-Aldrich (St. Louis, Mo., USA). All drugs and test compounds were dissolved in pyrogen-free isotonic saline (Baxter Healthcare, Deerfield, Ill.) and were administered to mice subcutaneously (s.c.)

Experimental design and statistical analysis. To test for agonist properties, mice, with pre-determined tail immersion baseline, were injected s.c. with morphine (10 mg/kg; a dose that produces maximal antinociception) or the test compound at increasing doses and were re-assessed for their tail immersion reaction time 20 min later. To test for antagonist properties, mice, with pre-determined tail immersion baseline, were injected s.c. with either naloxone (1 mg/kg; a dose that totally block the antinociception induce by 10 mg/kg morphine) or the test compound at various doses and 5 min later they were administered morphine (10 mg/kg; s.c.). Mice were re-assessed for their tail immersion reaction time 20 min later. Effective dose-50 (ED50) values were calculated using least-squares linear regression analysis followed by calculation of 95% confidence limits (95% C.L.) by the method of Bliss.[60]

Data are expressed as mean values±S.E.M. Analysis of variance (ANOVA) followed by the post hoc "Student-Newman-Keuls" test were performed to assess significance using the Instat 3.0 software (GraphPad Software, San Diego, Calif., U.S.A.). P<0.05 was considered significant.

REFERENCES FOR EXAMPLE 2

1. Zimmerman, D. M.; Leander, J. D. Selective opioid receptor agonists and antagonists: research tools and potential therapeutic agents. J. Med. Chem. 1990, 33, 895-902.
2. Schmidhammer, H. Opioid Receptor Antagonists, Prog. Med. Chem., 1998, 35, 83-132.
3. Snyder, S. H.; Pasternak. G. W. Historical review: Opioid Receptors. TRENDs Pharmacol. Sci., 2003, 24(4), 198-205.
4. Fiellin, D. A.; Kleber, H.; Trumble-Hejduk, J. G.; McLellan, A. T.; Kosten, T. R. Consensus statement in office-based treatment of opioid dependence using buprenorphine, J. Subst. Abuse Treat. 2004, 27, 153-159.
5. Gold, M. S.; Dackis, C. A.; Pottash, A. L.; Sternbach, H. H.; Annitto, W. J.; Martin, D.; Dackis, M. P. Naltrexone, opiate addiction, and endorphins. Med. Res. Rev. 1982, 2(3), 211-46.
6. Gonzalez, J. P.; Brogden, R. N. Naltrexone. A review of its pharmacodynamic and pharmacokinetic properties and therapeutic efficacy in the management of opioid dependence. Drugs, 1988, 35, 192-213.
7. Schwyzer, R. ACTH: a short introductory review. Ann. NY. Acad. Sci., 1977, 297, 3-26.
8. Portoghese, P. S.; Lipkowski, A. W.; Takemori, A. E. Binaltorphimine and nor-binaltorphimine, potent and selective kappa opioid receptor antagonists. Life Sci. 1987, 40, 1287-92.
9. Jones, R. M.; Hjorth, S. A.; Schwartz, T. W. Portoghese, P. S. Mutational evidence for a common kappa antagonist binding pocket in the wild-type kappa and mutant mu[K303E] opioid receptors. J. Med. Chem. 1998, 41(25), 4911-4.
10. Portoghese, P. S.; Sultana, M.; Nagase, H. Takemori, A. E. Application of the message-address concept in the design of highly potent and selective non-peptide delta opioid receptor antagonist. J. Med. Chem., 1988, 31, 281-82.
11. Schmidhammer, H.; Burkard, W. P.; Eggstin-Aeppli, L.; Smith, C. F. C. Synthesis and biological evaluation of 14-alkoxymorphinans. 2. (−)-N-(cyclopropymethyl)-4,14-dimethoxymorphinana-6-one, a selective mu opioid receptor antagonist. J. Med. Chem., 1989, 32, 418-421.
12. Marki, A.; Monory, K.; Otvos, F.; Toth, G.; Krassnig, R.; Schmidhammer, H.; Traynor, J. R.; Rogues, B. P.; Maldonado, R.; Borsodi, A. Mu-opioid receptor specific antagonist cyprodime: characterization by in vitro radioligand and [35S]GTPgammaS binding assays. Eur. J Pharmacol. 1999, 383(2), 209-14.
13. Schmidhammer, H.; Jennewein, H. K.; Krassnig, R.; Traynor, J. R.; Patel, D.; Bell, K.; Froschauer, G.; Mattersberger, K.; Jachs-Ewinger, C.; Jura, P.; Fraser, G. L.; Kalinin, V. N. Synthesis and biological evaluation of 14-alkoxymorphinans. 11. 3-Hydroxycyprodime and analogues: opioid antagonist profile in comparison to cyprodime. J. Med. Chem. 1995, 38(16), 3071-7.
14. Schmidhammer, H.; Jennewein, H. K.; Smith, C. F. Synthesis and biological evaluation of 14-alkoxymorphinans. 11. 3-Hydroxycyprodime and analogues: opioid antagonist profile in comparison to cyprodime. Arch. Pharm. (Weinheim). 1991, 324(4), 209-11.
15. Schmidhammer, H.; Smith, C. F.; Erlach, D.; Koch, M.; Krassnig, R.; Schwetz, W.; Wechner, C. Synthesis and biological evaluation of 14-alkoxymorphinans. 3. Extensive study on cyprodime-related compounds. J. Med. Chem. 1990, 33(4), 1200-6.
16. Schmidhammer, H.; Smith, C. F.; Erlach, D.; Koch, M.; Krassnig, R.; Schwetz, W., Wechner, C. Cyprodime analogues: synthesis and pharmacological evaluation. Prog. Clin. Biol. Res. 1989, 328, 37-40.
17. Spetea, M.; Schullner, F.; Moisa, R. C.; Berzetei-Gurske, I. P.; Schraml, B.; Dorfler, C.; Aceto, M. D.; Harris, L. S.; Coop, A.; Schmidhammer, H. Synthesis and biological evaluation of 14-alkoxymorphinans. 21. Novel 4-alkoxy and 14-phenylpropoxy derivatives of the mu opioid receptor antagonist cyprodime. J. Med. Chem. 2004, 47(12), 3242-7.
18. Lewis, J. W.; Smith, C. F. C.; McCarthy, P. S.; Walter, D.; Kobylecki, R. J.; Myers, M.; Haynes, A. S.; Lewis, C. J.; Waltham, K. New 14-aminomorphinones and codeinones. NIDA Res. Monogr. 1988, 90, 136-143.
19. Portoghese, P. S.; Takemori, A. E. Affinity labels as probes for opioid receptor types and subtypes. NIDA Res. Monogr. 1986, 69, 157-68.
20. Burke, T. F.; Woods, J. H.; Lewis, S. W.; Medzihradsky, F. Irreversible opioid antagonist effects of clocinnamox on opioid analgesia and mu receptor binding in mice. J. Pharmacol. Exp. Ther. 1994, 271(2), 715-21.

21. Eguchi, M. Recent advances in selective opioid receptor agonists and antagonists. Med. Res. Rev., 2004, 24(2), 182-212.
22. Pelton, J. T.; Kazmierski, W.; Gulya, K.; Yamamura, H. I.; Hruby, V. J. Design and synthesis of conformationally constrained somatostatin analogues with high potency and specificity for mu opioid receptors. J Med Chem. 1986, 29, 2370-5.
23. Gulya, K.; Pelton, J. T.; Hruby, V. J.; Yamamura, H. I. Cyclic somatostatin octapeptide analogues with high affinity and selectivity toward mu opioid receptors. Life Sci. 1986, 38, 2221-30.
24. Hawkins, K. N.; Knapp, R. J.; Lui, G. K.; Gulya, K.; Kazmierski, W.; Wan, Y. P.; Pelton, J. T.; Hruby, V. J.; Yamamura, H. I. [3H]-[H-D-Phe-Cys-Tyr-D-Trp-Orn-Thr-Pen-Thr-NH2] ([3H]CTOP), a potent and highly selective peptide for mu opioid receptors in rat brain. J Pharmacol Exp Ther. 1989, 248(1), 73-81.
25. Kramer, T. H.; Shook, J. E.; Kazmierski, W.; Ayres, E. A.; Wire, W. S.; Hruby, V. J.; Burks, T. F. Novel peptidic mu opioid antagonists: pharmacologic characterization in vitro and in vivo. J Pharmacol Exp Ther. 1989, 249(2), 544-51.
26. Hruby, V. J.; Toth, G.; Gehrig, C. A.; Kao, L. F.; Knapp, R.; Lui, G. K.; Yamamura, H. I.; Kramer, T. H.; Davis, P.; Burks, T. F. Topographically designed analogues of [D-Pen,D-Pen5]enkephalin. J Med Chem. 1991, 34(6), 1823-30.
27. Mulder, A. H.; Wardeh, G.; Hogenboom, F.; Kazmierski, W.; Hruby, V. J.; Schoffelmeer, A. N. Cyclic somatostatin analogues as potent antagonists at mu-, but not delta- and kappa-opioid receptors mediating presynaptic inhibition of neurotransmitter release in the brain. Eur J Pharmacol. 1991, 205(1), 1-6.
27. Abbruscato, T. S.; Thomas, S. A.; Hruby, V. J.; Davis, T. P. Blood-brain barrier permeability and bioavailability of a highly potent and mu-selective opioid receptor antagonist, CTAP: comparison with morphine. J Pharmacol Exp Ther. 1997, 280(1), 402-9.
28. Bonner, G. G.; Davis, P.; Stropova, D.; Edsall, S.; Yamamura, H. I.; Porreca, F.; Hruby, V. J. Opiate aromatic pharmacophore structure-activity relationships in CTAP analogues determined by topographical bias, two-dimensional NMR, and biological activity assays. J Med Chem. 2000, 43(4), 569-80.
29. Okada, T.; Le Trong, I.; Fox, B. A.; Behnke, C. A.; Stenkamp, R. E.; Palczewski, K. X-Ray diffraction analysis of three-dimensional crystals of bovine rhodopsin obtained from mixed micelles. J. Struct. Biol. 2000, 130(1), 73-80.
30. Teller, D. C.; Okada, T.; Behnke, C. A.; Palczewski, K.; Stenkamp, R. E. Advances in determination of a high-resolution three-dimensional structure of rhodopsin, a model of G-protein-coupled receptors (GPCRs). Biochemistry. 2001, 40(26), 7761-72.
31. Salom, D.; Le Trong, I.; Pohl, E.; Ballesteros, J. A.; Stenkamp, R. E.; Palczewski, K.; Lodowski, D. T. Improvements in G protein-coupled receptor purification yield light stable rhodopsin crystals. J. Struct. Biol. 2006, 156(3), 497-504.
32. Salom, D.; Lodowski, D. T.; Stenkamp, R. E.; Le Trong, I.; Golczak, M.; Jastrzebska, B.; Harris, T.; Ballesteros, J. A.; Palczewski, K. Crystal structure of a photoactivated deprotonated intermediate of rhodopsin. Proc. Natl. Acad. Sci. USA. 2006, 103(44), 16123-8.
33. Park, J. H.; Scheerer, P.; Hofmann, K. P.; Choe, H. W.; Ernst, O. P. Crystal structure of the ligand-free G-protein-coupled receptor opsin. Nature. 2008, 454, 183-7.
34. Rasmussen, S. G.; Choi, H. J.; Rosenbaum, D. M.; Kobilka, T. S.; Thian, F. S.; Edwards, P. C.; Burghammer, M.; Ratnala, V. R.; Sanishvili, R.; Fischetti, R. F.; Schertler, G. F.; Weis, W. I.; Kobilka, B. K. Crystal structure of the human beta(2) adrenergic G-protein-coupled receptor. Nature, 2007, 450(7168), 383-7.
35. Rosenbaum, D. M.; Cherezov, V.; Hanson, M. A.; Rasmussen, S. G.; Thian, F. S.; Kobilka, T. S.; Choi, H.-J.; Yao, X.-J.; Weis, W. I; Stevens, R. C.; Kobilka, B. K. GPCR Engineering Yields High-Resolution Structural Insights into 2 Adrenergic Receptor Function. Science, 2007, 318 (5854), 1266-73.
36. Cherezov, V.; Rosenbaum, D. M.; Hanson, M. A.; Rasmussen, S. G.; Thian, F. S.; Kobilka, T. S.; Choi, H.-J.; Kuhn, P.; Weis, W. I; Kobilka, B. K.; and Stevens, R. C. High-Resolution Crystal Structure of an Engineered Human 2-Adrenergic G Protein-Coupled Receptor. Science, 2007, 318(5854), 1258-65.
37. Hanson, M. A.; Cherezov, V.; Griffith, M. T.; Roth, C. B.; Jaakola, V. P.; Chien, E. Y.; Velasquez, J.; Kuhn, P.; Stevens, R. C. A specific cholesterol binding site is established by the 2.8 Å structure of the human beta2-adrenergic receptor. Structure, 2008, 16(6), 897-905.
38. Warne, T.; Serrano-Vega, M. J.; Baker, J. G.; Moukhametzianov, R.; Edwards, P. C.; Henderson, R.; Leslie, A. G.; Tate, C. G.; Schertler, G. F. Structure of a beta(1)-adrenergic G-protein-coupled receptor. Nature, 2008, 454(7203), 486-91.
39. Zhang, Y.; Sham, Y. Y.; Rajamani, R.; Gao, J. L.; Portoghese, P. S. Homology Modeling of the Mu Opioid Receptor Built in a Complete Membrane-Aqueous System. ChemBioChem, 2005, 6, 853-9.
40. Metzger, T. G.; Paterlini, M. G.; Ferguson, D. M.; Portoghese, P. S. Investigation of the selectivity of oxymorphone- and naltrexone-derived ligands via site-directed mutagenesis of opioid receptors: exploring the "address" recognition locus. J Med Chem., 2001, 44, 857-62.
41. Ulens, C.; Baker, L.; Ratka, A.; Waumans, D.; Tytgat, J. Morphine-6beta-glucuronide and morphine-3-glucuronide, opioid receptor agonists with different potencies. Biochem Pharmacol., 2001, 62, 1273-82.
42. Fowler, C. B.; Pogozheva, I. D.; LeVine, H. 3rd; Mosberg, H. I. Refinement of a homology model of the mu-opioid receptor using distance constraints from intrinsic and engineered zinc-binding sites. Biochemistry, 2004, 43, 8700-10.
43. Xue, J-C.; Chen, C.; Zhu, J.; Kunapuli, S. P.; de Riel, J. K.; Yu, L.; Liu-Chen, L-Y. The third extracellular loop of the mu opioid receptor is important for agonist selectivity. J. Biol. Chem., 1995, 270, 12977-12979.
44. Bonner, G.; Meng, F.; Akil, H. Selectivity of mu-opioid receptor determined by interfacial residues near the third extracellular loop. European J. Pharmacol., 2000, 403, 37-44.
45. Zhu, J.; Xue, J-C.; Law, P-Y.; Claude, P. A.; Luo, L-Y.; Yin, J.; Chen, C.; Liu-Chen; L-Y. The region in the mu opioid receptor conferring selectivity for sufentanil over the delta receptor is different from that over the kappa receptor. FEBS Letters, 1996, 384, 198-202.
46. Xu, W.; Li, J.; Chen, C.; Huang, P.; Weinstein, H.; Javitch, J. A.; Shi, L.; de Riel, J. K.; Liu-Chen, L. Y. Comparison of the amino acid residues in the sixth transmembrane domains accessible in the binding-site crevices of mu, delta, and kappa opioid receptors. Biochemistry, 2001, 40, 8018-29.
47. Law, P. Y.; Wong, Y. H.; Loh, H. H. Mutational analysis of the structure and function of opioid receptors. Biopolymers. 1999, 51(6): 440-55.
48. Xu, H.; Lu, Y. F.; Partilla, J. S.; Zheng, Q. X.; Wang, J. B.; Brine, G. A.; Carroll, F. I.; Rice, K. C.; Chen, K. X.; Chi, Z. Q.; Rothman, R. B. Opioid peptide receptor studies, 11: involvement of Tyr148, Trp318 and His319 of the rat β-opioid receptor in binding of β-selective ligands. Synapse (New York) 1999, 32(1), 23-28.
49. Griffin, J. F.; Larson, D. L.; Portoghese, P. S. Crystal structures of alpha- and beta-funaltrexamine: conformational requirement of the fumaramate moiety in the irreversible blockage of mu opioid receptors. J. Med. Chem. 1986, 29(5), 778-83.
50. Sayre, L. M.; Portoghese, P. S. Stereospecific synthesis of the 6α- and 6β-amino derivatives of naltrexone and oxymorphone. J. Org. Chem. 1980, 45, 3366-8.
51. Keen, M. Testing models of agonism for G protein-coupled receptors. Trends Pharmacol. Sci. 1991, 12(10), 371-4.
52. Selley, D. E.; Sim, L. J.; Xiao, R.; Liu, Q.; Childers, S. R. Mu-Opioid receptor-stimulated guanosine-5'-O-(gamma-thio)-triphosphate binding in rat thalamus and cultured cell lines: signal transduction mechanisms underlying agonist efficacy. Mol. Pharmacol. 1997, 51(1), 87-96.
53. Selley, D. E.; Liu, Q.; Childers, S. R. Signal transduction correlates of mu opioid agonist intrinsic efficacy: Receptor-stimulated [$^{35}$S]GTPγS binding in mMOR-CHO cells and rat thalamus. J. Pharmacol. Exp. Ther. 1998, 285, 496-505.
54. Morgan, D.; Cook, C. D.; Picker, M. J. Sensitivity to the discriminative stimulus and antinociceptive effects of mu opioids: role of strain of rat, stimulus intensity, and intrinsic efficacy at the mu opioid receptor. J Pharmacol Exp Ther. 1999, 289(2), 965-75.
55. Morgan, D.; Cook, C. D.; Smith, M. A.; Picker, M. J. An examination of the interactions between the antinociceptive effects of morphine and various mu-opioids: the role of intrinsic efficacy and stimulus intensity. Anesth Analg. 1999, 88(2), 407-13.
56. To further verify the role of Tyr210 and Trp318 in the binding of two leads to MOR, we conducted an initial site-directed mutagenesis study with CHO cells transiently transfected with the wild type and mutant MORs (Y210A and W318A). Naltrexone was used as control ligand and its binding affinity did not change much in both wild-type (wt) and mutant MORs (IC$_{50}$ values were 3.90±2.96 nM (wt), 0.95±0.49 nM (Y210A), and 10.35±1.64 nM (W318A) respectively). Both compound 6 and 9 bound to the Y210A mutant MOR with comparable affinities (IC50, 6, 1.61±0.17 nM; 9, 3.31±1.71 nM) as to the wild-type MOR (IC50, 6, 2.29±0.15 nM; 9, 5.42±0.70 nM), whereas their affinities were dramatically lower in binding to the W318A mutant (IC50, 6, >1,000 nM; 9, >1,000 nM). We will revisit these studies with wider concentration range in order to define the 1050 and Ki values for this mutant. These results indicate that these two leads could recognize an "address" locus with potential hydrogen bonding property in the MOR, which could confer their selectivity for the MOR over the DOR and KOR.
57. InsightII User Guide, October 1995. San Diego: MSI, 1995.
58. Coderre, T. J.; Rollman, G. B. Naloxone hyperalgesia and stress-induced analgesia in rats. Life Sci. 1983, 32(18), 2139-46.
59. Harris, L. S.; Pierson, A. K. Some narcotic antagonists in the benzomorphan series. J. Pharmacol. Exp. Ther. 1964, 143, 141-148.
60. Bliss, C. I. Statistics in Biology; McGraw-Hill: New York, 1967; p 439.

Example 3

Exemplary Compound Derivatives: from Compound 6 Defined Above in Examples 2 (Referred to as Compound 1 in this Example)

Figure 11:
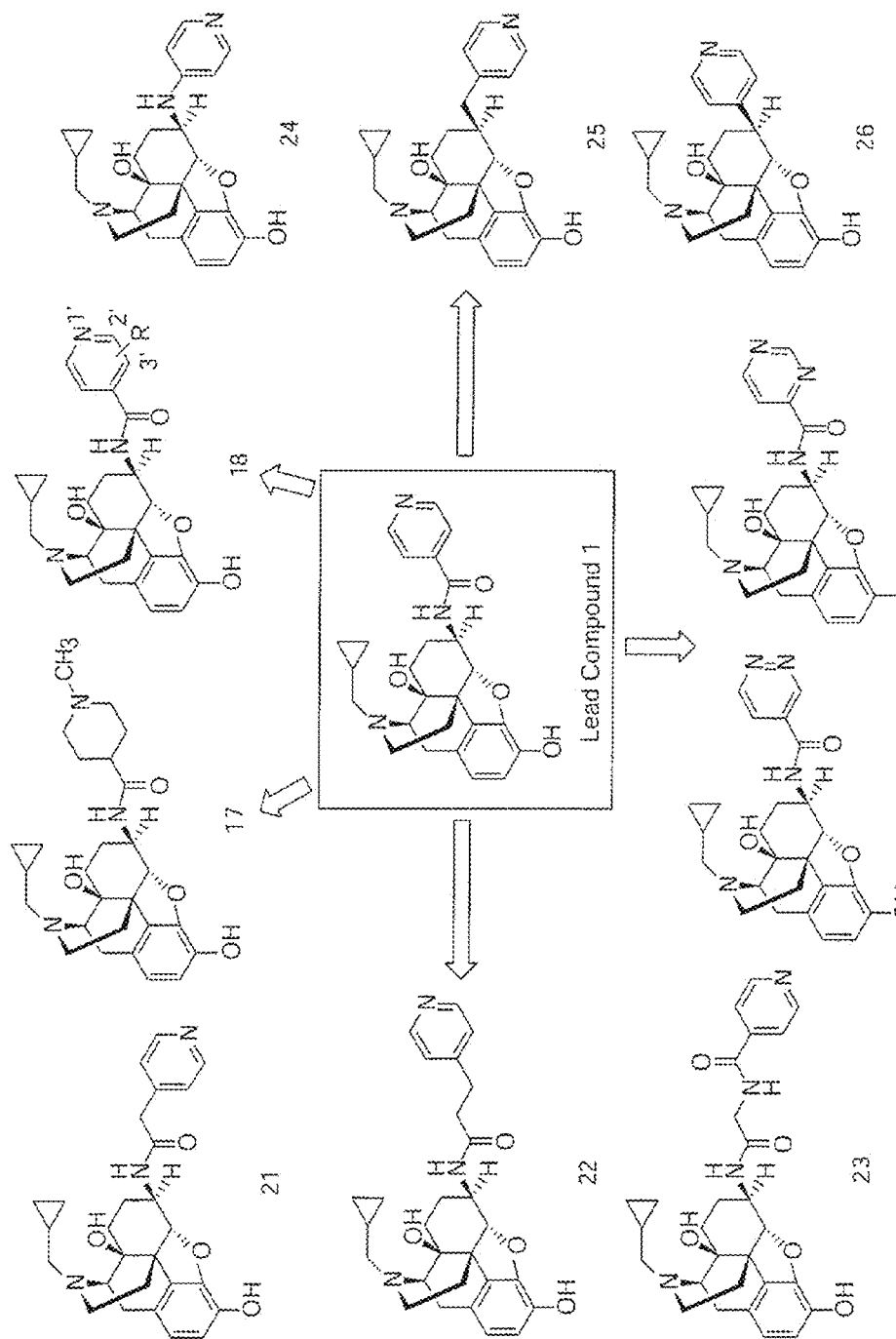
FIG. 11. Derivatives of compound 1.
Figure 12A:
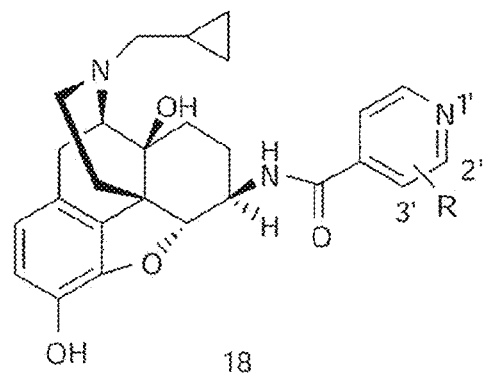
FIGS. 12A and B. Possible substitutions on the side chain aromatic system of compound 18.

New ligands based on exemplary compound 1 are used to further explore the structure-activity-relationships of these naltrexamine derivatives. The major morphinan skeleton and the C(6)-heterocyclic ring system are retained because they provided very high affinity for the MOR. Some adjustments are introduced to influence the orientation and the distance between these two moieties and to strengthen interactions (e.g. hydrogen bonding) between the ligand and the aromatic amino acid residues in the MOR. These interactions are believed to be important not only to the ligand binding affinity/selectivity for the receptor, but also to the optimization of the antagonism of the ligand. These compounds are synthesized and characterized by NMR, IR, Mass Spectrometry, elemental analysis and biological screening essentially as described in Examples 1 and 2. MOR antagonists based on exemplary compound 1 are depicted in FIG. 11. In addition, for compound 18, (FIG. 12A) various side chain substitutions are made as described in Table 6.

TABLE 6

The possible substitutions on the side chain aromatic system of 18

| | Substitutions |
|---|---|
| Position 2' | CH$_3$O, CH$_3$, Cl, Br, CN |
| Position 3' | CH$_3$O, CH$_3$, Cl, Br, CN |

Figure 12B:
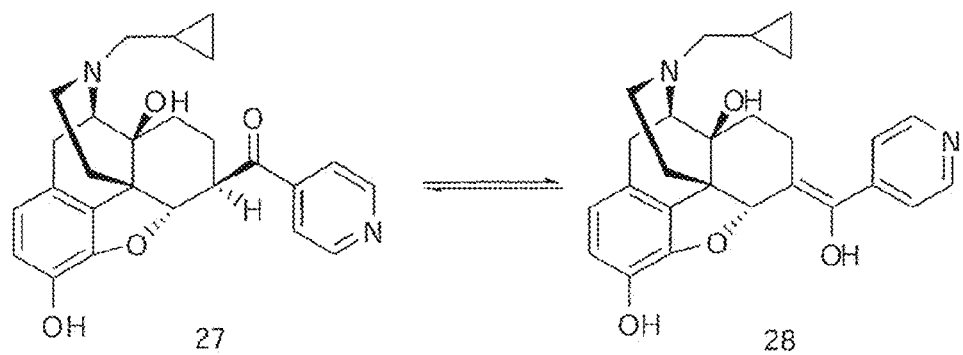

Additional embodiments of antagonists are depicted in FIG. 12B.

For the chemical synthesis of some new ligands conditions described in Examples 1 and 2 (e.g. FIG. 9) are adopted. Some of the proposed side chain moieties are not commercially available and are synthesized via the routes shown in Table 7, whereas others are commercially available in grain quantities.

TABLE 7

The availability of side chain moieties for derivatives of exemplary compound 1

| Target compound | Side chain moiety | Commercial availability or chemical synthetic preparation route (references for each step Included) |
|---|---|---|
| 17 | 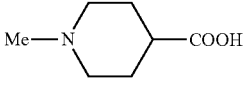 | 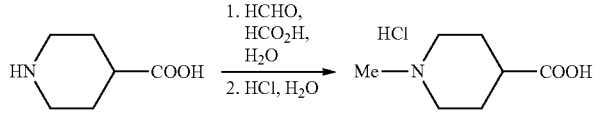 |

[153]

TABLE 7-continued

The availability of side chain moieties for derivatives of exemplary compound 1

| Target compound | Side chain moiety | Commercial availability or chemical synthetic preparation route (references for each step Included) |
|---|---|---|
| 19 | pyridazine-4-COOH | Aldrich USA (in gram scale) |
| 20 | pyrimidine-COOH | pyrimidine-Me → (SeO$_2$, t-BuOOH, Dioxane, 50° C.) → pyrimidine-COOH [154] |
| 21 | pyridine-4-CH$_2$COOH | Aldrich USA (in gram scale) |
| 22 | pyridine-4-(CH$_2$)$_2$COOH | pyridine-4-(CH$_2$)$_2$OH → (Swern Oxidation) → (m-ClPhCO$_3$H) → pyridine-4-(CH$_2$)$_2$COOH [155] |
| 23 | pyridine-4-C(O)NHCH$_2$COOH | pyridine-4-COOH + glycine ethyl ester (EDCI, HOBt, DMF) → (NaOH, THF, H$_2$O) → pyridine-4-C(O)NHCH$_2$COOH [156] |
| 18 | 2-MeO-pyridine-4-COOH | Matrix Scientific, SC. (in gram scale or Combi-Blocks, CA. (in gram scale) |
|  | 2-Me-pyridine-4-COOH | chromone-3-CHO + H$_2$NCH$_2$CO$_2$Et → (p-MeC$_6$H$_4$SO$_3$H, Toluene) → (KOH, H$_2$O) → (MCPBA, CHCl$_3$) → (P(OEt)$_3$, PhBr) → (H$_2$SO$_4$, AcOH) → 2-Me-pyridine-4-COOH [157] |
|  | 2-Cl-pyridine-4-COOH | Aldrich USA (in gram scale) |
|  | 2-Br-pyridine-4-COOH | Matrix Scientific, SC. (in gram scale) |

TABLE 7-continued

The availability of side chain moieties for derivatives of exemplary compound 1

| Target compound | Side chain moiety | Commercial availability or chemical synthetic preparation route (references for each step Included) |
|---|---|---|
| | 2-cyano-4-pyridinecarboxylic acid (NC on pyridine with COOH) | HOOC-pyridine →(H₂O₂, H₂O / AcOH, 90° C.) HOOC-pyridine N=O →(Et₃N, Me₃SiCl₂ / NaCN, DMF, 105° C.) HOOC-pyridine-CN [158] |
| | 3-methoxy-4-pyridinecarboxylic acid (OMe) | 3B Medical System Product (in gram scale) |
| | 3-methyl-4-pyridinecarboxylic acid | pyridine-CH₃ →(KMnO₄ or SeO₂) pyridine-COOH with methyl [159] |
| | 3-chloro-4-pyridinecarboxylic acid (Cl) | Aldrich USA (in gram scale) |
| | 3-bromo-4-pyridinecarboxylic acid (Br) | Matrix Scientific, SC. (in gram scale) |
| | 3-cyano-4-pyridinecarboxylic acid (CN) | pyridine-CN with CH₃ →(KMnO₄ or SeO₂) pyridine-COOH with CN [159] |

Figure 13:
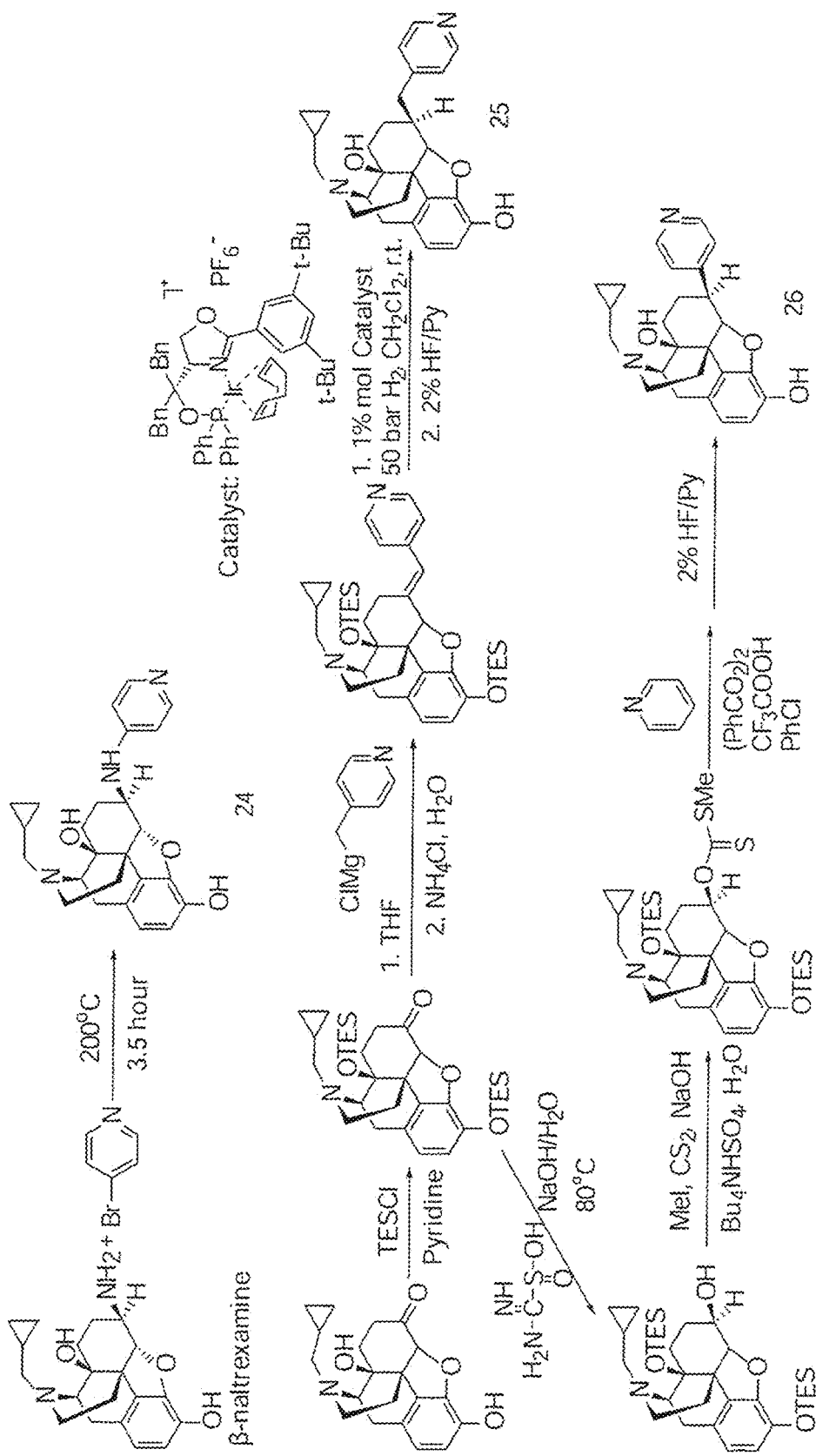
FIG. 13. The chemical synthesis routes for compounds 24, 25, and 26.

The chemical synthesis of Compounds 24, 25 and 26 differs from previously introduced routes. Therefore, new synthetic routes have been designed as shown in FIG. 13. As shown, the reaction condition to prepare compound 24 might be too harsh for the opiate starting material [Bailey D M, DeGrazia C G, Hoff S J, Schulenberg P L, O'Connor J R, Paris D A, Slee A M. Journal of Medicinal Chemistry 1984, 27(11), 1457-64]. Alternatively, NaOH is used as the base and the reaction is conducted in dioxane under high-pressure [Kotsuki H, Sakai H, Shinohara T. High-pressure organic chemistry. Part 23. Synlett 2000, (1), 116-118]. For compound 25, the enantioselective reduction of the double bond is challenging. Because the substrate carries a "largely unsubstituted" double bond [Cui X, Burgess K. Chemical Reviews, 2005, 105(9), 3272-96], one of the most reliable methods is the adoption of a cationic Iridium complex catalyst [Lightfoot A, Schnider P, Pfaltz A. Angewandte Chemie, International Edition, 1998, 37(20), 2897-2899; Blackmond D G, Lightfoot A, Pfaltz A, Rosner T, Schnider P, Zimmermann N. Chirality 2000, 12 (5-6), 442-9; Blankenstein J, Pfaltz A. Angewandte Chemie, International Edition, 2001, 40(23), 4445-4447; Menges F, Pfaltz A. Advanced Synthesis & Catalysis 2002, 344(1), 40-44; Pfaltz A, Blankenstein J, Hilgraf R, Hormann E, McIntyre S, Menges F, Schonleber M, Smidt S P, Wustenberg B, Zimmermann N. Advanced Synthesis & Catalysis 2003, 345 (1+2), 33-44]. Such a catalyst leads to up to 99% stereoselectivity. The absolute stereochemistry of the new chiral center in the opioid ligand is assigned by $^1$HNMR. Alternatively, D-serine, instead of L-serine, is adopted to prepare the enantiomer of the listed catalyst in four steps to give the desired chirality of the designed ligand 25 [Blankenstein, supra]. The starting material to synthesize compound 26 is protected β-naltrexol. It is prepared predominantly by adopting formamidinesulfinic acid under alkaline conditions with approximately 90% yield [Chatterjie N, Inturrisi C E. J Med Chem. 1975, 18(5), 490-2.].

For purposes of example and not limitation, nineteen new compounds have been designed as compound 1 derivatives. The syntheses of these 19 ligands include the multiple-step chemical synthesis of eight essential side chains as the starting material.

Characterization and biological testing of these compounds is carried out as described in Examples 1 and 2.

Example 4

Derivatives of Exemplary Compound 9 Defined Above in Example 2 (Referred to as Compound 2 in this Example)

Figure 14:
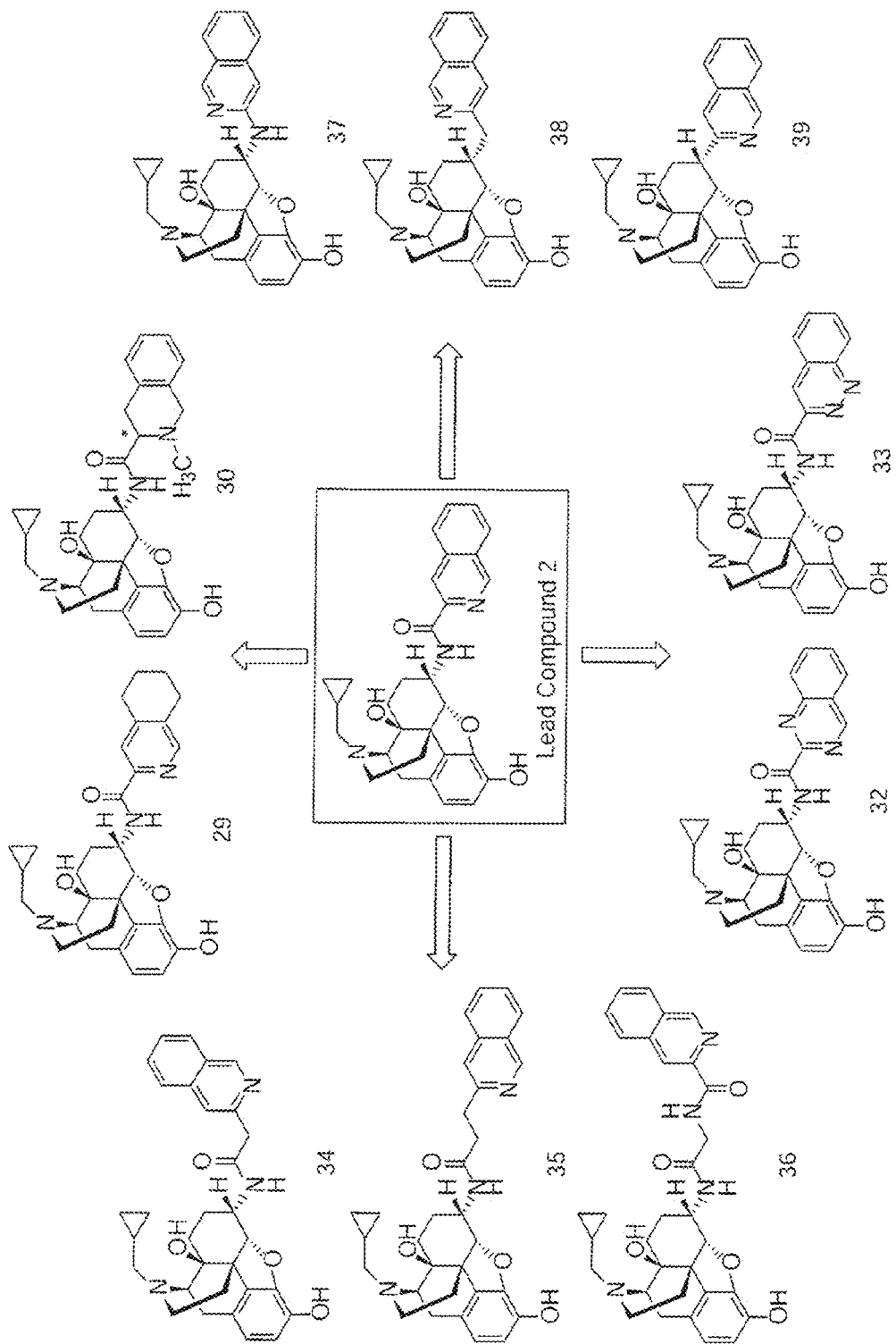
FIG. 14. Derivatives of compound 2.

Derivatives of compound 2 are depicted in FIG. 14. Similar to the derivatives of compound 1, compound 29 and 30 are designed to test the necessity of the aromatic system in the side chain for the affinity and selectivity of exemplary compound 2. Structure 30 actually represents two isomers because of the introduction of a new chiral center on the side chain. Both of these isomers are synthesized individually because optically pure side chain moieties can be prepared from commercially available optically pure starting material (Table 8, where references for each step are known to those of skill in the art).

Figure 15:
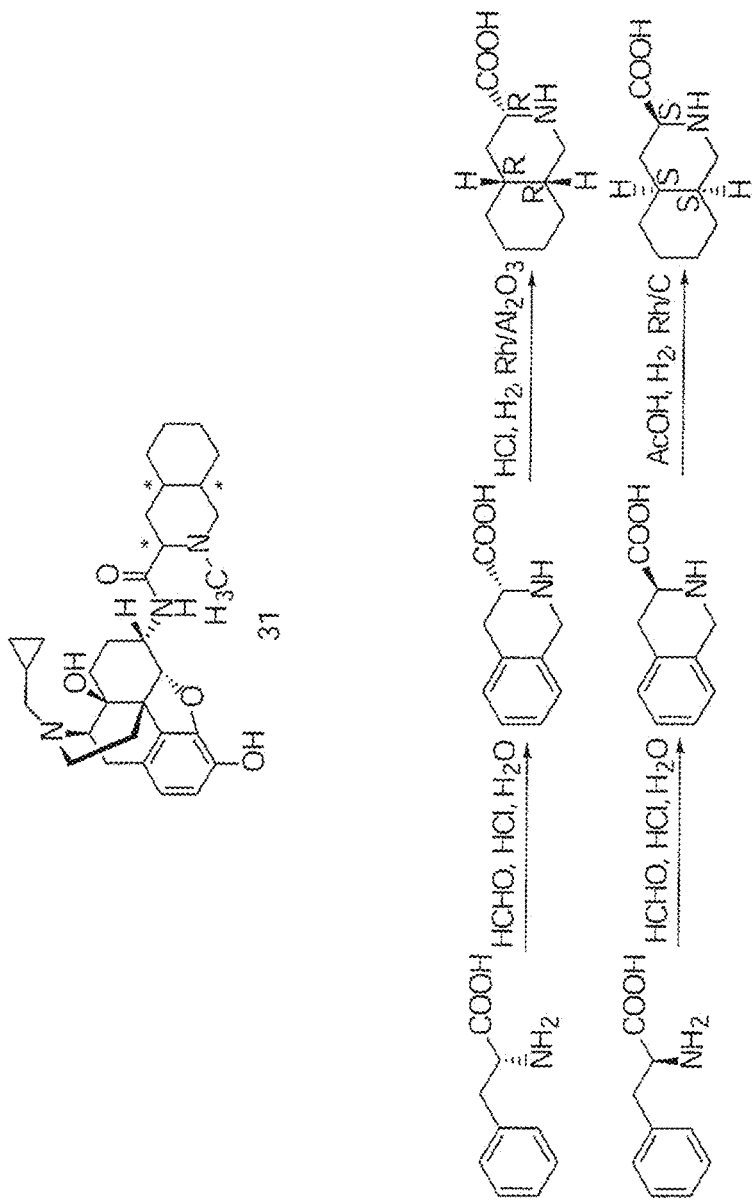
FIG. 15. Isomers and chemical synthesis scheme of compound 31.
Figure 16:
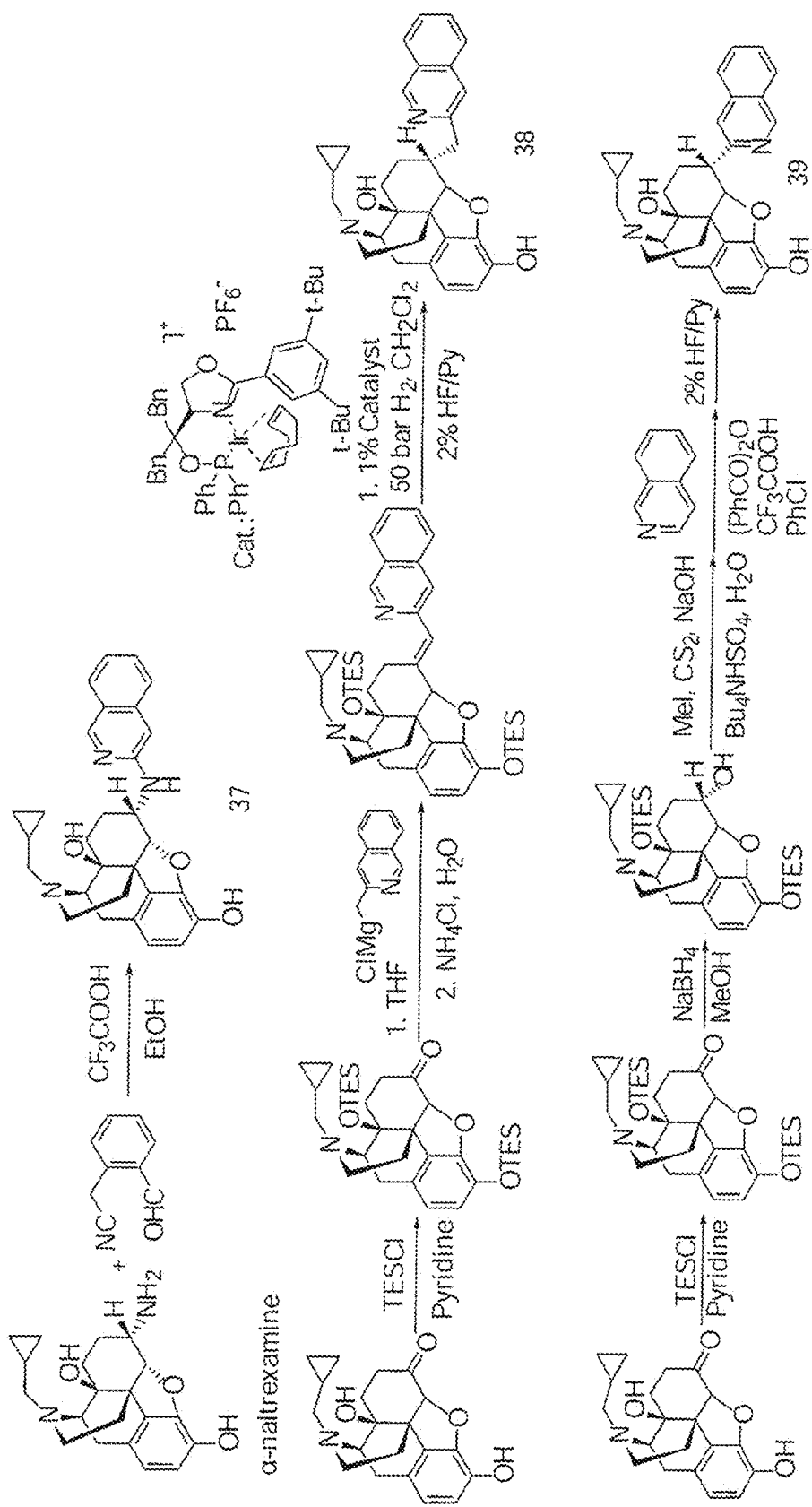
FIG. 16. The chemical synthesis routes for compound 37, 38 and 39.

Compound 31 (FIG. 15) has a totally saturated side chain moiety. Compound 31 actually is related to the synthesis of eight different isomers because there are three chiral centers in the side chain. At least two isomers can be synthesized following reported procedures [Repala R T, Lavagnino E R, Shepard E R, Farkas E. Journal of the American Chemical Society 1957, 79, 3770-2; Roberts N A, Martin J A, Kinchington D, Broadhurst A V, Craig J C, Duncan I B, Galpin S A, Handa B K, Kay J, Kröhn A, et al. Science. 1990, 248(4953), 358-61; Martin J A, Redshaw S. Eur. Pat. Appl. (1991), 17 pp. EP 432695 A2; Chirgadze N Y, Schacht A L, Smith G F, Willey M R. PCT Int. Appl. (1995), 129 pp. WO 9523608 A1 19950908 CAN 123:306600 AN 1995:899178; Shuman R T, Rothenberger R B, Campbell C S, Smith G F, Gifford-Moore D S, Paschal J W, Gesellchen P D. J Med Chem. 1995, 38(22), 4446-53.]. Depending on the affinity of compound 29 and 30 for the MOR, these two isomers are prepared and their affinity for the MOR is checked to verify the importance of aromaticity of the side chain (FIG. 16).

TABLE 8

The availability of side chain moieties for the newly designed derivatives of exemplary compound 2

| Target compound | Side chain moiety | Chemical synthetic preparation route |
|---|---|---|
| 29 | HOOC-tetrahydroisoquinoline | Cl-tetrahydroisoquinoline → (CF$_3$SO$_3$H, SbF$_3$, 1 h, 25° C.; NaHCO$_3$, H$_2$O) → HO-tetrahydroisoquinoline → (POCl$_3$) → Cl-tetrahydroisoquinoline → (KCN, CuCN; H$_2$O, 180-190° C.) → HOOC-tetrahydroisoquinoline |
| 30 | tetrahydroisoquinoline-COOH (N-CH$_3$) | tetrahydroisoquinoline-COOH (NH) → (1. HCHO, HCO$_2$H, H$_2$O; 2. HCl, H$_2$O) → tetrahydroisoquinoline-COOH (N-CH$_3$) |
| 32 | quinazoline-COOH | 2-methylquinazolin-4(3H)-one → (PCl$_3$/POCl$_3$; PdCl$_2$/MgO/H$_2$) → 2-methylquinazoline → (SeO$_2$) → quinazoline-COOH [18 |
| 33 | cinnoline-COOH | 2-methylindoline-NH$_2$ → (O$_2$) → 2-methylindole-NH$_2$ → (PhNO$_2$, 3% HCl—MeOH, Reflux, 42 h) → 3-methylcinnoline → (KMnO$_4$) → cinnoline-3-COOH |

TABLE 8-continued

The availability of side chain moieties for the newly designed derivatives of exemplary compound 2

| Target compound | Side chain moiety | Chemical synthetic preparation route |
| --- | --- | --- |
| 34 | | |
| 35 | | |
| 36 | | |

Figure 5:
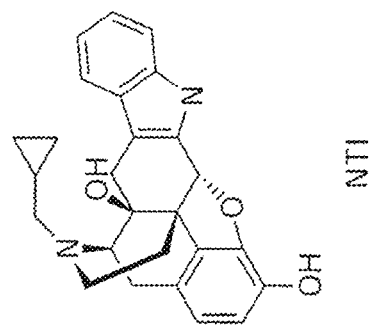
FIG. 5. The kappa opioid receptor selective antagonist norBNI, GNTI and the delta opioid receptor selective antagonist NTI FIG. 6. The mu opioid receptor selective antagonists.
Figure 5:
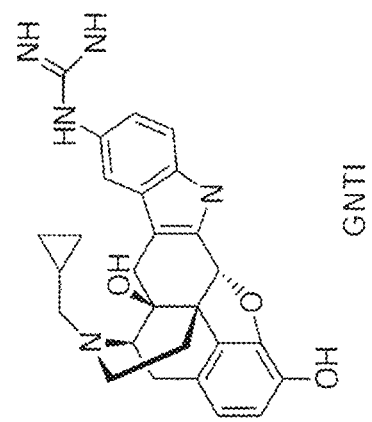
Figure 5:
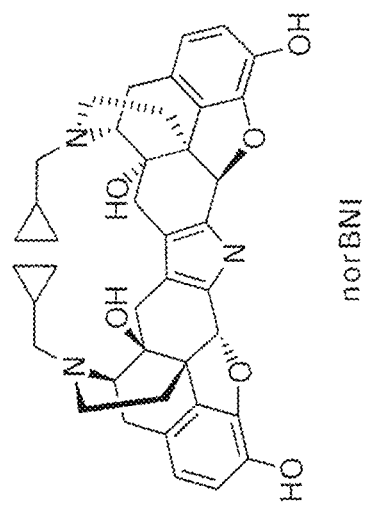

For compounds 29 to 36, their synthetic routes will be the same as in FIG. 5. For compounds 37, 38 and 39, new synthetic routes have been designed (FIG. 17). Compound 37 can be synthesized under acidic conditions [Zdrojewski T, Jonczyk A. Tetrahedron 1995, 51(45), 12439-44; Jonczyk A, Lipiak D, Sienkiewicz K. Synlett 1991, (7), 493-6.]. Similar to the preparation of compound 25, the preparation of compound 38 involves the stereoselective reduction of a double bond intermediate [Lightfoot A, Schnider P, Pfaltz A. Angewandte Chemie, International Edition, 1998, 37(20), 2897-2899; Blackmond D G, Lightfoot A, Pfaltz A, Rosner T, Schnider P, Zimmermann N. Chirality 2000, 12 (5-6), 442-9; Blankenstein I, Pfaltz A. Angewandte Chemie, International Edition, 2001, 40(23), 4445-4447; Menges F, Pfaltz A. Advanced Synthesis & Catalysis 2002, 344(1), 40-44; Pfaltz A, Blankenstein J, Hilgraf R, Hormann E, McIntyre S, Menges F, Schonleber M, Smidt S P, Wustenberg B, Zimmermann N. Advanced Synthesis & Catalysis 2003, 345 (1+2), 33-44]. The starting material to synthesize compound 39 is TES-protected β-naltrexol, and it can be prepared stereoselectively using NaBH4 reduction under low temperature [Uwai K, Uchiyama H, Sakurada S, Kabuto C, Takeshita M. Bioorganic & medicinal chemistry 2004, 12(2), 417-211. The rest of the steps are similar to the preparation of compound 26.

For purposes of example and no limitation, thirteen new compounds as derivatives of exemplary compound 2 have been proposed. The synthesis of these thirteen ligands includes the multiple-step preparation of at least nine of side chain moieties as starting material (Table 8).

Characterization and biological testing of these compounds is carried out essentially as described in Examples 1 and 2.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A selective, non-peptide MOR antagonist represented by formula

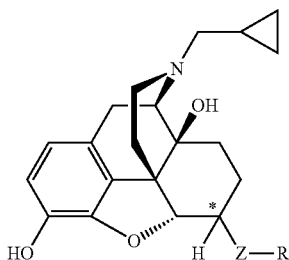

where
Z is selected from the group consisting of an aliphatic moiety, NH, CO, (NHCO)n where n=1-5, (CONH)n where n=1-5, (NHCO)(CH$_2$)n(NHCO), where n=1-5, (NHCO)(CH$_2$)n where n=1-5, (CH$_2$)n(NHCO), where n=1-5, and O, and R is selected from the group consisting of

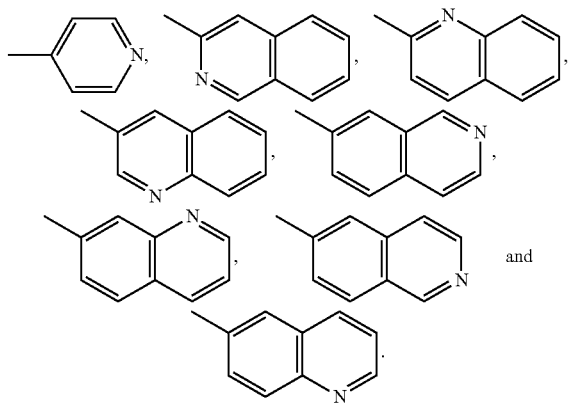

2. The selective, non-peptide MOR antagonist of claim 1, wherein said non-peptide MOR antagonist is represented by formula

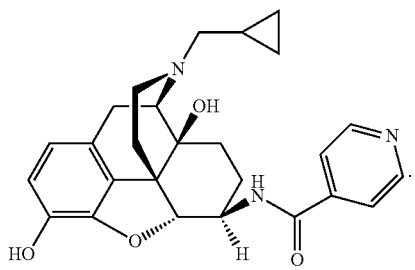

3. The selective, non-peptide MOR antagonist of claim 1, wherein said non-peptide MOR antagonist is represented by formula

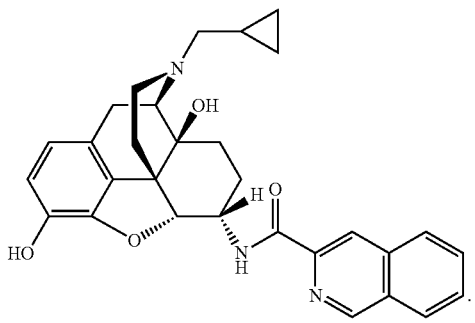

4. A method of testing whether or not a candidate compound is a MOR agonist, comprising the step of
conducting competitive inhibition tests between said candidate compound and a MOR antagonist represented by formula

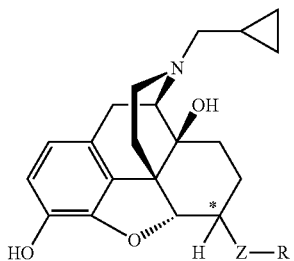

where
Z is selected from the group consisting of an aliphatic moiety, NH, CO, (NHCO)n where n=1-5, (CONH)n where n=1-5, (NHCO)(CH$_2$)n(NHCO), where n=1-5, (NHCO)(CH$_2$)n where n=1-5, (CH$_2$)n(NHCO), where n=1-5, and O, and R is selected from the group consisting of

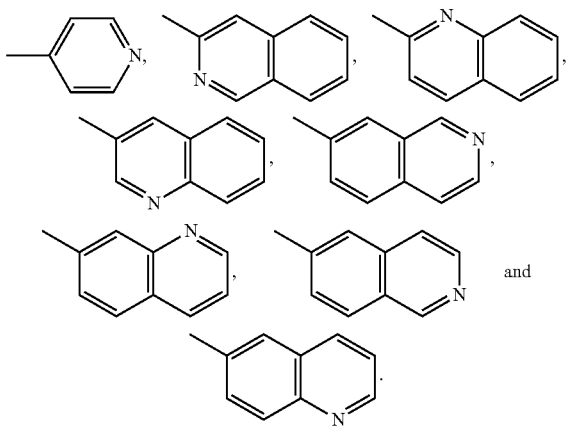

5. A method of treating symptoms of opiate addiction in a patient in need thereof, comprising
administering to said patient a MOR antagonist represented by formula

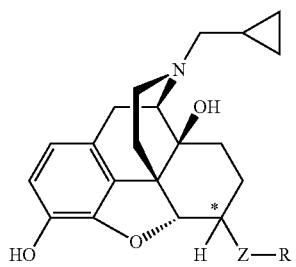
where
- Z is selected from the group consisting of an aliphatic moiety, NH, CO, (NHCO)n where n=1-5, (CONH)n where n=1-5, (NHCO)(CH$_2$)n(NHCO), where n=1-5, (NHCO)(CH$_2$)n where n=1-5, (CH$_2$)n(NHCO), where n=1-5, and O, and
- R is selected from the group consisting of
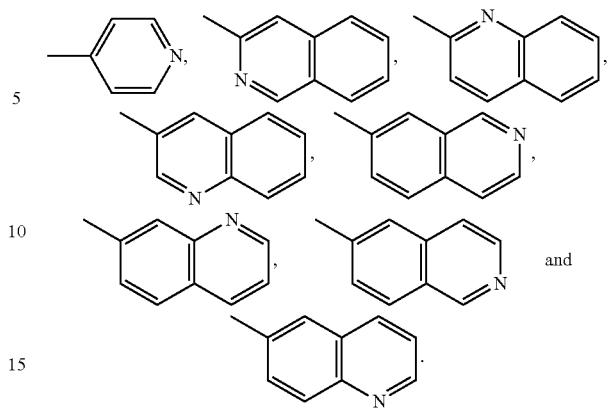
* * * * *

UNITED STATES PATENT AND TRADEMARK OFFICE
CERTIFICATE OF CORRECTION

PATENT NO. : 8,772,308 B2
APPLICATION NO. : 13/144788
DATED : July 8, 2014
INVENTOR(S) : Y Zhang, D. Selley and W. Dewey It is certified that error appears in the above-identified patent and that said Letters Patent is hereby corrected as shown below:

In the Specification

Column 1, delete lines 7-10 and insert the following:

--This invention was made with government support under contract number DA024022 awarded by the National Institutes of Health. The government has certain rights in the invention.--

Signed and Sealed this
Seventh Day of October, 2014

Michelle K. Lee
*Deputy Director of the United States Patent and Trademark Office*